United States Patent
Hodgetts et al.

(10) Patent No.: US 11,377,436 B2
(45) Date of Patent: Jul. 5, 2022

(54) EAAT2 ENHANCING MOLECULES

(71) Applicants: THE BRIGHAM AND WOMEN'S HOSPITAL, INC., Boston, MA (US); OHIO STATE UNIVERSITY, Columbus, OH (US)

(72) Inventors: Kevin Hodgetts, Framingham, MA (US); Chien-Liang Glenn Lin, Columbus, OH (US)

(73) Assignees: THE BRIGHAM AND WOMEN'S HOSPITAL, INC., Boston, MA (US); OHIO STATE UNIVERSITY, Columbus, OH (US)

( * ) Notice: Subject to any disclaimer, the term of this patent is extended or adjusted under 35 U.S.C. 154(b) by 0 days.

(21) Appl. No.: 16/630,677

(22) PCT Filed: Jul. 12, 2018

(86) PCT No.: PCT/US2018/041844
§ 371 (c)(1),
(2) Date: Jan. 13, 2020

(87) PCT Pub. No.: WO2019/014460
PCT Pub. Date: Jan. 17, 2019

(65) Prior Publication Data
US 2021/0163440 A1    Jun. 3, 2021

Related U.S. Application Data

(60) Provisional application No. 62/531,668, filed on Jul. 12, 2017.

(51) Int. Cl.
| | | |
|---|---|---|
| *C07D 401/04* | (2006.01) | |
| *A61P 25/28* | (2006.01) | |
| *C07D 213/75* | (2006.01) | |
| *C07D 239/42* | (2006.01) | |
| *C07D 241/18* | (2006.01) | |
| *C07D 241/20* | (2006.01) | |
| *C07D 401/14* | (2006.01) | |
| *C07D 413/14* | (2006.01) | |
| *C07D 417/14* | (2006.01) | |

(52) U.S. Cl.
CPC .......... *C07D 401/04* (2013.01); *A61P 25/28* (2018.01); *C07D 213/75* (2013.01); *C07D 239/42* (2013.01); *C07D 241/18* (2013.01); *C07D 241/20* (2013.01); *C07D 401/14* (2013.01); *C07D 413/14* (2013.01); *C07D 417/14* (2013.01)

(58) Field of Classification Search
CPC .. C07D 401/04; C07D 213/75; C07D 239/42; C07D 241/18; C07D 241/20; C07D 413/14; C07D 417/14
See application file for complete search history.

(56) References Cited

U.S. PATENT DOCUMENTS

| 10,016,398 B2 * | 7/2018 | Siddiqui-Jain ....... C07D 405/14 |
| 10,772,872 B2 * | 9/2020 | Siddiqui-Jain ....... C07D 401/14 |
| 2017/0172984 A1 * | 6/2017 | Siddiqui-Jain ....... C07D 405/14 |

OTHER PUBLICATIONS

Pennington, Bioorg & MEd Chem Letters, vol. 22, 2012, 527-531. (Year: 2012).*
Siddiqui_Jain, Bioorg & MEd CHem Letters, vol. 27, 2017, 3992-4000. (Year: 2017).*
Kirdajova, Frontiers in Cellular Neuroscience, Mar. 2020, vol. 14, article 51, 1-27. (Year: 2020).*
Kuo, Apr. 2014, (10 Supplement) vol. 82, abstract only. (Year: 2014).*
International Search Report and Written Opinion issued by the International Searching Authority (ISA/US) in PCT Application No. PCT/US2018/041844 dated Sep. 18, 2018. 10 pages.
Pubchem CID 100666531, pp. 1-11, Dec. 11, 2015.
Pubchem CID 74237045, pp. 1-11, Jun. 9, 2014.
Pubchem CID 56672027, pp. 1-14, Mar. 6, 2012.
Pubchem CID 91068286, pp. 1-10, Mar. 17, 2015.
Pubchem CID 59932585, pp. 1-12, Aug. 20, 2012.
Ayers-Ringler, Jennifer R., et al. "Role of astrocytic glutamate transporter in alcohol use disorder." World journal of psychiatry 6.1 (2016): 31-42.
Bacigaluppi, Marco, et al. "Neural stem cell transplantation induces stroke recovery by upregulating glutamate transporter GLT-1 in astrocytes." Journal of Neuroscience 36.41 (2016): 10529-10544.
Chen, Guang, Ioline D. Henter, and Husseini K. Manji. "Presynaptic glutamatergic dysfunction in bipolar disorder." Biological psychiatry 67.11 (2010): 1007.
Chizh, B. A. "Novel approaches to targeting glutamate receptors for the treatment of chronic pain." Amino Acids 23.1-3 (2002): 169-176.
Cisneros, E, et al., "HIV-1, methamphetamine and astrocyte glutamate regulation: combined excitotoxic implications for neuro-AIDS." Current HIV research 10.5 (2012): 392-406.
De Bartolomeis, Andrea, et al. "Targeting glutamate system for novel antipsychotic approaches: relevance for residual psychotic symptoms and treatment resistant schizophrenia." European journal of pharmacology 682.1-3 (2012): 1-11.
Descalzi, Giannina, Susan Kim, and Min Zhuo. "Presynaptic and postsynaptic cortical mechanisms of chronic pain." Molecular neurobiology 40.3 (2009): 253-9.
Dunkley, Peter R., Paula E. Jarvie, and Phillip J. Robinson. "A rapid Percoll gradient procedure for preparation of synaptosomes." Nature protocols 3.11 (2008): 1718-1728.
Ende, Gabriele, et al. "Impulsivity and aggression in female BPD and ADHD patients: association with ACC glutamate and GABA concentrations." Neuropsychopharmacology 41.2 (2016): 410-418.
Gegelashvili, Georgi, and Ole J. Bjerrum. "High-affinity glutamate transporters in chronic pain: An emerging therapeutic target." Journal of neurochemistry 131.6 (2014): 712-730.

(Continued)

*Primary Examiner* — D Margaret M Seaman
(74) *Attorney, Agent, or Firm* — Meunier Carlin & Curfman LLC

(57) ABSTRACT

The present application provides pyridine, pyrimidine, and pyrazine derivatives that activate excitatory amino acid transporter 2 (EAAT2), and methods of using the derivatives for treating or preventing diseases, disorders, and conditions associated with glutamate excitotoxicity.

19 Claims, No Drawings

(56) References Cited

OTHER PUBLICATIONS

Ghanizadeh, Ahmad, and B. E. R. K. Michael. "Beta-lactam antibiotics as a possible novel therapy for managing epilepsy and autism, a case report and review of Titerature." Iranian journal of child neurology 9.1 (2015): 99-102.

Guardia, Dewi, et al. "GABAergic and glutamatergic modulation in binge eating: therapeutic approach." Current pharmaceutical design 17.14 (2011): 1396-1409.

Guo, Hong, et al. "Increased expression of the glial glutamate transporter EAAT2 modulates excitotoxicity and delays the onset but not the outcome of ALS in mice." Human molecular genetics 12.19 (2003): 2519-2532.

Hazell, Alan S. "Excitotoxic mechanisms in stroke: an update of concepts and treatment strategies." Neurochemistry international 50.7-8 (2007): 941-953.

Hu, Neng-Wei, Tomas Ondrejcak, and Michael J. Rowan. "Glutamate receptors in preclinical research on Alzheimer's disease: update on recent advances." Pharmacology Biochemistry and Behavior 100.4 (2012): 855-862.

Jollant, Fabrice, et al. "Spectroscopy markers of suicidal risk and mental pain in depressed patients." Progress in neuro-psychopharmacology and biological psychiatry 73 (2017): 64-71.

Kaul, Marcus, and Stuart A. Lipton. "Mechanisms of neuronal injury and death in HIV-1 associated dementia." Current HIV research 4.3 (2006): 307-318.

Kim, Keetae, et al. "Role of excitatory amino acid transporter-2 (EAAT2) and glutamate in neurodegeneration: opportunities for developing novel therapeutics." Journal of cellular physiology 226.10 (2011): 2484-2493.

Kong, Qiongman, et al. "Small-molecule activator of glutamate transporter EAAT2 translation provides neuroprotection." The Journal of clinical investigation 124.3 (2014): 1255-1267.

Lapidus, Kyle AB, Laili Soleimani, and James W. Murrough. "Novel glutamatergic drugs for the treatment of mood disorders." Neuropsychiatric disease and treatment 9 (2013): 1101-12.

Larsson, Max. "Ionotropic glutamate receptors in spinal nociceptive processing." Molecular neurobiology 40.3 (2009): 260-288.

Lin, Hung-Yun, et al. "L-Thyroxine vs. 3, 5, 3'-triiodo-L-thyronine and cell proliferation: activation of mitogen-activated protein kinase and phosphatidylinositol 3-kinase." American Journal of Physiology—Cell Physiology 296.5 (2009): C980-C991.

Mark, Leighton P., et al. "Pictorial review of glutamate excitotoxicity: fundamental concepts for neuroimaging." American journal of neuroradiology 22.10 (2001) 1813-1824.

Melzer, Nico, et al. "A β-lactam antibiotic dampens excitotoxic inflammatory CNS damage in a mouse model of multiple sclerosis." PLoS One 3.9 (2008): e3149.

Miller, Benjamin R., et al. "Up-regulation of GLT1 reverses the deficit in cortically evoked striatal ascorbate efflux in the R6/2 mouse model of Huntington's disease." Journal of neurochemistry 121.4 (2012): 629-638.

Mineur, Yann S., Marina R. Picciotto, and Gerard Sanacora. "Antidepressant-like effects of ceftriaxone in male C57BL/6J mice." Biological psychiatry 61.2 (2007) 250-252.

Myers, Karyn M., William A. Carlezon, and Michael Davis. "Glutamate receptors in extinction and extinction-based therapies for psychiatric illness." Neuropsychopharmacology 36.1 (2011): 274-293.

Nakagawa, et al., Spinal Astrocytes as Therapeutic Targets for Pathological Pain J. Pharmacol. Sci. 2010;114(4):347-53.

Nakagawa, Takayuki, and Shuji Kaneko. "SLC1 glutamate transporters and diseases: psychiatric diseases and pathological pain." Current molecular pharmacology 6.2 (2013): 66-73.

Nakatsu, Yusuke, et al. "Glutamate excitotoxicity is involved in cell death caused by tributyltin in cultured rat cortical neurons." Toxicological Sciences 89.1 (2006) 235-242.

Nanitsos, Ellas K., et al. "Glutamatergic hypothesis of schizophrenia: involvement of Na+/K+-dependent glutamate transport." Journal of biomedical science 12.6 (2005): 975-984.

Noch, Evan, and Kamel Khalili. "Molecular mechanisms of necrosis in glioblastoma: the role of glutamate excitotoxicity." Cancer biology & therapy 8.19 (2009): 1791-1797.

Olney, "Neurotoxicity of excitatory amino acids." In: McGeer E, Olney J, McGeer P, eds. Kainic Acid as a Tool in Neurobiology. New York: Raven Press; 1978:95-121.

Olney, John W. "Role of excitotoxins in developmental neuropathology." Apmis. Supplementum 40 (1993): 103-112.

Owen, R. T. "Glutamatergic approaches in major depressive disorder: focus on ketamine, memantine and riluzole." Drugs of Today (Barcelona, Spain: 1998) 48.7 (2012): 469-478.

Pittenger, Christopher, Michael H. Bloch, and Kyle Williams. "Glutamate abnormalities in obsessive compulsive disorder: neurobiology, pathophysiology, and treatment." Pharmacology & therapeutics 132.3 (2011): 314-332.

Prost, Robert W., et al. "Detection of glutamate/glutamine resonances by 1H magnetic resonance spectroscopy at 0.5 tesla." Magnetic resonance in medicine 37.4 (1997): 615-618.

Reissner, Kathryn J., and Peter W. Kalivas. "Using glutamate homeostasis as a target for treating addictive disorders." Behavioural pharmacology 21.5-6 (2010): 514-22.

Roberts-Wolfe, Douglas, and Peter W Kalivas. "Glutamate transporter GLT-1 as a therapeutic target for substance use disorders." CNS & Neurological Disorders—Drug Targets (Formerly Current Drug Targets—CNS & Neurological Disorders) 14.6 (2015): 745-756.

Sattler, Rita, and Jeffrey D. Rothstein. "Targeting an old mechanism in a new disease—protection of glutamatergic dysfunction in depression." Biological psychiatry 61.2 (2007): 137-138.

Scofield, Michael D., and Peter W. Kalivas. "Astrocytic dysfunction and addiction consequences of impaired glutamate homeostasis." The Neuroscientist 20.6 (2014): 610-622.

Seifert, Gerald, Giorgio Carmignoto, and Christian Steinhauser. "Astrocyte dysfunction in epilepsy." Brain research reviews 63.1-2 (2010): 212-221.

Sheldon, Amanda L., and Michael B. Robinson. "The role of glutamate transporters in neurodegenerative diseases and potential opportunities for intervention." Neurochemistry international 51.6-7 (2007): 333-355.

Stephens Jr, Robert L. "Glutamate transporter activators as antinociceptive agents." The Eurasian journal of medicine 43.3 (2011): 182.

Takahashi, Kou, et al. "Restored glial glutamate transporter EAAT2 function as a potential therapeutic approach for Alzheimer's disease." Journal of Experimental Medicine 212.3 (2015): 319-332.

Tian, Guilian, et al. "Increased expression of cholesterol 24S-hydroxylase results in disruption of glial glutamate transporter EAAT2 association with lipid rafts: a potential role in Alzheimer's disease." Journal of neurochemistry 113.4 (2010): 978-989.

Tian, Guilian, et al. "Translational control of glial glutamate transporter EAAT2 expression." Journal of biological chemistry 282.3 (2007): 1727-1737.

Tiwari, Arun K., et al. "Impact of histamine receptors H1 and H3 polymorphisms on antipsychotic-induced weight gain." The World Journal of Biological Psychiatry 19.sup3 (2018): S97-S105.

Torres-Altoro, M. I., et al. "Organophosphates dysregulate dopamine signaling, glutamatergic neurotransmission, and induce neuronal injury markers in striatum [In Vitro, Research Support, NIH, Extramural, NIH, Intramural, US Gov't, Non-PHS, US Gov't, PHS] Journal of Neurochemistry, 119 (2), 303e313." (2011).

Tzschentke, T. M. "Glutamatergic mechanisms in different disease states: overview and therapeutical implications—an introduction." Amino Acids 23.1-3 (2002): 147-152.

Vargas, Bert B. "Chronic migraine: Current pathophysiologic concepts as targets for treatment." Current pain and headache reports 13.1 (2009): 64-66.

Wang, Yan, and Zheng-hong Qin. "Molecular and cellular mechanisms of excitotoxic neuronal death." Apoptosis 15.11 (2010): 1382-1402.

(56) References Cited

OTHER PUBLICATIONS

Wilen, S.H. Tables of Resolving Agents and Optical Resolutions, 1972, p. 268.

Wilen, Samuel H., André Collet, and Jean Jacques. "Strategies in optical Yesolutions." Tetrahedron 33.21 (1977): 2725-2736.

Yi, Jae-Hyuk, and Alan S. Hazell. "Excitotoxic mechanisms and the role of astrocytic glutamate transporters in traumatic brain injury." Neurochemistry international 48.5 (2006): 394-403.

Yogeswaari et al., "Current approaches with the glutamatergic system as targets in the treatment of neuropathic pain," Expert Opin Ther Targets, 2009, 13(8):925-43.

Yousuf, Muhammad Saad, and Bradley J. Kerr. "The role of regulatory transporters in neuropathic pain." Advances in Pharmacology. vol. 75. Academic Press, 2016. 245-271.

Zhang, Yunlong, et al. "Recent advance in the relationship between excitatory amino acid transporters and Parkinson's disease." Neural Plasticity 2016 https://doi.org/10.1155/2016/8941327.

Zumkehr, Joannee, et al. "Ceftriaxone ameliorates tau pathology and cognitive decline via restoration of glial glutamate transporter in a mouse model of Alzheimer's disease." Neurobiology of aging 36.7 (2015): 2260-2271.

International Preliminary Report on Patentability issued for Application No. PCT/US2018/041844, dated Jan. 23, 2020.

\* cited by examiner

EAAT2 ENHANCING MOLECULES

CROSS REFERENCE TO RELATED APPLICATIONS

This application is a national stage application filed under 35 U.S.C. § 371 of PCT/US2018/041844 filed Jul. 12, 2018, which claims the benefit of priority to U.S. Provisional Application 62/531,668, filed Jul. 12, 2017, which is incorporated by reference herein in its entirety.

STATEMENT REGARDING FEDERALLY SPONSORED RESEARCH OR DEVELOPMENT

This invention was made with government support under grant number AG054444 awarded by the National Institutes of Health. The government has certain rights in the invention.

STATEMENT REGARDING FEDERALLY FUNDED RESEARCH

This invention was made with government support under U01 AG054444 awarded by the National Institutes of Health. The government has certain rights in the invention.

TECHNICAL FIELD

The present description relates to pyridine, pyrimidine, and pyrazine derivatives that activate excitatory amino acid transporter 2 (EAAT2), and methods of use thereof for treating or preventing diseases, disorders, and conditions associated with glutamate excitotoxicity.

BACKGROUND

Glutamate is a major neurotransmitter in the mammalian central nervous system (CNS) and essential for normal brain function including cognition, memory, and learning. However, the extracellular concentration of glutamate must remain below excitotoxic levels (~1 µM) to avoid overstimulation of glutamate receptors, leading to neuronal damage or death (Sheldon and Robinson, Neurochem. Int. 2007, 51, 333). Excitotoxicity has been associated with multiple acute neurological conditions such as ischemic stroke, epilepsy, and trauma, chronic adult-onset neurodegenerative disorders such as Alzheimer's disease and amyotrophic lateral sclerosis (ALS) (Guo et al., Hum. Mol. Genet. 2003, 12, 2519; Tian et al., J. Biol. Chem. 2007, 282, 1727; Hazell, Neurochem. Int. 2007 50, 941; Seifert et al., Brain. Res. Rev. 2010, 63, 212; Tian et al., J. Neurochem. 2010, 113, 978), and depression. One potential approach to preventing excitotoxicity is to enhance glutamate reuptake. EAAT2 is the major glutamate transporter and functions to remove glutamate from synapses (Lin et al., Am. J. Physiol. Gastrointest Liver Physiol. 2009, 296, 129). An increase in EAAT2 protein expression and function can provide a means to prevent insufficient glutamate reuptake and consequently reduce neuronal damage.

SUMMARY

Provided herein is a compound of Formula I:

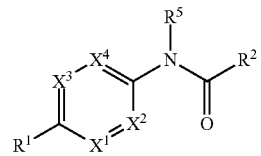

or a pharmaceutically acceptable salt thereof, wherein:
$X^1$ is CH or N;
$X^2$ is CH or N;
$X^3$ is $CR^3$ or N;
$X^4$ is $CR^4$ or N;
wherein the ring comprising $X^1$, $X^2$, $X^3$, and $X^4$ forms a pyridine ring, a pyrazine ring, or a pyrimidine ring;
$R^1$ is selected from the group consisting of 6-10 membered aryl and 5-10 membered heteroaryl, each of which is optionally substituted by 1, 2, 3, or 4 independently selected $R^A$ groups;
$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;
$R^3$, $R^4$, and $R^5$ are each independently selected from H and $C_{1-6}$ alkyl;
each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^dNR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;
each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;
each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and
each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is a 5-10 membered heteroaryl which is optionally substituted by 1, 2, 3, or 4 independently selected $R^A$ groups. For example, $R^1$ is an unsubstituted 5-6 membered heteroaryl. In some embodiments, $R^1$ is unsubstituted pyridyl.

In some embodiments, $R^2$ is selected from the group consisting of phenyl, 5-6 membered heteroaryl, and 4-6 membered heterocycloalkyl, each of which is optionally substituted by 1, 2, 3, or 4 independently selected $R^B$ groups. For example, $R^2$ is selected from the group consisting of phenyl, 5-6 membered heteroaryl, and 4-6 membered heterocycloalkyl, each of which is optionally substituted by 1 $R^B$ group. In some embodiments, each $R^B$ is independently selected from the group consisting of halo, $C_{1-6}$ alkyl, and $OR^a$. For example, each $R^B$ is independently selected from the group consisting of F, Cl, $C_{1-3}$ alkyl, and $C_{1-3}$ alkoxy.

In some embodiments, $R^3$ is H.

In some embodiments, $R^4$ is H.

In some embodiments, $R^5$ is H.

In some embodiments, the ring comprising $X^1$, $X^2$, $X^3$, and $X^4$ forms a pyridine ring. In some embodiments, the ring comprising $X^1$, $X^2$, $X^3$, and $X^4$ forms a pyrazine ring. In some embodiments, the ring comprising $X^1$, $X^2$, $X^3$, and $X^4$ forms a pyrimidine ring.

In some embodiments, the ring comprising $X^1$, $X^2$, $X^3$, and $X^4$ forms a pyridine ring, a pyrazine ring, or a pyrimidine ring; $R^1$ is a 5-6 membered heteroaryl which is optionally substituted by 1 or 2 independently selected $R^A$ groups; $R^2$ is selected from the group consisting of phenyl, 5-6 membered heteroaryl, and 4-6 membered heterocycloalkyl, each of which is optionally substituted by 1, 2, 3, or 4 independently selected $R^B$ groups; each $R^B$ is independently selected from the group consisting of halo, $C_{1-6}$ alkyl, and $OR^a$; $R^3$ is H; $R^4$ is H; and $R^5$ is H.

In some embodiments, the ring comprising $X^1$, $X^2$, $X^3$, and $X^4$ forms a pyridine ring, a pyrazine ring, or a pyrimidine ring; $R^1$ is an unsubstituted 5-6 membered heteroaryl; $R^2$ is selected from the group consisting of phenyl, 5-6 membered heteroaryl, and 4-6 membered heterocycloalkyl, each of which is optionally substituted by 1 or 2 independently selected $R^B$ groups; each $R^B$ is independently selected from the group consisting of halo, $C_{1-6}$ alkyl, and $OCH_3$; $R^3$ is H; $R^4$ is H; and $R^5$ is H.

Also provided herein is a compound of Formula II:

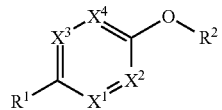

II or a pharmaceutically acceptable salt thereof, wherein:

$X^1$ is CH or N;

$X^2$ is CH or N;

$X^3$ is $CR^3$ or N;

$X^4$ is $CR^4$ or N;

wherein the ring comprising $X^1$, $X^2$, $X^3$, and $X^4$ forms a pyridine ring, a pyrazine ring, or a pyrimidine ring;

$R^1$ is selected from the group consisting of 6-10 membered aryl and 5-10 membered heteroaryl, each of which is optionally substituted by 1, 2, 3, or 4 independently selected $R^A$ groups;

$R^2$ is $-(CHR^E)_nR^5$;

$R^5$ is selected from the group consisting of $OR^C$, $NR^CR^D$, $C(O)NR^CR^D$, $C(O)OR^C$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^dNR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, $R^1$ is a 5-10 membered heteroaryl which is optionally substituted by 1, 2, 3, or 4 independently selected $R^A$ groups. For example, $R^1$ is an unsubstituted 5-6 membered heteroaryl. In some embodiments, $R^1$ is unsubstituted pyridyl.

In some embodiments, $R^2$ is selected from the group consisting of —$(CH_2)_nR^5$, —$(CH(CH_3))_nR^5$, and —$(CH_2CH(NH_2))_nR^5$.

In some embodiments, $R^3$ is H.

In some embodiments, $R^4$ is H.

In some embodiments, $R^5$ is selected from the group consisting of $OR^C$, $NR^CR^D$, $C(O)NR^CR^D$, $C_{6-10}$ aryl, $C_{3-10}$ cycloalkyl, 4-10 membered heterocycloalkyl, and 5-10 membered heteroaryl, wherein the $C_{6-10}$ aryl, $C_{3-10}$ cycloalkyl, 4-10 membered heterocycloalkyl, and 5-10 membered heteroaryl are each optionally substituted by 1, 2, 3, or 4 independently selected $R^B$ groups. For example, $R^5$ is selected from the group consisting of $OR^C$, $NR^CR^D$, $C(O)NR^CR^D$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups. In some embodiments, $R^5$ is selected from the group consisting of $OCH_3$, $N(CH_3)_2$, $C(O)N(CH_3)_2$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups. In some embodiments, each $R^B$ is independently selected from the group consisting of $C_{1-6}$ alkyl and $NR^cR^d$. For example, each $R^B$ is independently selected from the group consisting of $C_{1-3}$ alkyl and $N(C_{1-3}$ alkyl$)_2$.

In some embodiments, n is 0, 1, or 2.

In some embodiments, the ring comprising $X^1$, $X^2$, $X^3$, and $X^4$ forms a pyridine ring. In some embodiments, the ring comprising $X^1$, $X^2$, $X^3$, and $X^4$ forms a pyrazine ring. In some embodiments, the ring comprising $X^1$, $X^2$, $X^3$, and $X^4$ forms a pyrimidine ring.

In some embodiments, the ring comprising $X^1$, $X^2$, $X^3$, and $X^4$ forms a pyridine ring, a pyrazine ring, or a pyrimidine ring; $R^1$ is a 5-6 membered heteroaryl which is optionally substituted by 1 or 2 independently selected $R^A$ groups; $R^2$ is selected from the group consisting of —$(CH_2)_nR^5$, —$(CH(CH_3))_nR^5$, and —$(CH_2CH(NH_2))_nR^5$; $R^3$ is H; $R^4$ is H; $R^5$ is selected from the group consisting of $OR^C$, $NR^CR^D$, $C(O)NR^CR^D$, $C_{6-10}$ aryl, $C_{3-10}$ cycloalkyl, 4-10 membered heterocycloalkyl, and 5-10 membered heteroaryl, wherein the $C_{6-10}$ aryl, $C_{3-10}$ cycloalkyl, 4-10 membered heterocycloalkyl, and 5-10 membered heteroaryl are each optionally substituted by 1, 2, 3, or 4 independently selected $R^B$ groups; each $R^B$ is independently selected from the group consisting of $C_{1-6}$ alkyl and $NR^cR^d$; and n is 0, 1, 2, 3, 4, or 5.

In some embodiments, the ring comprising $X^1$, $X^2$, $X^3$, and $X^4$ forms a pyridine ring, a pyrazine ring, or a pyrimidine ring; $R^1$ is an unsubstituted 5-6 membered heteroaryl; $R^2$ is selected from the group consisting of —$(CH_2)_nR^5$, —$(CH(CH_3))_nR^5$, and —$(CH_2CH(NH_2))_nR^5$; $R^3$ is H; $R^4$ is H; $R^5$ is selected from the group consisting of $OR^C$, $NR^CR^D$, $C(O)NR^CR^D$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups; each $R^B$ is independently selected from the group consisting of $C_{1-6}$ alkyl and $NR^cR^d$; and n is 0, 1, or 2.

In some embodiments, the ring comprising $X^1$, $X^2$, $X^3$, and $X^4$ forms a pyridine ring, a pyrazine ring, or a pyrimidine ring; $R^1$ is unsubstituted pyridyl; $R^2$ is selected from the group consisting of —$(CH_2)_nR^5$, —$(CH(CH_3))_nR^5$, and —$(CH_2CH(NH_2))_nR^5$; $R^3$ is H; $R^4$ is H; $R^5$ is selected from the group consisting of $OCH_3$, $N(CH_3)_2$, $C(O)N(CH_3)_2$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups; each $R^B$ is independently is selected from the group consisting of $C_{1-3}$ alkyl and $N(C_{1-3}$ alkyl$)_2$; and n is 0, 1, or 2.

Further provided herein is a compound of Formula III:

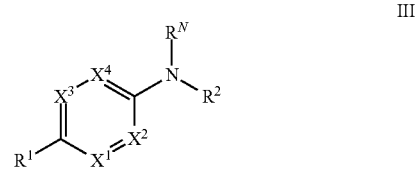

III or a pharmaceutically acceptable salt thereof, wherein:

$X^1$ is CH or N;

$X^2$ is CH or N;

$X^3$ is $CR^3$ or N;

$X^4$ is $CR^4$ or N;

wherein the ring comprising $X^1$, $X^2$, $X^3$, and $X^4$ forms a pyridine ring, a pyrazine ring, or a pyrimidine ring;

$R^N$ is selected from the group consisting of H, $C_{1-6}$ alkyl, and $C(O)R^{N1}$;

$R^{N1}$ is a $C_{6-10}$ aryl which is optionally substituted by 1, 2, 3, or 4 independently selected halo groups;

$R^1$ is selected from the group consisting of 6-10 membered aryl and 5-10 membered heteroaryl, each of which is optionally substituted by 1, 2, 3, or 4 independently selected $R^A$ groups;

$R^2$ is —$(CHR^E)_nR^5$;

$R^5$ is selected from the group consisting of $NR^CR^D$, $C(O)NR^CR^D$, $C(O)OR^C$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^dNR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, $R^N$ is selected from the group consisting of H, $C_{1-3}$ alkyl, and C(O)-phenyl.

In some embodiments, $R^1$ is a 5-10 membered heteroaryl which is optionally substituted by 1, 2, 3, or 4 independently selected $R^A$ groups. For example, R is an unsubstituted 5-6 membered heteroaryl. In some embodiments, $R^1$ is unsubstituted pyridyl.

In some embodiments, $R^2$ is —$(CH_2)_nR^5$.

In some embodiments, $R^3$ is H.

In some embodiments, $R^4$ is H.

In some embodiments, $R^5$ is selected from the group consisting of $NR^CR^D$, $C_{6-10}$ aryl, 4-10 membered heterocycloalkyl, and 5-10 membered heteroaryl, wherein the $C_{6-10}$ aryl, 4-10 membered heterocycloalkyl, and 5-10 membered heteroaryl are each optionally substituted by 1, 2, 3, or 4 independently selected $R^B$ groups. For example, $R^5$ is selected from the group consisting of $NR^CR^D$, phenyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups. In some embodiments, $R^5$ is selected from the group consisting of $N(C_{1-3}$ alkyl)$_2$, phenyl, 4-6 membered heterocycloalkyl, and 5-6 membered heteroaryl. For example, $R^5$ is selected from the group consisting of $N(CH_3)_2$, phenyl, oxazolyl, piperidinyl, and pyrrolidinyl.

In some embodiments, the ring comprising $X^1$, $X^2$, $X^3$, and $X^4$ forms a pyridine ring. In some embodiments, the ring comprising $X^1$, $X^2$, $X^3$, and $X^4$ forms a pyrazine ring. In some embodiments, the ring comprising $X^1$, $X^2$, $X^3$, and $X^4$ forms a pyrimidine ring.

In some embodiments, the ring comprising $X^1$, $X^2$, $X^3$, and $X^4$ forms a pyridine ring, a pyrazine ring, or a pyrimidine ring; $R^N$ is selected from the group consisting of H, $C_{1-3}$ alkyl, and C(O)-phenyl; $R^1$ is a 5-6 membered heteroaryl which is optionally substituted by 1 or 2 independently selected $R^A$ groups; $R^2$ is —$(CH_2)_nR$; $R^3$ is H; $R^4$ is H; $R^5$ is selected from the group consisting of $NR^CR^D$, $C_{6-10}$ aryl, 4-10 membered heterocycloalkyl, and 5-10 membered heteroaryl, wherein the $C_{6-10}$ aryl, 4-10 membered heterocycloalkyl, and 5-10 membered heteroaryl are each optionally substituted by 1, 2, 3, or 4 independently selected $R^B$ groups; and n is 1, 2, or 3.

In some embodiments, the ring comprising $X^1$, $X^2$, $X^3$, and $X^4$ forms a pyridine ring, a pyrazine ring, or a pyrimidine ring; $R^N$ is selected from the group consisting of H, $C_{1-3}$ alkyl, and C(O)-phenyl; $R^1$ is an unsubstituted 5-6 membered heteroaryl; $R^2$ is —$(CH_2)_nR^5$; $R^3$ is H; $R^4$ is H; $R^5$ is selected from the group consisting of $NR^CR^D$, phenyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups; and n is 1, 2, or 3.

In some embodiments, the ring comprising $X^1$, $X^2$, $X^3$, and $X^4$ forms a pyridine ring, a pyrazine ring, or a pyrimidine ring; $R^N$ is selected from the group consisting of H, $C_{1-3}$ alkyl, and C(O)-phenyl; $R^1$ is unsubstituted pyridyl; $R^2$ is —$(CH_2)_nR^5$; $R^3$ is H; $R^4$ is H; $R^5$ is selected from the group consisting of $N(C_{1-3}$ alkyl)$_2$, phenyl, 4-6 membered heterocycloalkyl, and 5-6 membered heteroaryl; and n is 1, 2, or 3.

This disclosure also provides a pharmaceutical composition comprising a compound as described herein, or a pharmaceutically acceptable salt thereof, and a pharmaceutically acceptable excipient.

Also provided herein is a method for treating or preventing glutamate excitotoxicity in a subject in need thereof, the method comprising administering to the subject an effective amount of a compound provided herein, or a pharmaceutically acceptable salt thereof.

Further provided herein is a method for increasing EAAT2 protein expression in a cell or a subject in need thereof, the method comprising contacting the cell or administering to the subject an effective amount of a compound provided herein, or a pharmaceutically acceptable salt thereof.

This disclosure provides a method for activating the NRF2 pathway in a cell or a subject in need thereof, the method comprising contacting the cell or administering to the subject an effective amount of a compound provided herein, or a pharmaceutically acceptable salt thereof.

Also provided herein a method for treating a disease or disorder selected from the group consisting of ischemic stroke, epilepsy, or a trauma, including blunt trauma, an abrasion, an avulsion, an incision, a laceration, a puncture, a penetration, a surgical trauma, iatrogenic trauma, a spinal cord injury, a traumatic brain injury, or any combination thereof; a chronic neurodegenerative disorder, including mild cognitive impairment, Parkinson's disease, Alzheimer's disease, multiple sclerosis, mesial temporal sclerosis, Huntington's disease, AIDS dementia complex, or amyotrophic lateral sclerosis (ALS); a psychotic disorder including schizophrenia, bipolar disorder, or autism; a pain disorder including migraine, temporomandibular disorders, neuropathic pain, visceral pain, or complex regional pain syndrome; an addiction including alcohol addiction, cocaine addiction, heroin addiction, methamphetamine addiction, or nicotine addiction; or a cancer, including glioblastoma; or a mood disorder, including anxiety disorders, depressive disorders, borderline personality disorder, attention-deficit-hyperactivity disorder, suicidal behavior, eating disorders, posttraumatic stress disorder, gulf war illness, and obsessive-Compulsive Disorder in a subject in need thereof, the method comprising administering to the subject an effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

The compounds provided herein may be useful for activating EAAT2, and thus useful in methods of reducing extracellular glutamate levels, thereby reducing glutamate excitotoxicity in cells and tissues, making the compounds therapeutically useful in treating or preventing conditions associated with glutamate excitotoxicity, e.g., acute neurological conditions such as ischemic stroke, epilepsy, and trauma, as well as chronic adult-onset neurodegenerative disorders such as Alzheimer's disease and amyotrophic lateral sclerosis (ALS). In some embodiments, the compounds provided herein may be therapeutically useful in treating or preventing depression.

Compounds of Formula I

The present application provides compounds of Formula I:

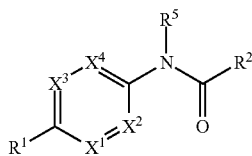

or a pharmaceutically acceptable salt thereof, wherein:
$X^1$ is CH or N;
$X^2$ is CH or N;
$X^3$ is $CR^3$ or N;
$X^4$ is $CR^4$ or N;
wherein the ring comprising $X^1$, $X^2$, $X^3$, and $X^4$ forms a pyridine ring, a pyrazine ring, or a pyrimidine ring;
$R^1$ is selected from the group consisting of 6-10 membered aryl and 5-10 membered heteroaryl, each of which is optionally substituted by 1, 2, 3, or 4 independently selected $R^A$ groups;

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;
$R^3$, $R^4$, and $R^5$ are each independently selected from H and $C_{1-6}$ alkyl;
each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cNR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$;
wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;
each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;
each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and
each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is a $C_{6-10}$ aryl, which is optionally substituted by 1, 2, 3, or 4 independently selected $R^A$ groups. In some embodiments, $R^1$ is phenyl, which is optionally substituted by 1 or 2 independently selected $R^A$ groups. In some embodiments, $R^1$ is phenyl, which is optionally substituted by 1 or 2 independently selected halo groups. In some embodiments, $R^1$ is 2-fluorophenyl.

In some embodiments, $R^1$ is a 5-10 membered heteroaryl which is optionally substituted by 1, 2, 3, or 4 independently selected $R^A$ groups. In some embodiments, $R^1$ is a 5-6 membered heteroaryl which is optionally substituted by 1 or 2 independently selected $R^A$ groups. In some embodiments, $R^1$ is an unsubstituted 5-6 membered heteroaryl. In some embodiments, $R^1$ is unsubstituted pyridyl. In some embodiments, $R^1$ is 2-pyridyl or 3-pyridyl. In some embodiments, $R^1$ is 2-pyridyl. In some embodiments, $R^1$ is 3-pyridyl.

In some embodiments, $R^2$ is selected from the group consisting of phenyl, 5-6 membered heteroaryl, and 4-6 membered heterocycloalkyl, each of which is optionally substituted by 1, 2, 3, or 4 independently selected $R^B$ groups. In some embodiments, $R^2$ is selected from the group consisting of phenyl, 5-6 membered heteroaryl, and 4-6 membered heterocycloalkyl, each of which is optionally substituted by 1 $R^B$ group. In some embodiments, $R^2$ is selected from the group consisting of phenyl, pyridyl, imidazolyl, thiazolyl, oxazolyl, pyrrolidinyl, and piperidinyl, wherein the phenyl, pyridyl, imidazolyl, thiazolyl, oxazolyl, pyrrolidinyl, and piperidinyl are each optionally substituted with 1 $R^B$ group.

In some embodiments, each $R^B$ is independently selected from the group consisting of halo, $C_{1-6}$ alkyl, and $OR^a$. In some embodiments, each $R^B$ is an independently selected halo group. In some embodiments, each $R^B$ is an independently selected $C_{1-6}$ alkyl group. In some embodiments, each $R^B$ is $OR^a$. In some embodiments, each $R^B$ is an independently selected $C_{1-6}$ alkoxy group. In some embodiments, each $R^B$ is independently selected from the group consisting of $C_{1-3}$ alkyl, F, Cl, and $C_{1-3}$ alkoxy. In some embodiments, each $R^B$ is independently selected from the group consisting of $CH_3$, F, Cl, and $OCH_3$. In some embodiments, each $R^B$ is $CH_3$. In some embodiments, each $R^B$ is F. In some embodiments, each $R^B$ is Cl. In some embodiments, each $R^B$ is $OCH_3$.

In some embodiments, $R^3$ is H.
In some embodiments, $R^4$ is H.
In some embodiments, $R^5$ is H.
In some embodiments, $R^3$ and $R^4$ are each H. In some embodiments, $R^3$ and $R^5$ are each H. In some embodiments, $R^4$ and $R^5$ are each H. In some embodiments, $R^3$, $R^4$, and $R^5$ are each H.

In some embodiments, the ring comprising $X^1$, $X^2$, $X^3$, and $X^4$ forms a pyridine ring.

In some embodiments, the ring comprising $X^1$, $X^2$, $X^3$, and $X^4$ forms a pyrazine ring.

In some embodiments, the ring comprising $X^1$, $X^2$, $X^3$, and $X^4$ forms a pyrimidine ring.

In some embodiments:
the ring comprising $X^1$, $X^2$, $X^3$, and $X^4$ forms a pyridine ring, a pyrazine ring, or a pyrimidine ring;
$R^1$ is a 5-6 membered heteroaryl which is optionally substituted by 1 or 2 independently selected $R^A$ groups;
$R^2$ is selected from the group consisting of phenyl, 5-6 membered heteroaryl, and 4-6 membered heterocycloalkyl, each of which is optionally substituted by 1, 2, 3, or 4 independently selected $R^B$ groups;
each $R^B$ is independently selected from the group consisting of halo, $C_{1-6}$ alkyl, and $OR^a$;
$R^3$ is H;
$R^4$ is H; and
$R^5$ is H.

In some embodiments:
the ring comprising $X^1$, $X^2$, $X^3$, and $X^4$ forms a pyridine ring, a pyrazine ring, or a pyrimidine ring;
$R^1$ is an unsubstituted 5-6 membered heteroaryl;
$R^2$ is selected from the group consisting of phenyl, 5-6 membered heteroaryl, and 4-6 membered heterocycloalkyl, each of which is optionally substituted by 1 or 2 independently selected $R^B$ groups;
each $R^B$ is independently selected from the group consisting of halo, $C_{1-6}$ alkyl, and $OCH_3$;
$R^3$ is H;
$R^4$ is H; and
$R^5$ is H.

In some embodiments:
the ring comprising $X^1$, $X^2$, $X^3$, and $X^4$ forms a pyridine ring, a pyrazine ring, or a pyrimidine ring;
$R^1$ is pyridyl;
$R^2$ is selected from the group consisting of phenyl, 5-6 membered heteroaryl, and 4-6 membered heterocycloalkyl, each of which is optionally substituted by 1 or 2 independently selected $R^B$ groups;

each $R^B$ is independently selected from the group consisting of halo, $C_{1-6}$ alkyl, and $OCH_3$;
$R^3$ is H;
$R^4$ is H; and
$R^5$ is H.

In some embodiments:
the ring comprising $X^1$, $X^2$, $X^3$, and $X^4$ forms a pyridine ring, a pyrazine ring, or a pyrimidine ring;
$R^1$ is pyridyl;
$R^2$ is selected from the group consisting of phenyl, pyridyl, imidazolyl, thiazolyl, oxazolyl, pyrrolidinyl, and piperidinyl, wherein the phenyl, pyridyl, imidazolyl, thiazolyl, oxazolyl, pyrrolidinyl, and piperidinyl are each optionally substituted with 1 $R^B$ group;
each $R^B$ is independently selected from the group consisting of halo, $C_{1-6}$ alkyl, and $OCH_3$;
$R^3$ is H;
$R^4$ is H; and
$R^5$ is H.

In some embodiments, the compound of Formula I is a compound of Formula Ia:

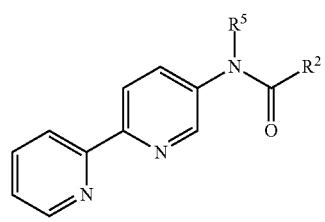

or a pharmaceutically acceptable salt thereof.

In some embodiments, the compound of Formula I is a compound of Formula Ib:

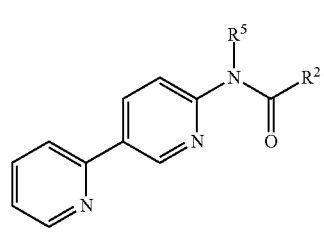

or a pharmaceutically acceptable salt thereof.

In some embodiments, the compound of Formula I is a compound of Formula Ic:

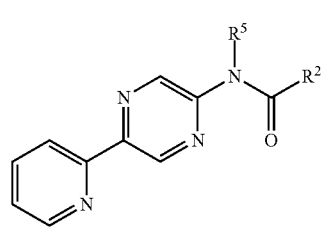

or a pharmaceutically acceptable salt thereof.

In some embodiments, the compound of Formula I is a compound of Formula Id:

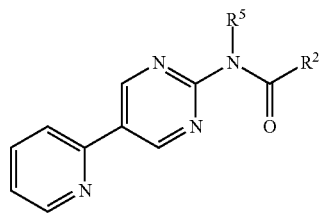
or a pharmaceutically acceptable salt thereof.
In some embodiments, the compound of Formula I is a compound of Formula Ie:
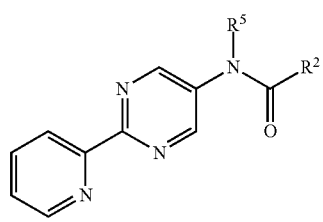
or a pharmaceutically acceptable salt thereof.
In some embodiments, the compound of Formula I is selected from the group consisting of:
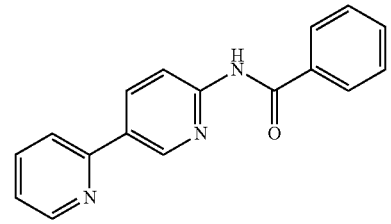
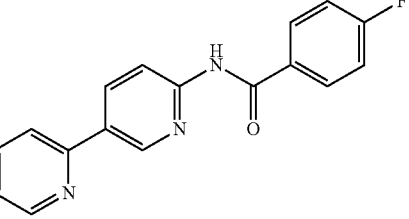
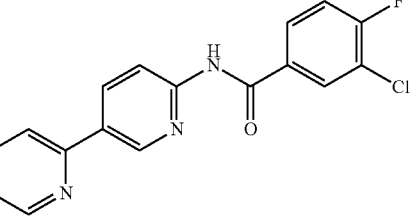
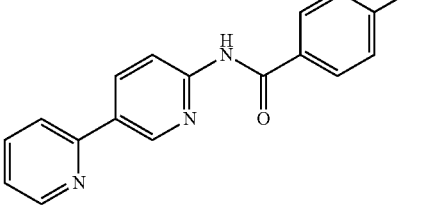
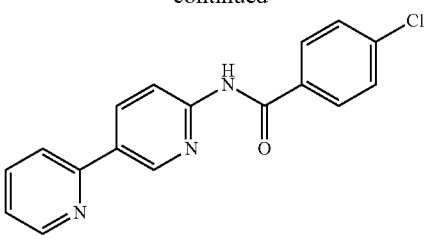
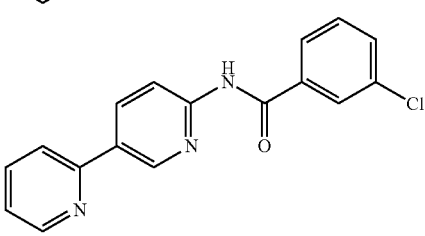
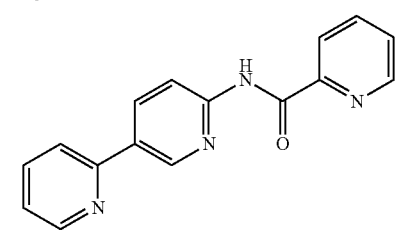
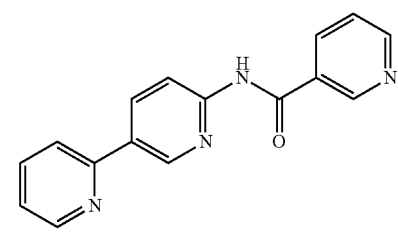
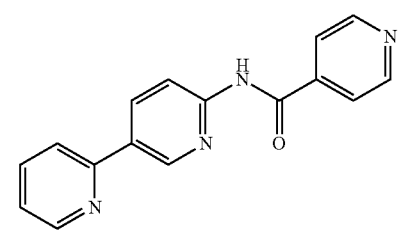 [SMILES: O=C(Nc1ccc(-c2ccccn2)cn1)c1ccncc1]
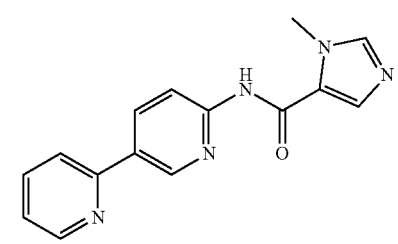
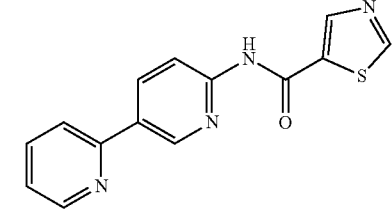 [SMILES: O=C(Nc1ccc(-c2ccccn2)cn1)c1cncs1]

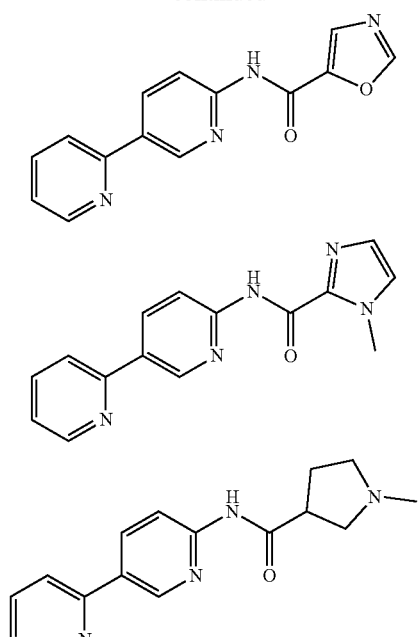
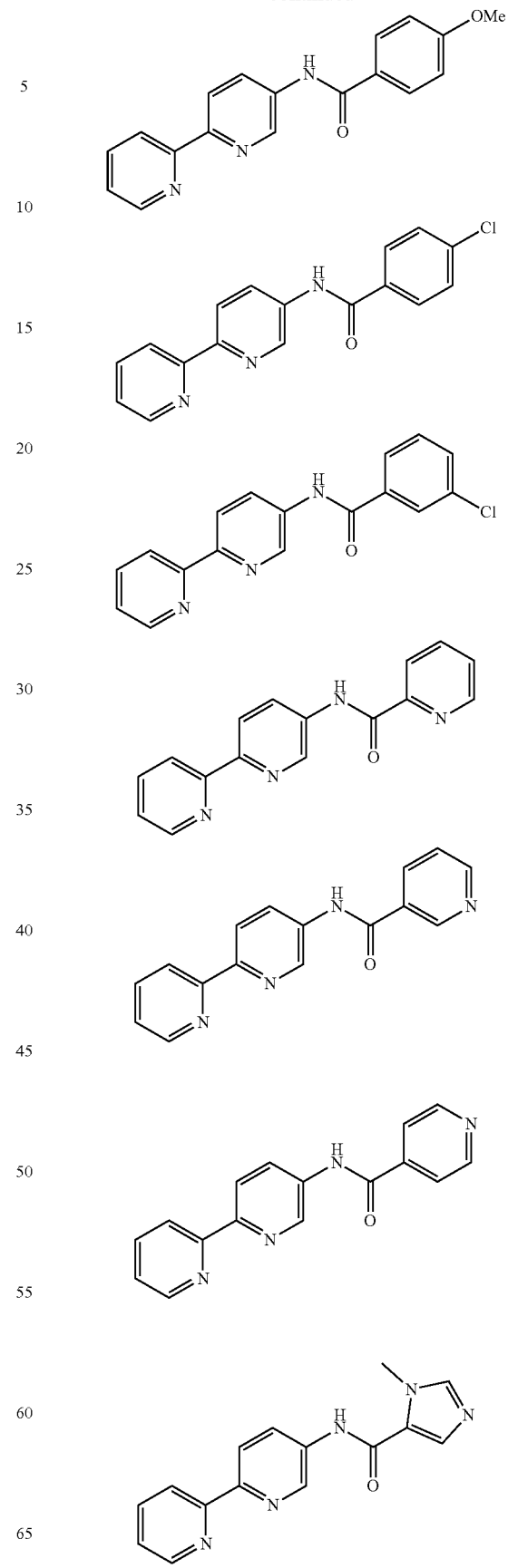

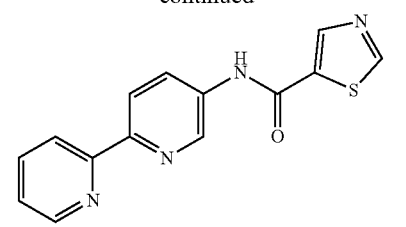
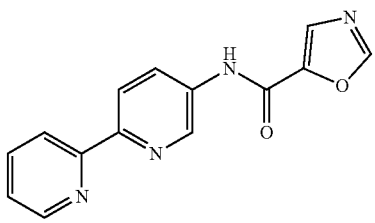 [SMILES: O=C(Nc1ccc(-c2ccccn2)nc1)c1cnco1]
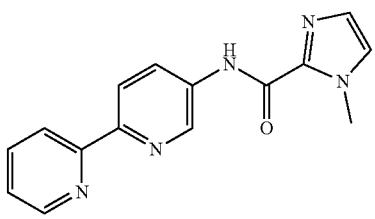 [SMILES: Cn1ccnc1C(=O)Nc1ccc(-c2ccccn2)nc1]
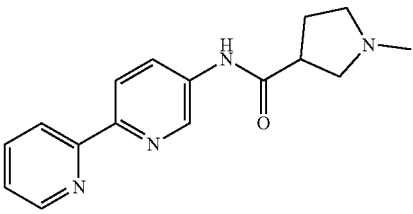 [SMILES: CN1CCC(C(=O)Nc2ccc(-c3ccccn3)nc2)C1]
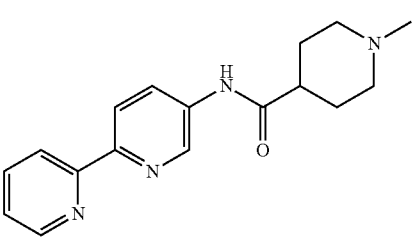 [SMILES: CN1CCC(C(=O)Nc2ccc(-c3ccccn3)nc2)CC1]
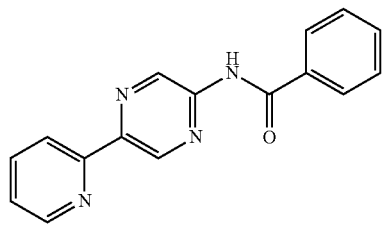
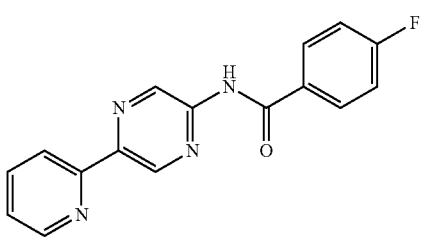 [SMILES: O=C(Nc1cnc(-c2ccccn2)cn1)c1ccc(F)cc1]
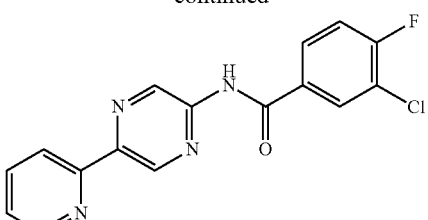
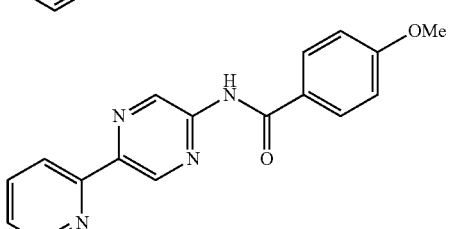
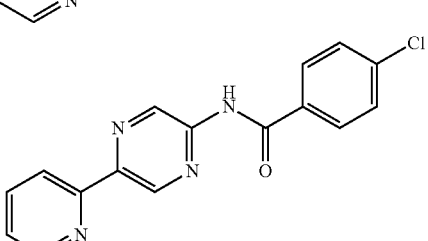
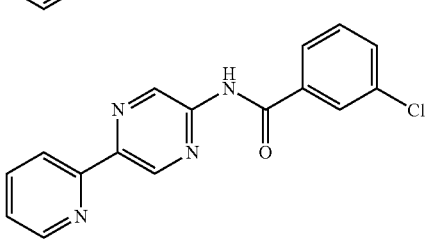
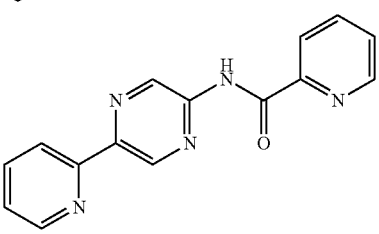
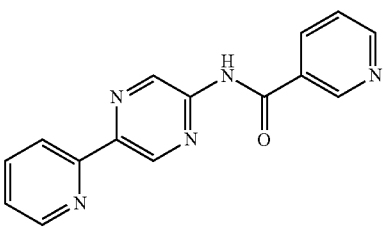
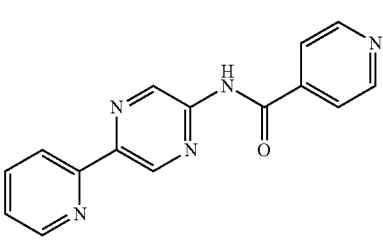 [SMILES: O=C(Nc1cnc(-c2ccccn2)cn1)c1ccncc1]

-continued
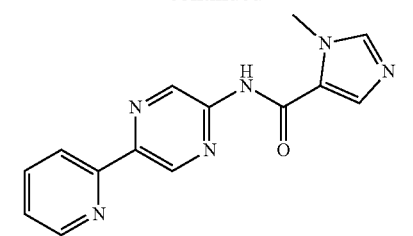 [SMILES: Cn1cncc1C(=O)Nc1cnc(-c2ccccn2)cn1]
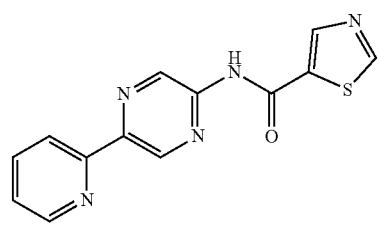 [SMILES: O=C(Nc1cnc(-c2ccccn2)cn1)c1cncs1]
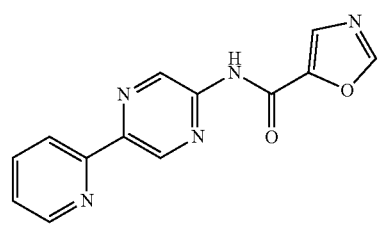 [SMILES: O=C(Nc1cnc(-c2ccccn2)cn1)c1cnco1]
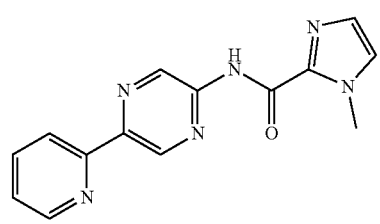 [SMILES: Cn1ccnc1C(=O)Nc1cnc(-c2ccccn2)cn1]
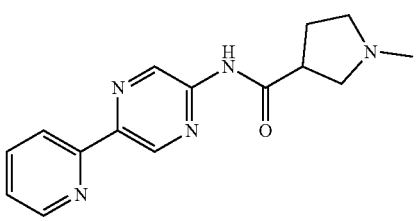 [SMILES: CN1CCC(C(=O)Nc2cnc(-c3ccccn3)cn2)C1]
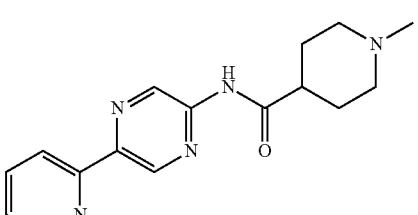
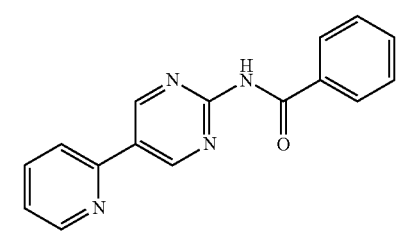 [SMILES: O=C(Nc1ncc(-c2ccccn2)cn1)c1ccccc1]
-continued
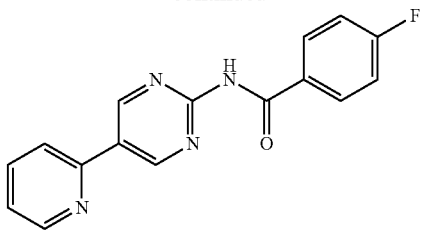 [SMILES: O=C(Nc1ncc(-c2ccccn2)cn1)c1ccc(F)cc1]
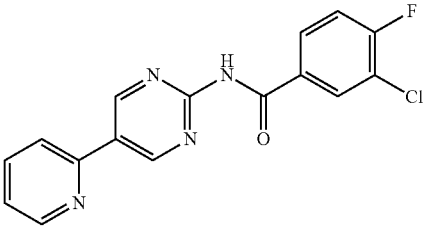
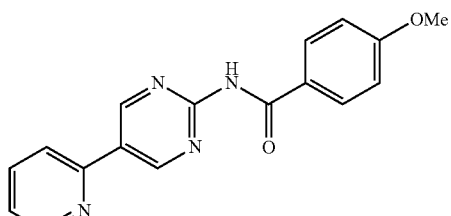
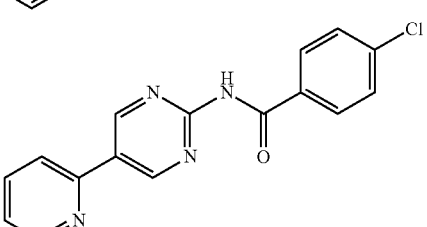
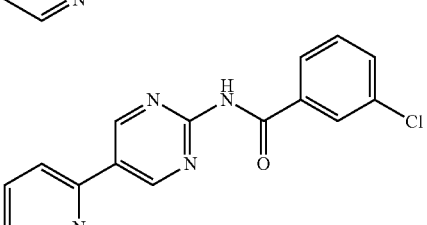
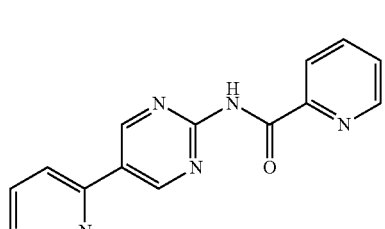
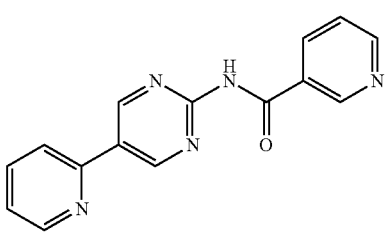 [SMILES: O=C(Nc1ncc(-c2ccccn2)cn1)c1cccnc1]

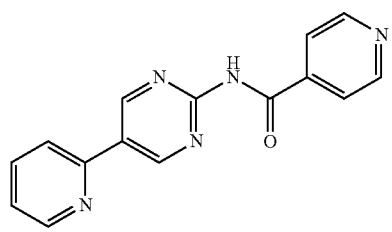
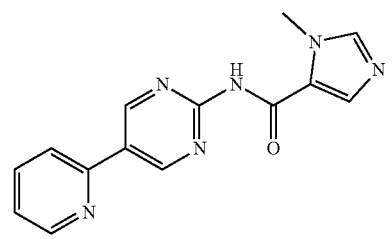 [SMILES: Cn1cncc1C(=O)Nc1ncc(-c2ccccn2)cn1]
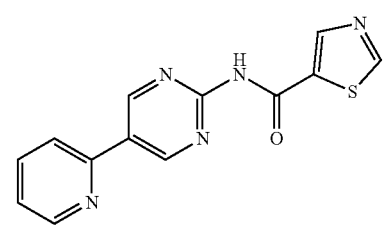 [SMILES: O=C(Nc1ncc(-c2ccccn2)cn1)c1cncs1]
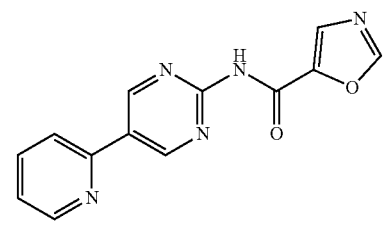 [SMILES: O=C(Nc1ncc(-c2ccccn2)cn1)c1cnco1]
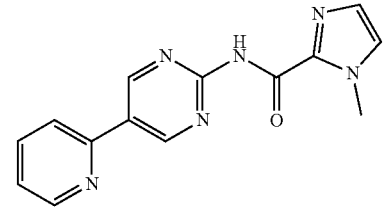 [SMILES: Cn1ccnc1C(=O)Nc1ncc(-c2ccccn2)cn1]
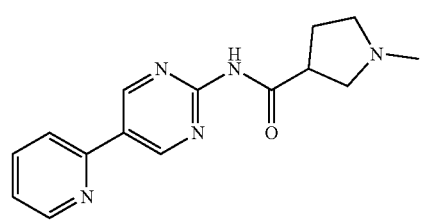 [SMILES: CN1CCC(C(=O)Nc2ncc(-c3ccccn3)cn2)C1]
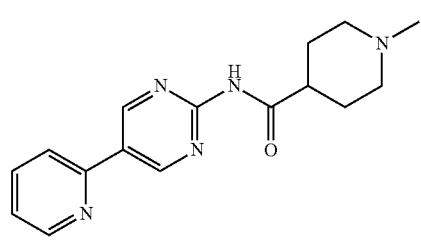 [SMILES: CN1CCC(C(=O)Nc2ncc(-c3ccccn3)cn2)CC1]
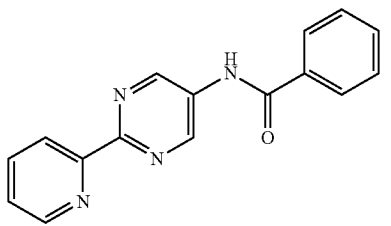
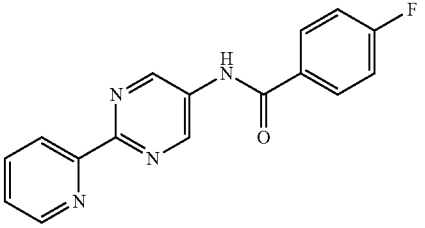 [SMILES: O=C(Nc1cnc(-c2ccccn2)nc1)c1ccc(F)cc1]
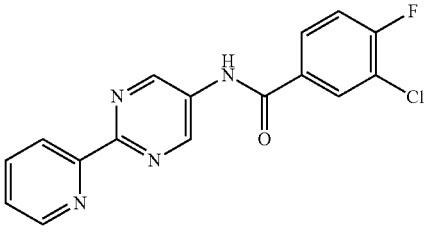
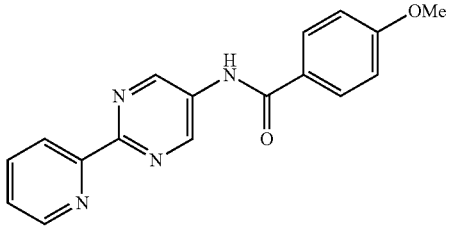 [SMILES: COc1ccc(C(=O)Nc2cnc(-c3ccccn3)nc2)cc1]
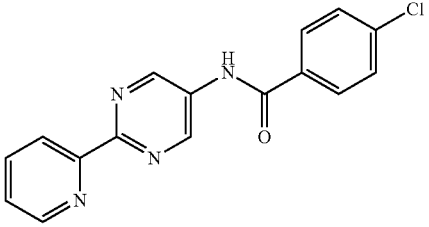 [SMILES: O=C(Nc1cnc(-c2ccccn2)nc1)c1ccc(Cl)cc1]
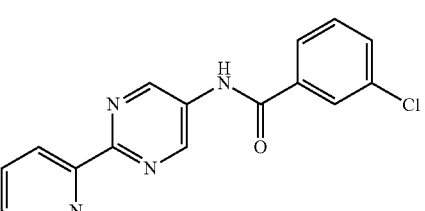
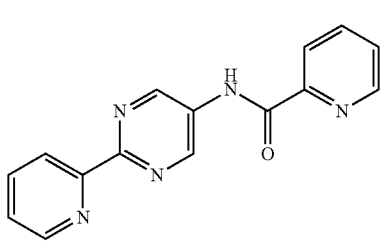

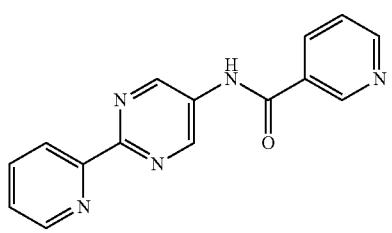 [SMILES: O=C(Nc1cnc(-c2ccccn2)nc1)c1cccnc1]
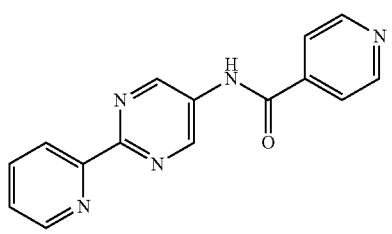 [SMILES: O=C(Nc1cnc(-c2ccccn2)nc1)c1ccncc1]
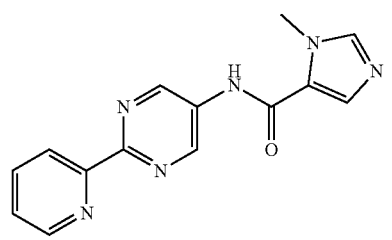 [SMILES: Cn1cncc1C(=O)Nc1cnc(-c2ccccn2)nc1]
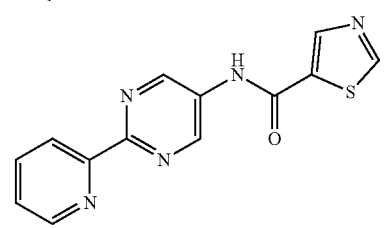
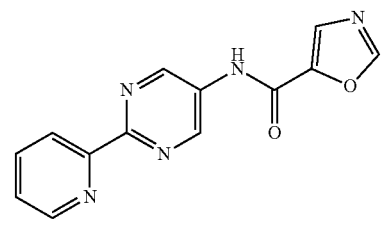 [SMILES: O=C(Nc1cnc(-c2ccccn2)nc1)c1cnco1]
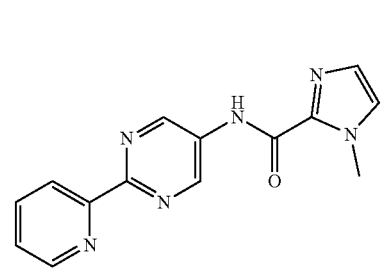 [SMILES: Cn1ccnc1C(=O)Nc1cnc(-c2ccccn2)nc1]
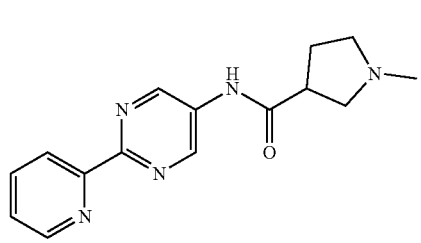 [SMILES: CN1CCC(C(=O)Nc2cnc(-c3ccccn3)nc2)C1]
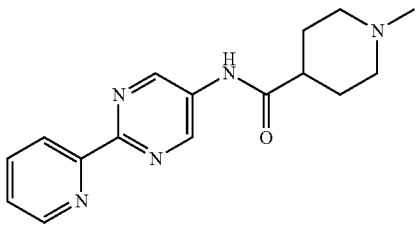 [SMILES: CN1CCC(C(=O)Nc2cnc(-c3ccccn3)nc2)CC1]
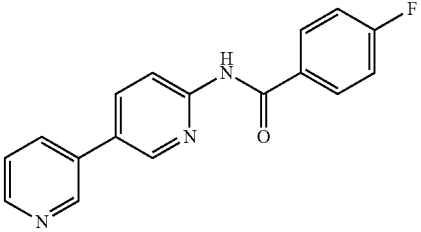 [SMILES: O=C(Nc1ccc(-c2cccnc2)cn1)c1ccc(F)cc1]
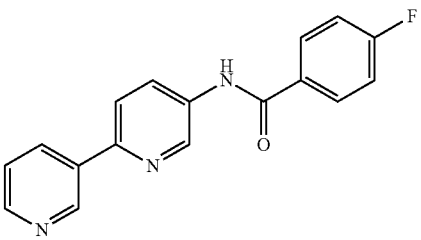 [SMILES: O=C(Nc1ccc(-c2cccnc2)nc1)c1ccc(F)cc1]
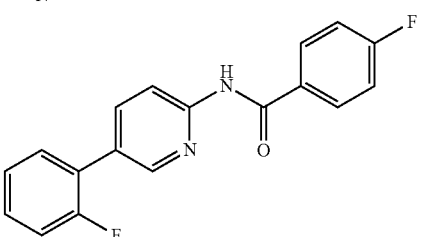
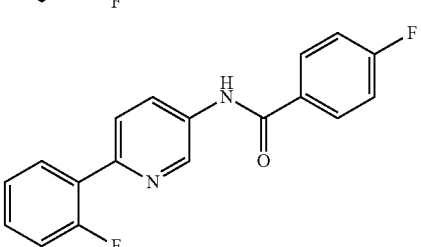
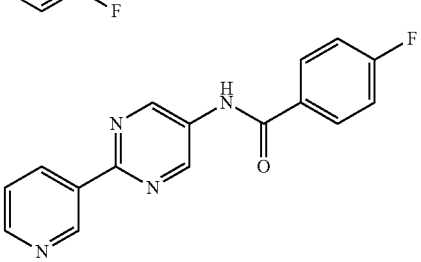

-continued

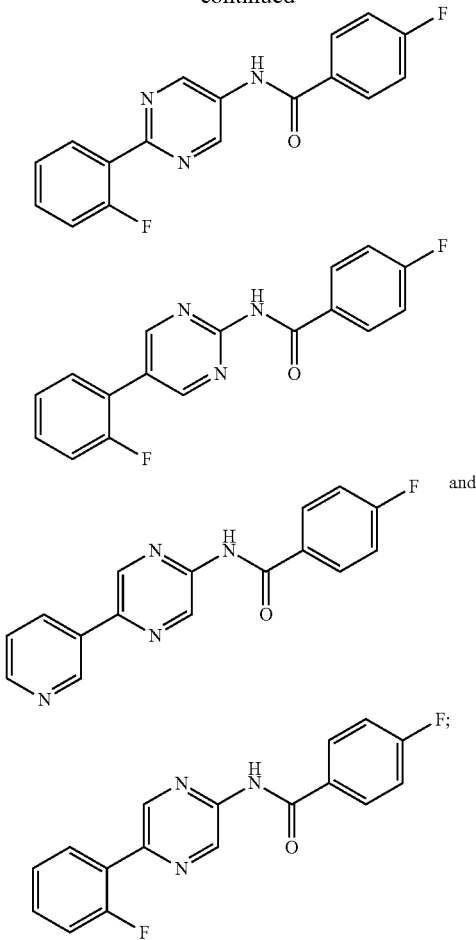

or a pharmaceutically acceptable salt thereof.

Compounds of Formula II

The present application further provides compounds of Formula II:

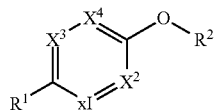

or a pharmaceutically acceptable salt thereof, wherein:
$X^1$ is CH or N;
$X^2$ is CH or N;
$X^3$ is $CR^3$ or N;
$X^4$ is $CR^4$ or N;
wherein the ring comprising $X^1$, $X^2$, $X^3$, and $X^4$ forms a pyridine ring, a pyrazine ring, or a pyrimidine ring;
$R^1$ is selected from the group consisting of 6-10 membered aryl and 5-10 membered heteroaryl, each of which is optionally substituted by 1, 2, 3, or 4 independently selected $R^A$ groups;
$R^2$ is —$(CHR^E)_nR^5$;
$R^5$ is selected from the group consisting of $OR^C$, $NR^CR^D$, $C(O)NR^CR^D$, $C(O)OR^C$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups;

or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_1$-3 alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, $R^1$ is a 5-10 membered heteroaryl which is optionally substituted by 1, 2, 3, or 4 independently selected $R^A$ groups. In some embodiments, $R^1$ is a 5-6 membered heteroaryl which is optionally substituted by 1 or 2 independently selected $R^A$ groups. In some embodiments, $R^1$ is an unsubstituted 5-6 membered heteroaryl. In some embodiments, $R^1$ is unsubstituted pyridyl. In some embodiments, $R^1$ is 2-pyridyl.

In some embodiments, $R^2$ is selected from the group consisting of —$(CH_2)_nR^5$, —$(CH(CH_3))_nR^5$, and —$(CH_2CH(NH_2))_nR^5$. In some embodiments, $R^2$ is —$(CH_2)_nR^5$. In some embodiments, $R^2$ is —$(CH(CH_3))_nR^5$. In some embodiments, $R^2$ is —$(CH_2CH(NH_2))_nR^5$. In some embodiments, n is 0, 1 or 2. In some embodiments, n is 0. In some embodiments, n is 1. In some embodiments, n is 2.

In some embodiments, $R^3$ is H.

In some embodiments, $R^4$ is H.

In some embodiments, $R^3$ and $R^4$ are each H.

In some embodiments, $R^5$ is selected from the group consisting of $OR^C$, $NR^CR^D$, $C(O)NR^CR^D$, $C_{6-10}$ aryl, $C_{3-10}$ cycloalkyl, 4-10 membered heterocycloalkyl, and 5-10 membered heteroaryl, wherein the $C_{6-10}$ aryl, $C_{3-10}$ cycloalkyl, 4-10 membered heterocycloalkyl, and 5-10 membered heteroaryl are each optionally substituted by 1, 2, 3, or 4 independently selected $R^B$ groups.

In some embodiments, $R^5$ is selected from the group consisting of $OR^C$, $NR^CR^D$, $C(O)NR^CR^D$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups.

In some embodiments, $R^5$ is selected from the group consisting of $OCH_3$, $N(CH_3)_2$, $C(O)NH_2$, $C(O)NHCH_3$, $C(O)N(CH_3)_2$, $C(O)N(CH_2CH_3)_2$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups.

In some embodiments, $R^5$ is selected from the group consisting of $OCH_3$, $N(CH_3)_2$, $C(O)NH_2$, $C(O)NHCH_3$, $C(O)N(CH_3)_2$, $C(O)N(CH_2CH_3)_2$, phenyl, cyclopentyl, cyclohexyl, oxazolyl, pyridyl, thiazolyl, imidazolyl, pyrazolyl, piperidinyl, piperidinonyl, pyrrolidinyl, pyrrolidinonyl, benzoimidazolyl, and quinolinyl, wherein the phenyl, cyclopentyl, cyclohexyl, oxazolyl, pyridyl, thiazolyl, imidazolyl, pyrazolyl, piperidinyl, piperidinonyl, pyrrolidinyl, pyrrolidinonyl, benzoimidazolyl, and quinolinyl are each optionally substituted by 1 or 2 independently selected $R^B$ groups.

In some embodiments, each $R^B$ is independently selected from the group consisting of $C_{1-6}$ alkyl and $NR^cR^d$. In some embodiments, each $R^B$ is independently selected from the group consisting of $C_{1-3}$ alkyl and $N(C_{1-3}$ alkyl$)_2$. In some embodiments, each $R^B$ is independently selected from the group consisting of $CH_3$ and $N(CH_3)_2$.

In some embodiments, the ring comprising $X^1$, $X^2$, $X^3$, and $X^4$ forms a pyridine ring.

In some embodiments, the ring comprising $X^1$, $X^2$, $X^3$, and $X^4$ forms a pyrazine ring.

In some embodiments, the ring comprising $X^1$, $X^2$, $X^3$, and $X^4$ forms a pyrimidine ring.

In some embodiments:
the ring comprising $X^1$, $X^2$, $X^3$, and $X^4$ forms a pyridine ring, a pyrazine ring, or a pyrimidine ring;
$R^1$ is a 5-6 membered heteroaryl which is optionally substituted by 1 or 2 independently selected $R^A$ groups;
$R^2$ is selected from the group consisting of —$(CH_2)_nR^5$, —$(CH(CH_3))_nR^5$, and —$(CH_2CH(NH_2))_nR^5$;
$R^3$ is H;
$R^4$ is H;
$R^5$ is selected from the group consisting of $OR^C$, $NR^CR^D$, $C(O)NR^CR^D$, $C_{6-10}$ aryl, $C_{3-10}$ cycloalkyl, 4-10 membered heterocycloalkyl, and 5-10 membered heteroaryl, wherein the $C_{6-10}$ aryl, $C_{3-10}$ cycloalkyl, 4-10 membered heterocycloalkyl, and 5-10 membered heteroaryl are each optionally substituted by 1, 2, 3, or 4 independently selected $R^B$ groups;
each $R^B$ is independently selected from the group consisting of $C_{1-6}$ alkyl and $NR^cR^d$; and
n is 0, 1, 2, 3, 4, or 5.

In some embodiments:
the ring comprising $X^1$, $X^2$, $X^3$, and $X^4$ forms a pyridine ring, a pyrazine ring, or a pyrimidine ring;
$R^1$ is an unsubstituted 5-6 membered heteroaryl;
$R^2$ is selected from the group consisting of —$(CH_2)_nR^5$, —$(CH(CH_3))_nR^5$, and —$(CH_2CH(NH_2))_nR^5$;
$R^3$ is H;
$R^4$ is H;
$R^5$ is selected from the group consisting of $OR^C$, $NR^CR^D$, $C(O)NR^CR^D$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups;
each $R^B$ is independently selected from the group consisting of $C_{1-6}$ alkyl and $NR^cR^d$; and
n is 0, 1, or 2.

In some embodiments:
the ring comprising $X^1$, $X^2$, $X^3$, and $X^4$ forms a pyridine ring, a pyrazine ring, or a pyrimidine ring;
$R^1$ is pyridyl;
$R^2$ is selected from the group consisting of —$(CH_2)_nR^5$, —$(CH(CH_3))_nR^5$, and —$(CH_2CH(NH_2))_nR^5$;
$R^3$ is H;
$R^4$ is H;
$R^5$ is selected from the group consisting of $OCH_3$, $N(CH_3)_2$, $C(O)N(CH_3)_2$, phenyl, $C_{3-6}$ cycloalkyl, 4-6 membered heterocycloalkyl, and 5-10 membered heteroaryl, wherein the phenyl, 4-6 membered heterocycloalkyl, and 5-10 membered heteroaryl are each optionally substituted by 1 or 2 independently selected $R^B$ groups;
each $R^B$ is independently is selected from the group consisting of $C_{1-3}$ alkyl and $N(C_{1-3}$ alkyl$)_2$; and
n is 0, 1, or 2.

In some embodiments:
the ring comprising $X^1$, $X^2$, $X^3$, and $X^4$ forms a pyridine ring, a pyrazine ring, or a pyrimidine ring;
$R^1$ is pyridyl;
$R^2$ is selected from the group consisting of —$(CH_2)_nR^5$, —$(CH(CH_3))_nR^5$, and —$(CH_2CH(NH_2))_nR^5$;
$R^3$ is H;
$R^4$ is H;
$R^5$ is selected from the group consisting of $OCH_3$, $N(CH_3)_2$, $C(O)N(CH_3)_2$, phenyl, cyclopentyl, cyclohexyl, oxazolyl, pyridyl, thiazolyl, imidazolyl, piperidinyl, piperidinonyl, pyrrolidinyl, pyrrolidinonyl, and quinolinyl, wherein the phenyl, cyclopentyl, cyclohexyl, oxazolyl, pyridyl, thiazolyl, pyrazolyl, piperidinyl, piperidinonyl, pyrrolidinyl, pyrrolidinonyl, and quinolinyl are each optionally substituted by 1 or 2 independently selected $R^B$ groups;
each $R^B$ is independently is selected from the group consisting of $C_{1-3}$ alkyl and $N(C_{1-3}$ alkyl$)_2$; and
n is 0, 1, or 2.

In some embodiments, the compound of Formula II is a compound of Formula IIa:

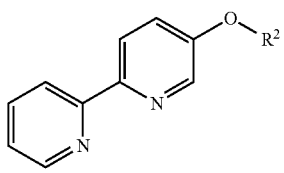

IIa or a pharmaceutically acceptable salt thereof.

In some embodiments, the compound of Formula II is a compound of Formula IIb:

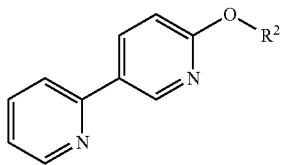

IIb or a pharmaceutically acceptable salt thereof.

In some embodiments, the compound of Formula II is a compound of Formula IIc:

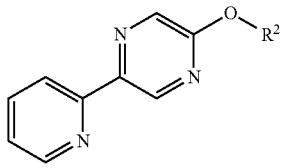

IIc or a pharmaceutically acceptable salt thereof.

In some embodiments, the compound of Formula II is a compound of Formula IId:

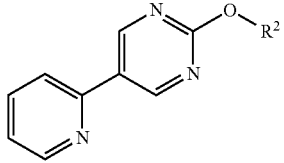

IId or a pharmaceutically acceptable salt thereof.

In some embodiments, the compound of Formula II is a compound of Formula IIe:

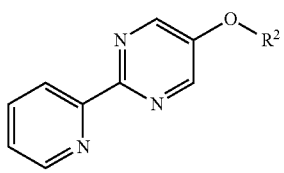

IIe or a pharmaceutically acceptable salt thereof.

In some embodiments, the compound of Formula II is selected from the group consisting of:

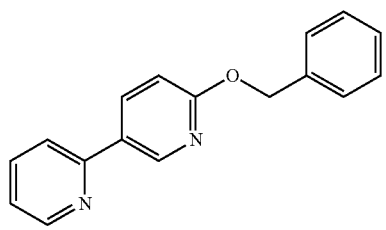

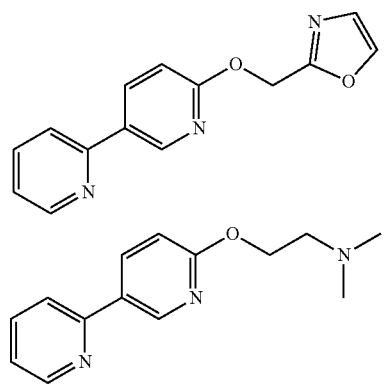

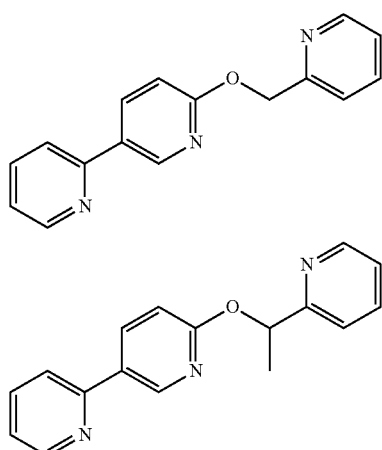

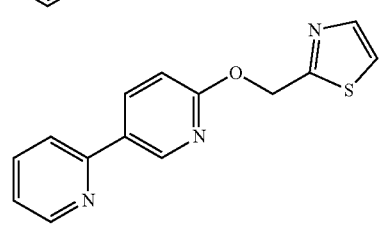

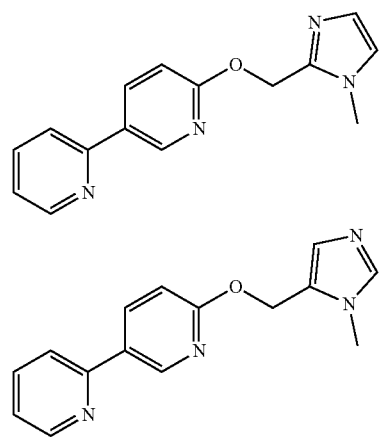

31
-continued
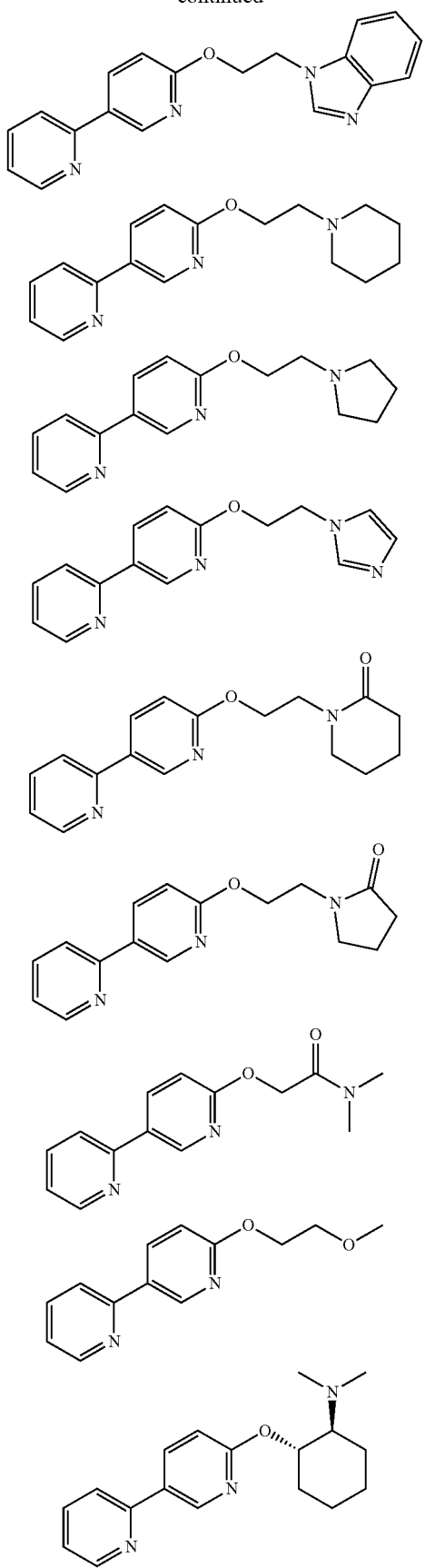
32
-continued
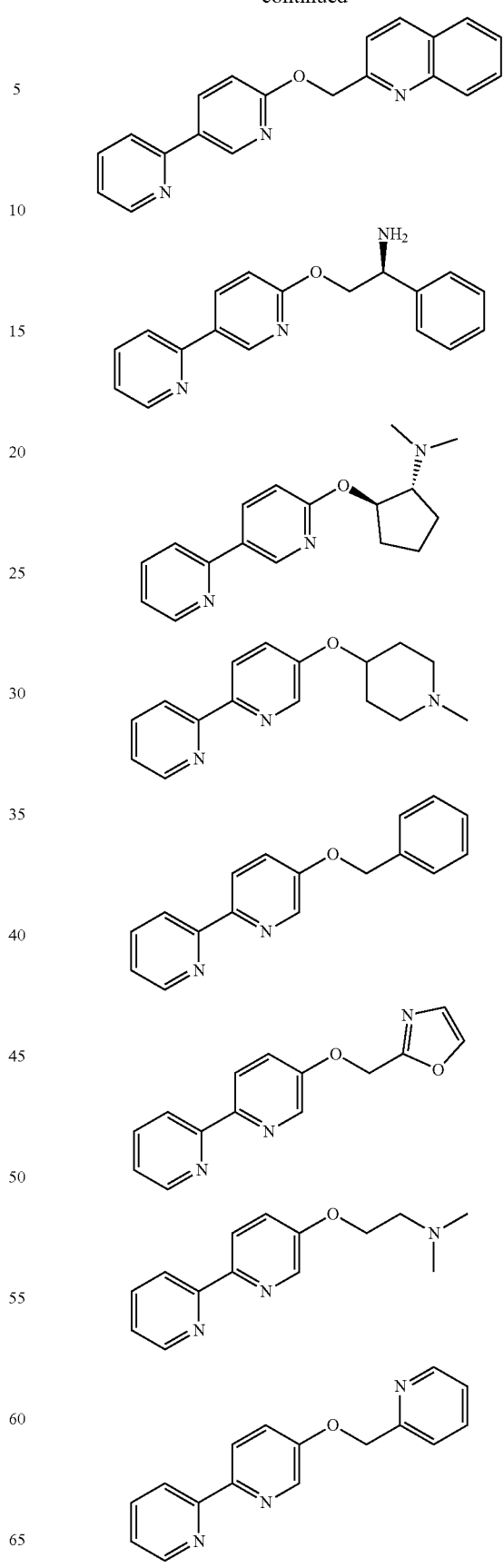

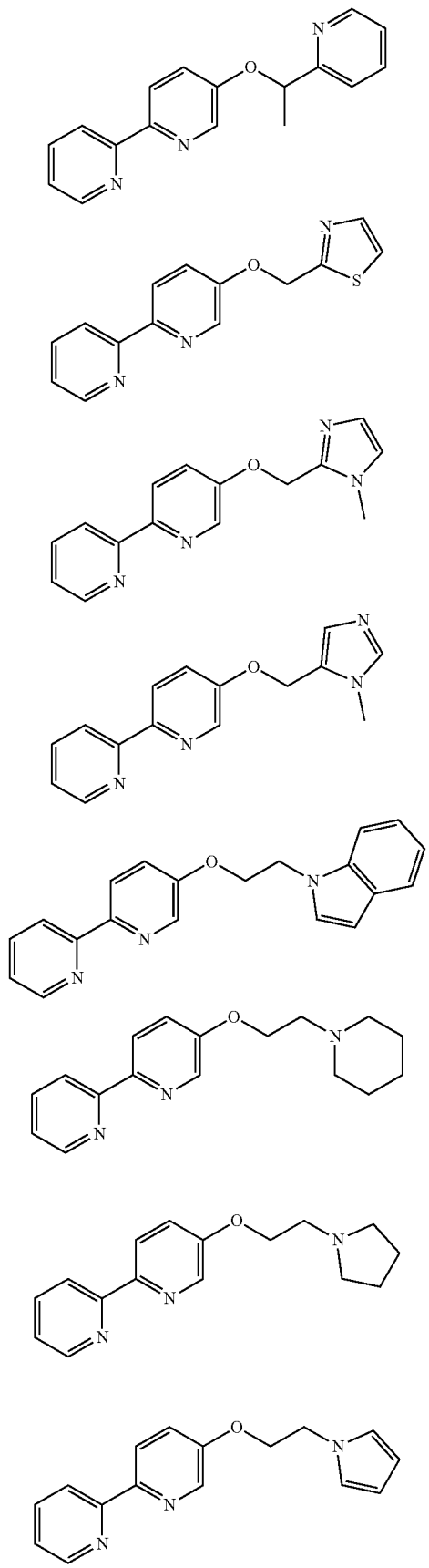
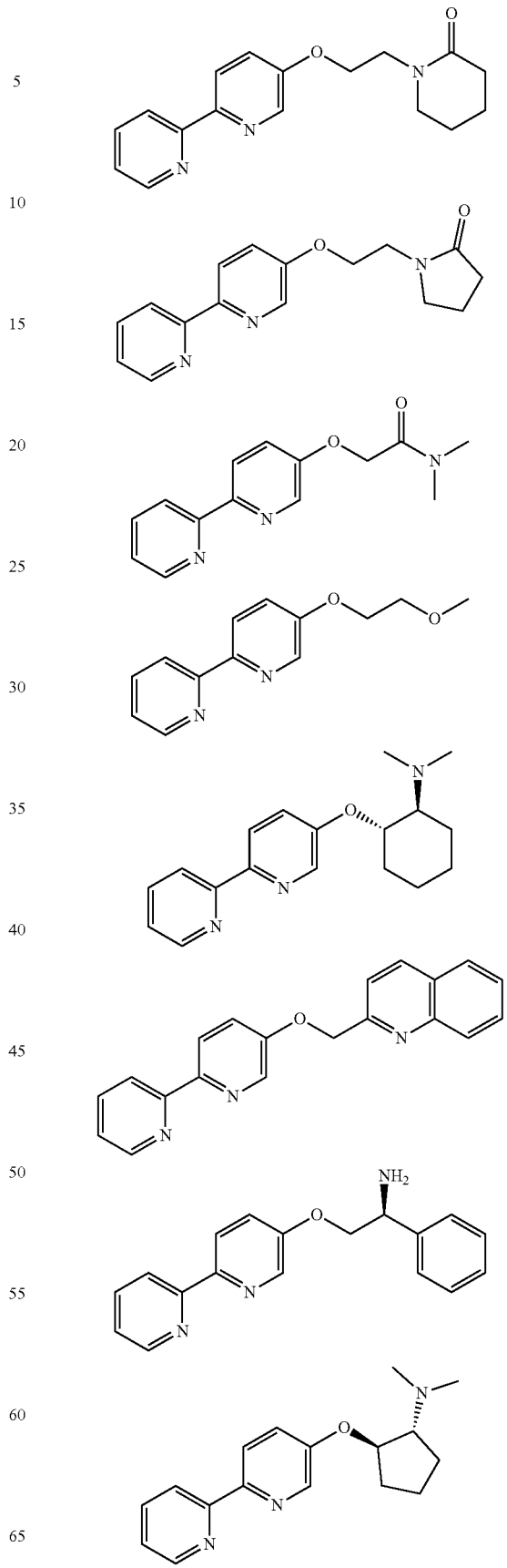

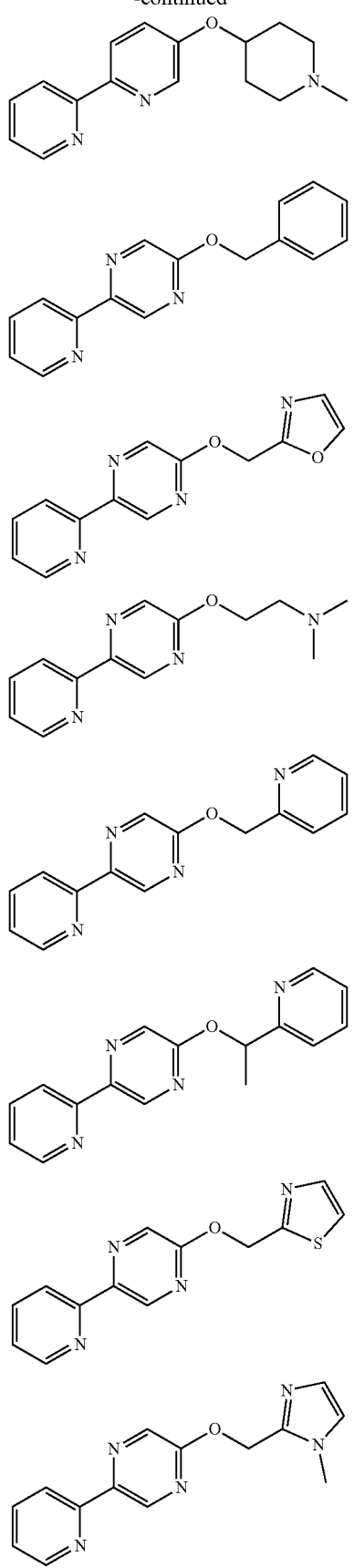
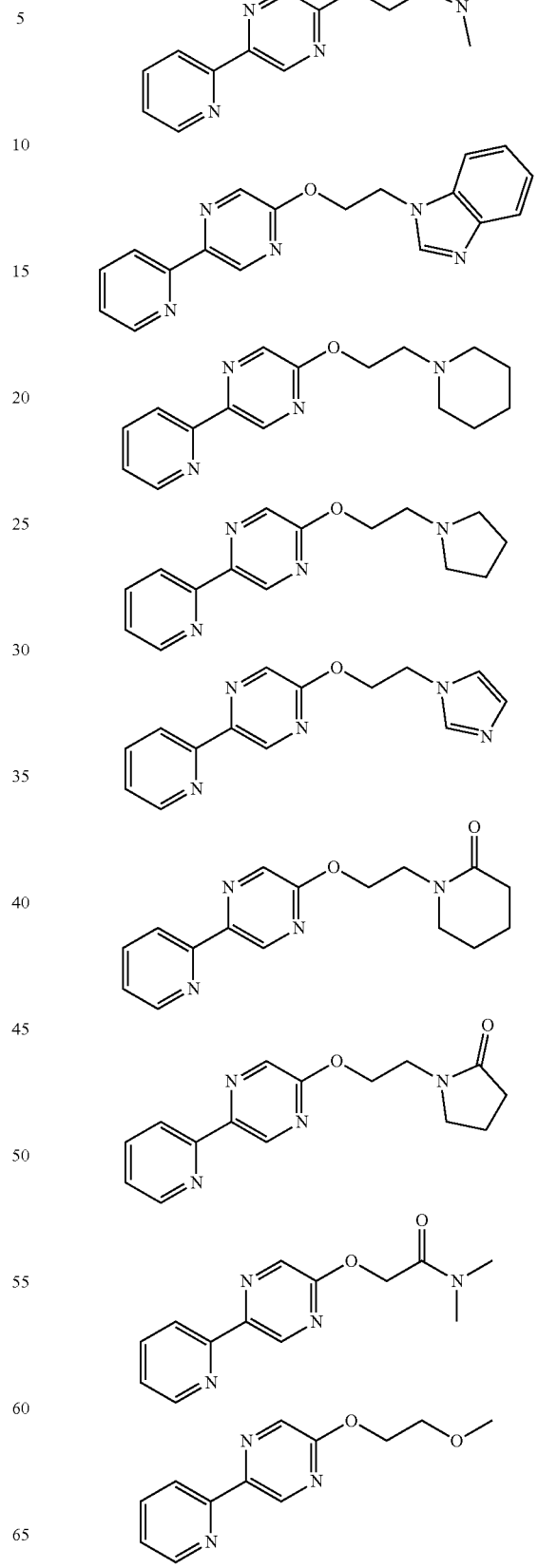

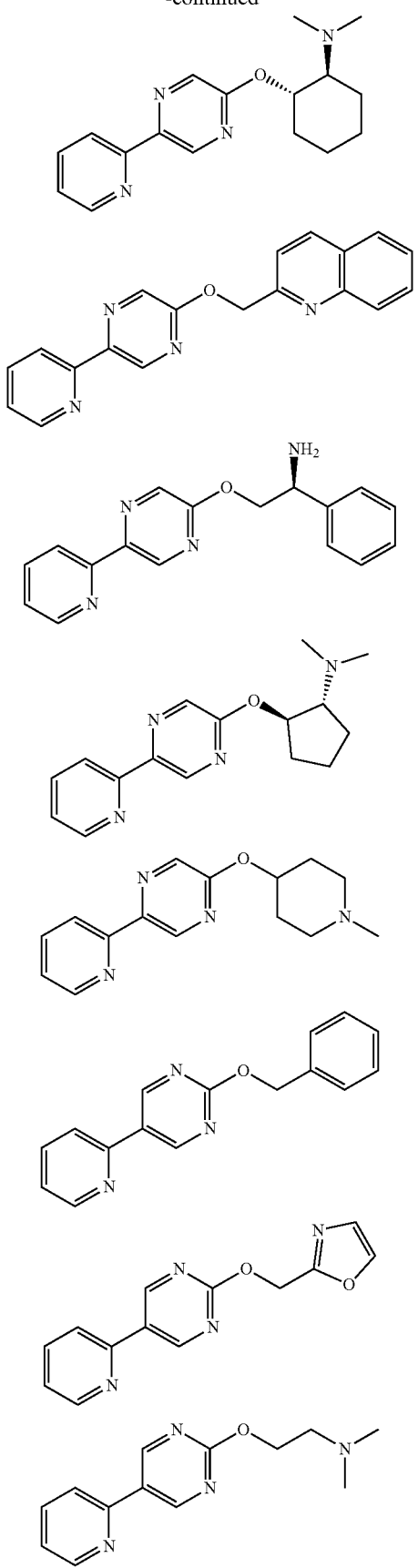
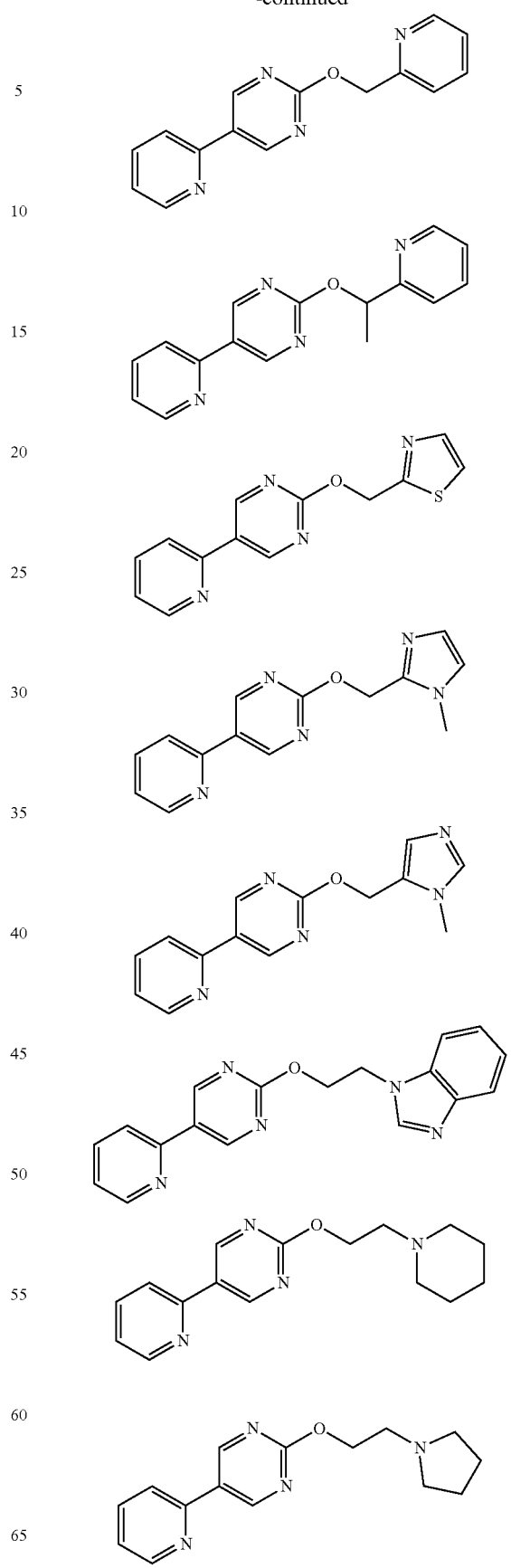

-continued
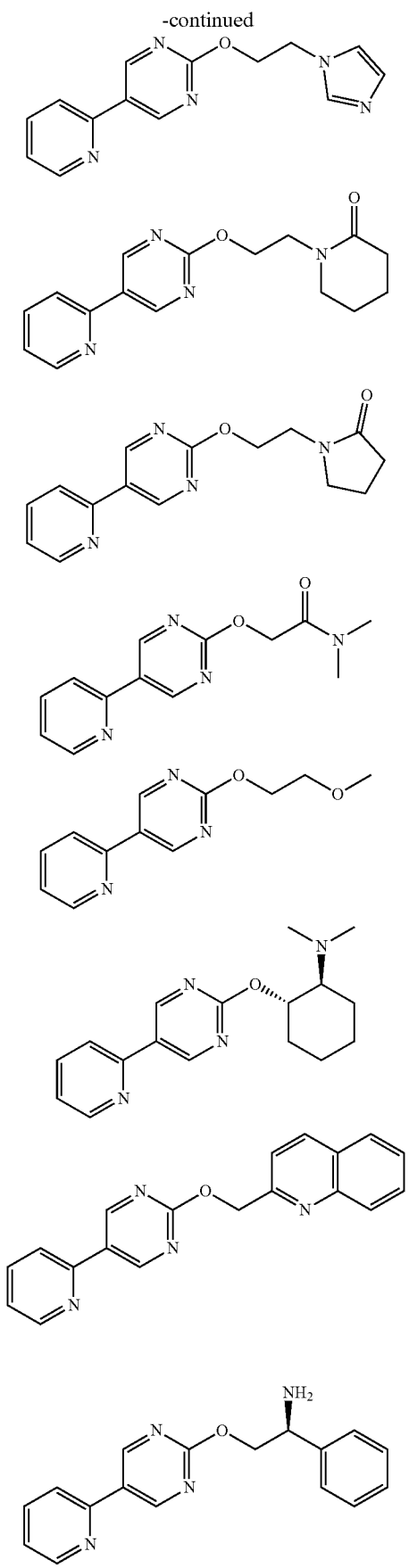
-continued
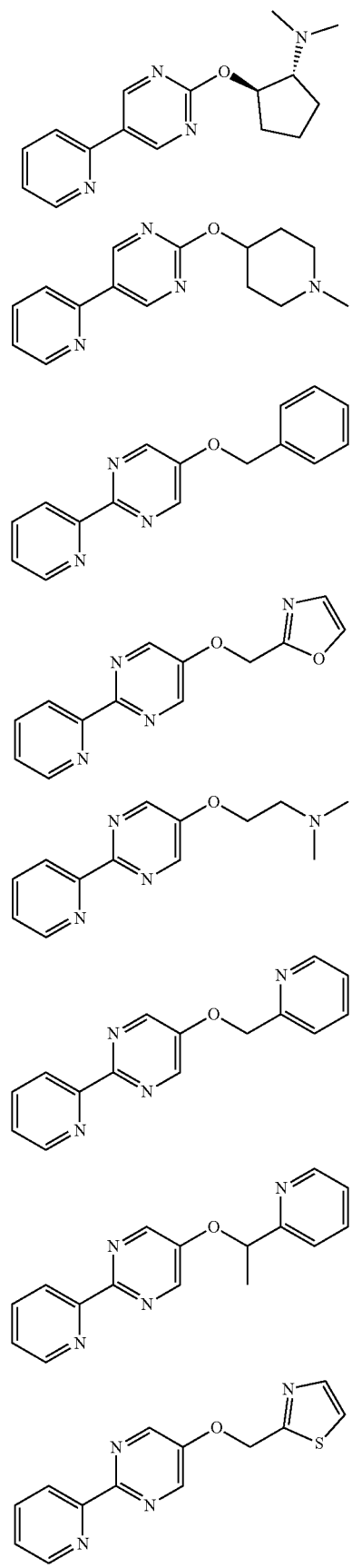

-continued
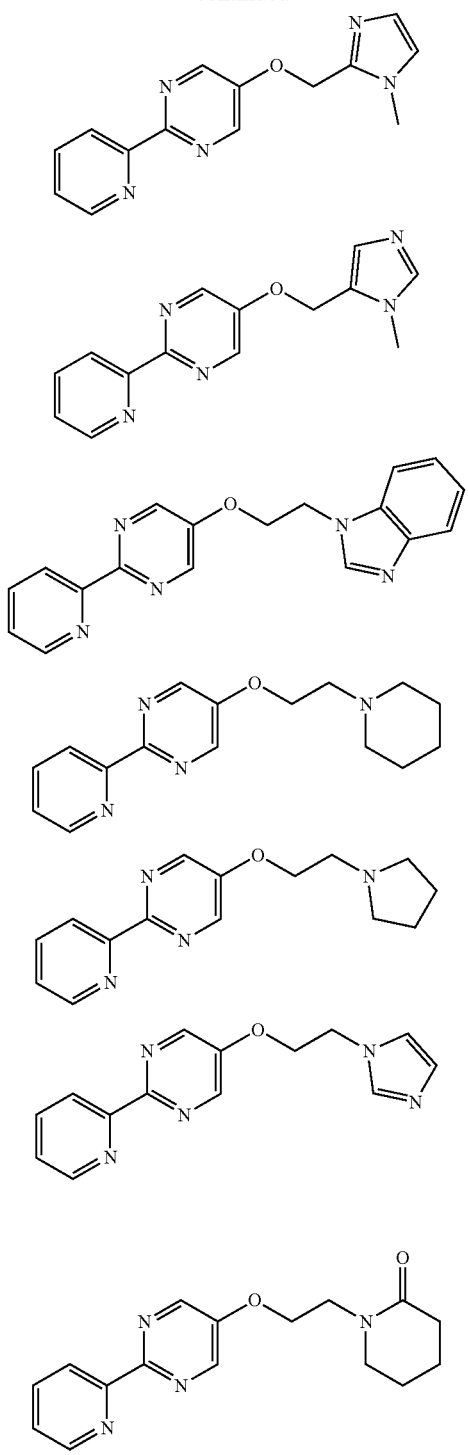
-continued
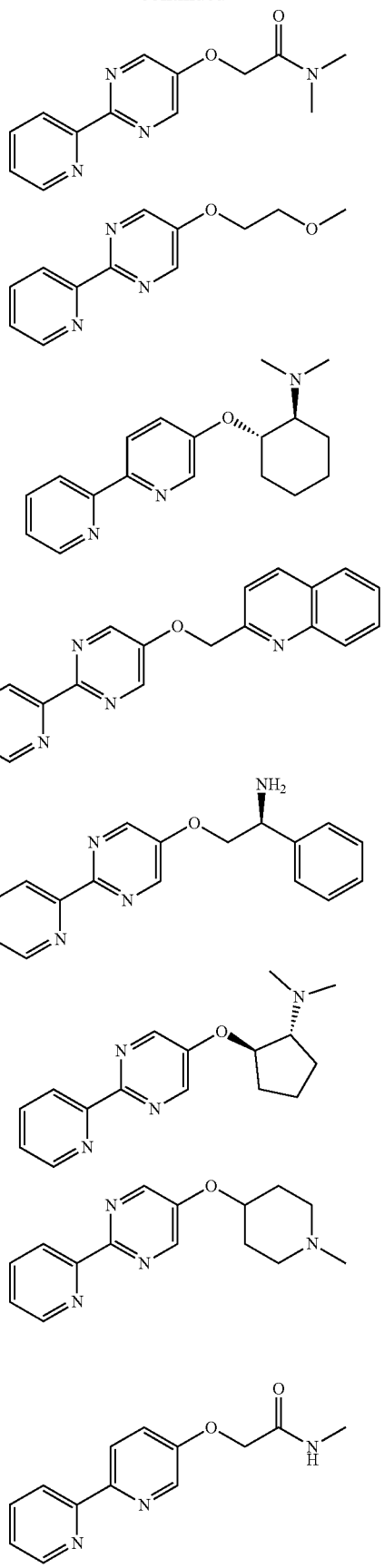

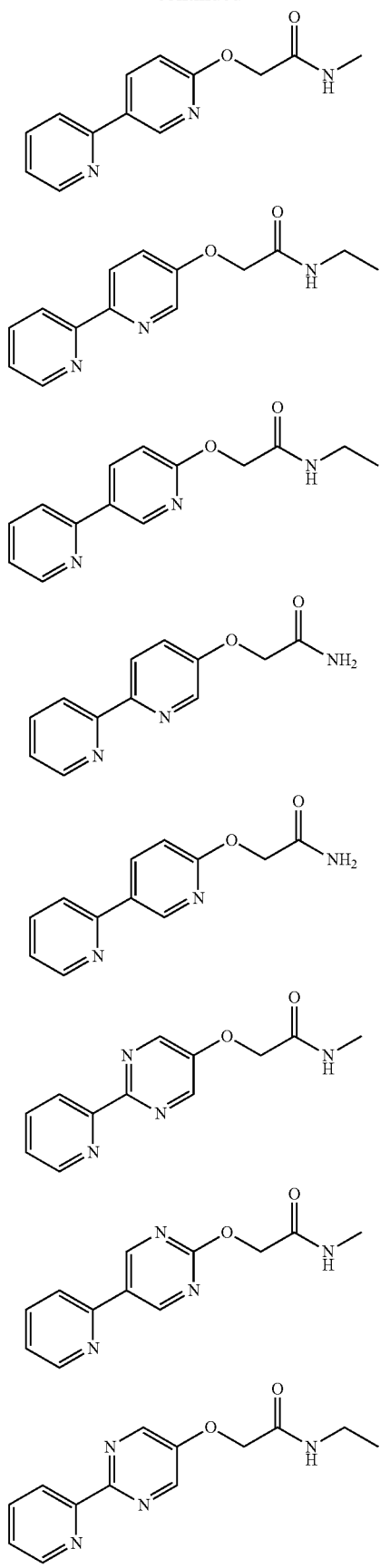
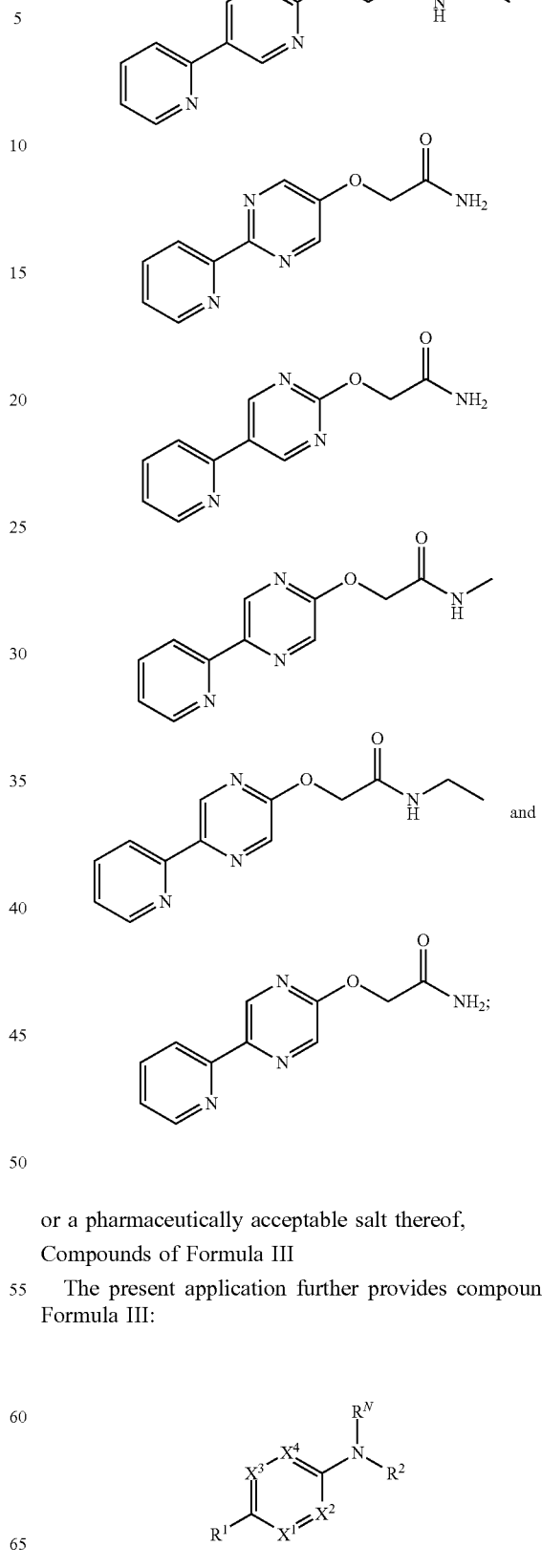
or a pharmaceutically acceptable salt thereof,
Compounds of Formula III
The present application further provides compounds of Formula III:
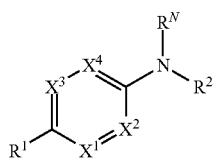

or a pharmaceutically acceptable salt thereof, wherein:

$X^1$ is CH or N;

$X^2$ is CH or N;

$X^3$ is $CR^3$ or N;

$X^4$ is $CR^4$ or N;

wherein the ring comprising $X^1$, $X^2$, $X^3$, and $X^4$ forms a pyridine ring, a pyrazine ring, or a pyrimidine ring;

$R^N$ is selected from the group consisting of H, $C_{1-6}$ alkyl, and $C(O)R^{N_1}$;

$R^{N_1}$ is a $C_{6-10}$ aryl which is optionally substituted by 1, 2, 3, or 4 independently selected halo groups;

$R^1$ is selected from the group consisting of 6-10 membered aryl and 5-10 membered heteroaryl, each of which is optionally substituted by 1, 2, 3, or 4 independently selected $R^A$ groups;

$R^2$ is $-(CHR^E)_nR^5$;

$R^5$ is selected from the group consisting of $NR^CR^D$, $C(O)NR^CR^D$, $C(O)OR^C$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{-s}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, $R^N$ is selected from the group consisting of H, $C_{1-3}$ alkyl, and C(O)-phenyl. In some embodiments, $R^N$ is selected from the group consisting of H, $CH_3$, and C(O)-phenyl. In some embodiments, $R^N$ is H.

In some embodiments, $R^1$ is a 5-10 membered heteroaryl which is optionally substituted by 1, 2, 3, or 4 independently selected $R^A$ groups. In some embodiments, $R^1$ is a 5-6 membered heteroaryl which is optionally substituted by 1 or 2 independently selected $R^A$ groups. In some embodiments, $R^1$ is an unsubstituted 5-6 membered heteroaryl. In some embodiments, $R^1$ is unsubstituted pyridyl. In some embodiments, $R^1$ is 2-pyridyl.

In some embodiments, $R^2$ is $-(CH_2)_nR^5$. In some embodiments, n is 1, 2, or 3. In some embodiments, n is 1. In some embodiments, n is 2. In some embodiments, n is 3.

In some embodiments, $R^3$ is H.

In some embodiments, $R^4$ is H.

In some embodiments, $R^3$ and $R^4$ are each H.

In some embodiments, $R^5$ is selected from the group consisting of $NR^CR^D$, $C_{6-10}$ aryl, 4-10 membered heterocycloalkyl, and 5-10 membered heteroaryl, wherein the $C_{6-10}$ aryl, 4-10 membered heterocycloalkyl, and 5-10 membered heteroaryl are each optionally substituted by 1, 2, 3, or 4 independently selected $R^B$ groups. In some embodiments, $R^5$ is selected from the group consisting of $NR^CR^D$, phenyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups. In some embodiments, $R^5$ is selected from the group consisting of $N(C_{1-3}$ alkyl$)_2$, phenyl, 4-6 membered heterocycloalkyl, and 5-6 membered heteroaryl. In some embodiments, $R^5$ is selected from the group consisting of $N(CH_3)_2$, phenyl, oxazolyl, piperidinyl, and pyrrolidinyl.

In some embodiments:

the ring comprising $X^1$, $X^2$, $X^3$, and $X^4$ forms a pyridine ring, a pyrazine ring, or a pyrimidine ring;

$R^N$ is selected from the group consisting of H, $C_{1-3}$ alkyl, and C(O)-phenyl;

$R^1$ is a 5-6 membered heteroaryl which is optionally substituted by 1 or 2 independently selected $R^A$ groups;

$R^2$ is $-(CH_2)_nR^5$;

$R^3$ is H;

$R^4$ is H;

$R^5$ is selected from the group consisting of $NR^CR^D$, $C_{6-10}$ aryl, 4-10 membered heterocycloalkyl, and 5-10 membered heteroaryl, wherein the $C_{6-10}$ aryl, 4-10 membered heterocycloalkyl, and 5-10 membered heteroaryl are each optionally substituted by 1, 2, 3, or 4 independently selected $R^B$ groups; and n is 1, 2, or 3.

In some embodiments:

the ring comprising $X^1$, $X^2$, $X^3$, and $X^4$ forms a pyridine ring, a pyrazine ring, or a pyrimidine ring;

$R^N$ is selected from the group consisting of H, $C_{1-3}$ alkyl, and C(O)-phenyl;

$R^1$ is an unsubstituted 5-6 membered heteroaryl;

$R^2$ is —$(CH_2)_nR^5$;

$R^3$ is H;

$R^4$ is H;

$R^5$ is selected from the group consisting of $NR^CR^D$, phenyl, 4-6 membered heterocycloalkyl, and 5-6 membered heteroaryl, wherein the phenyl, 4-6 membered heterocycloalkyl, and 5-6 membered heteroaryl are each optionally substituted by 1 or 2 independently selected $R^B$ groups; and n is 1, 2, or 3.

In some embodiments:

the ring comprising $X^1$, $X^2$, $X^3$, and $X^4$ forms a pyridine ring, a pyrazine ring, or a pyrimidine ring;

$R^N$ is selected from the group consisting of H, $C_{1-3}$ alkyl, and C(O)-phenyl;

$R^1$ is pyridyl;

$R^2$ is —$(CH_2)_nR^5$;

$R^3$ is H;

$R^4$ is H;

$R^5$ is selected from the group consisting of $N(C_{1-3}$ alkyl$)_2$, phenyl, 4-6 membered heterocycloalkyl, and 5-6 membered heteroaryl; and n is 1, 2, or 3.

In some embodiments:

the ring comprising $X^1$, $X^2$, $X^3$, and $X^4$ forms a pyridine ring, a pyrazine ring, or a pyrimidine ring;

$R^N$ is selected from the group consisting of H, $C_{1-3}$ alkyl, and C(O)-phenyl;

$R^1$ is pyridyl;

$R^2$ is —$(CH_2)_nR^5$;

$R^3$ is H;

$R^4$ is H;

$R^5$ is selected from the group consisting of $N(CH_3)_2$, phenyl, oxazolyl, piperidinyl, and pyrrolidinyl; and n is 1, 2, or 3.

In some embodiments, the compound of Formula III is a compound of Formula IIIa:

IIIa or a pharmaceutically acceptable salt thereof.

In some embodiments, the compound of Formula III is a compound of Formula IIIb:

IIIb or a pharmaceutically acceptable salt thereof.

In some embodiments, the compound of Formula III is a compound of Formula IIIc:

IIIc or a pharmaceutically acceptable salt thereof.

In some embodiments, the compound of Formula III is a compound of Formula IIId:

IIId or a pharmaceutically acceptable salt thereof.

In some embodiments, the compound of Formula III is a compound of Formula IIIe:

IIIe or a pharmaceutically acceptable salt thereof.

In some embodiments, the compound of Formula III is selected from the group consisting of:

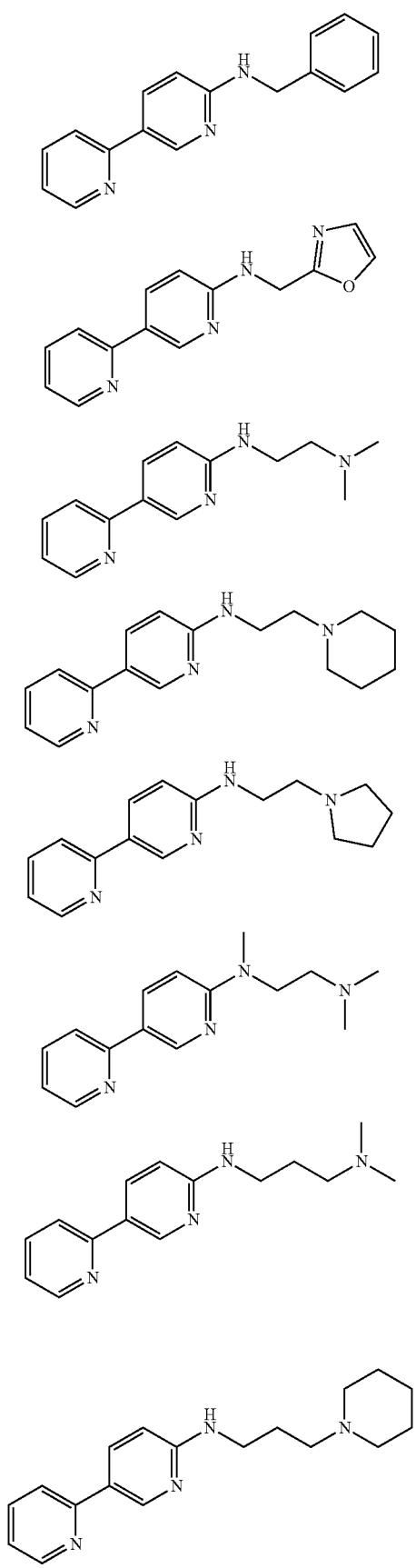
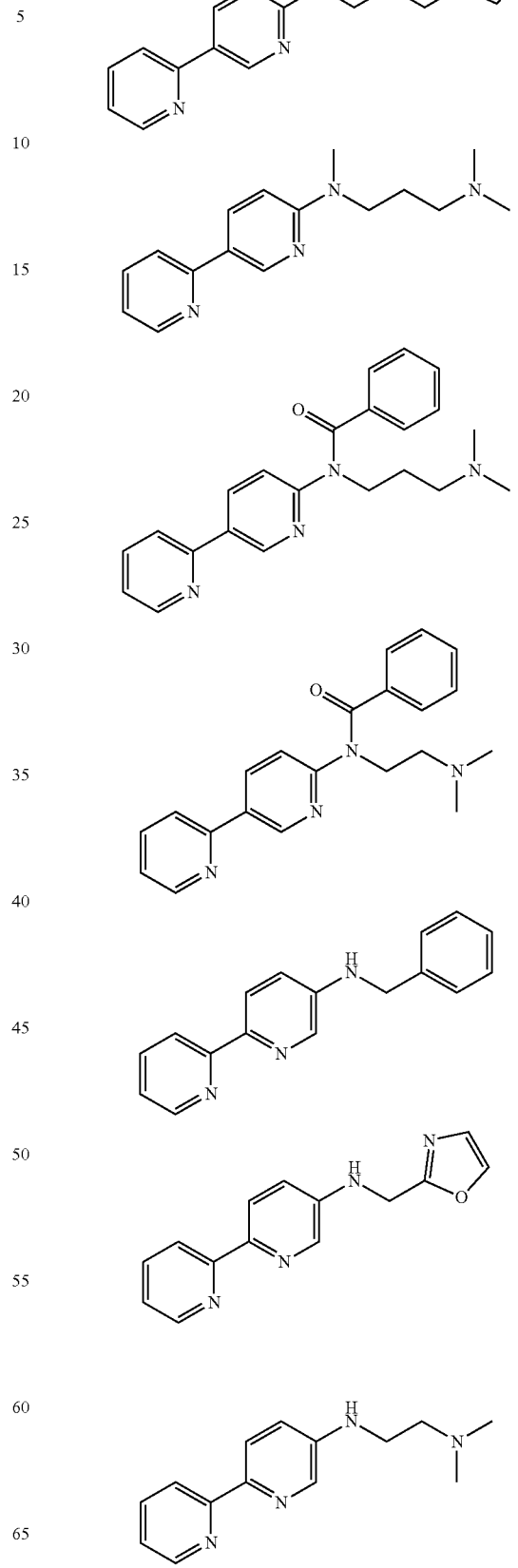

-continued
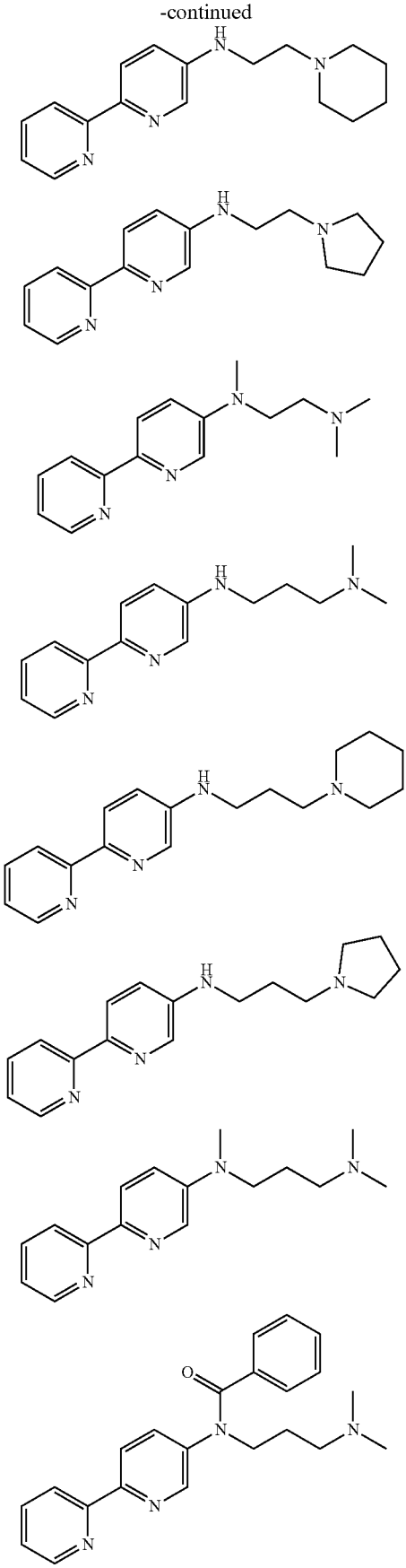
-continued
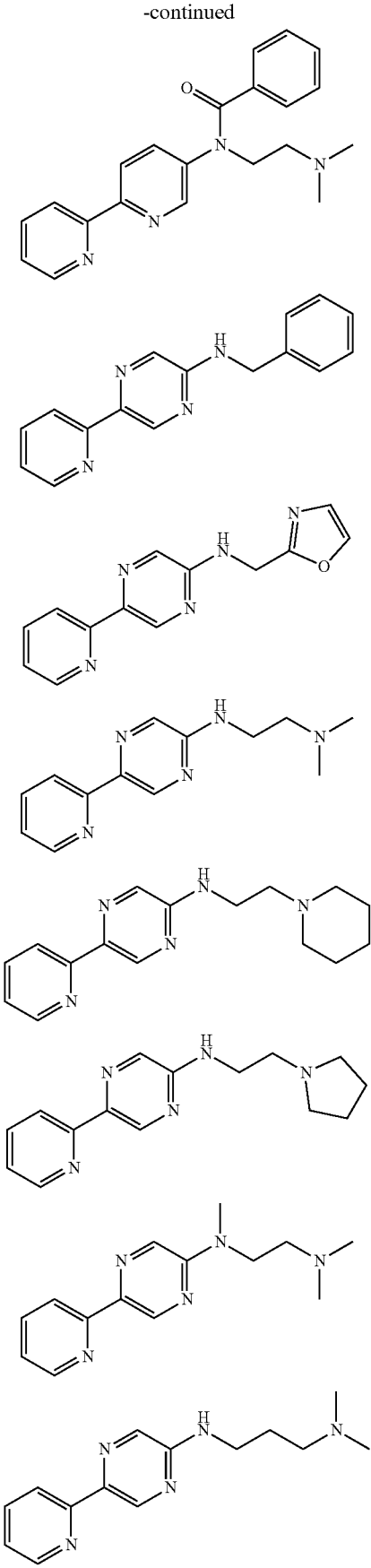

53
-continued
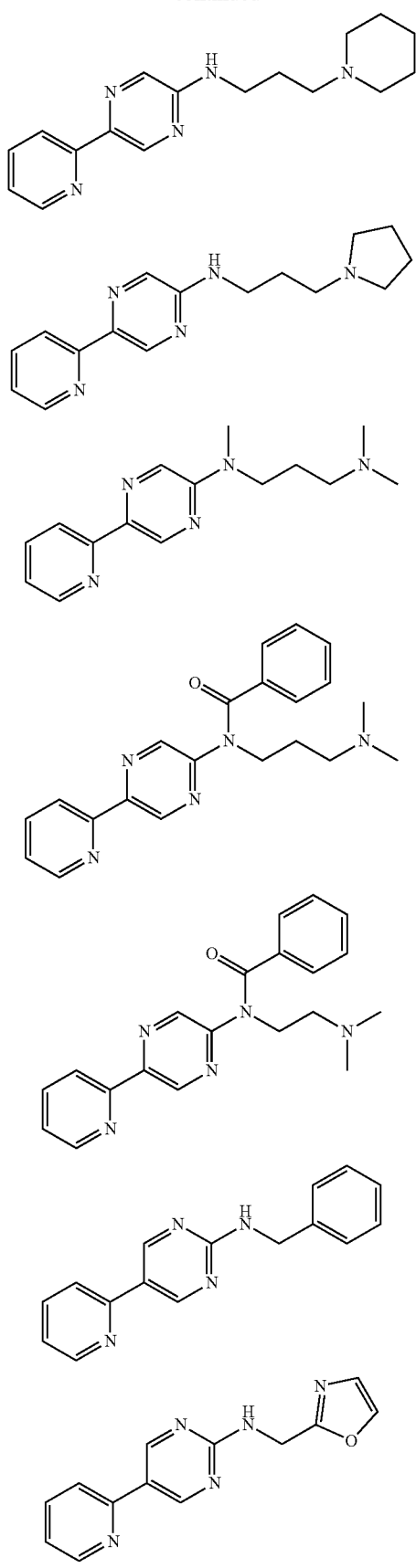
54
-continued
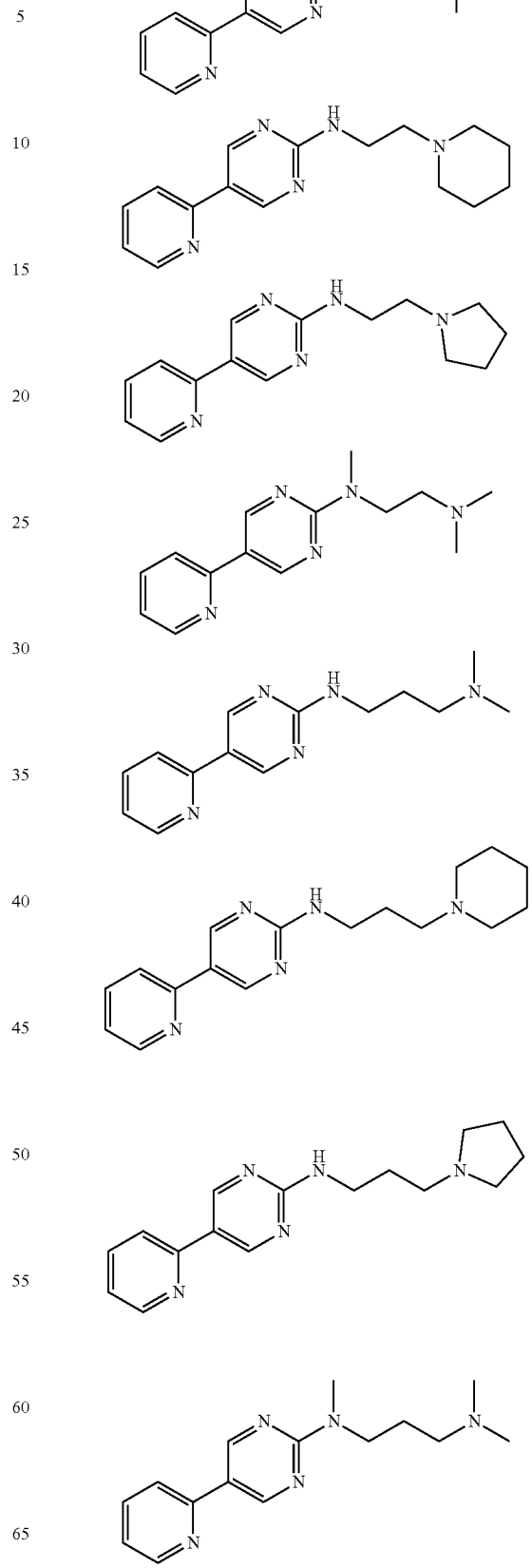

55
-continued
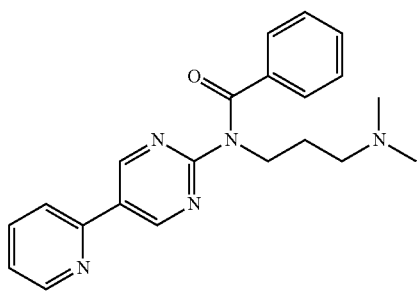
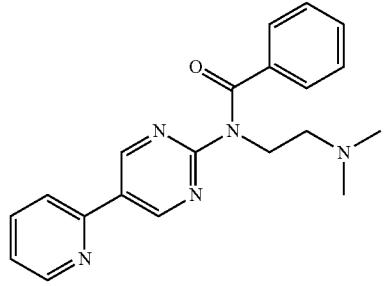
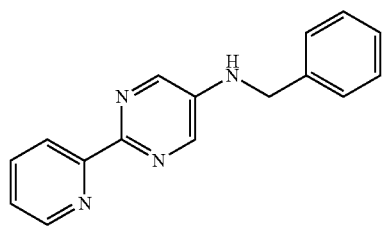
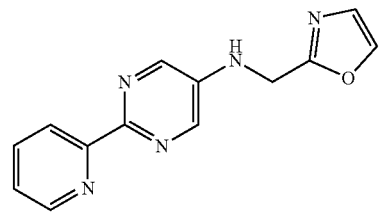
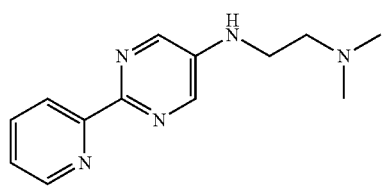
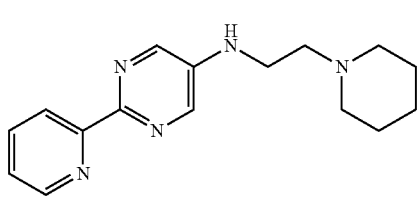
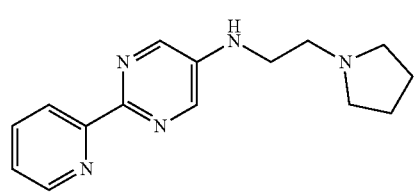
56
-continued
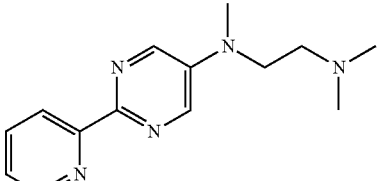
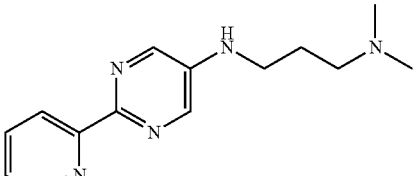
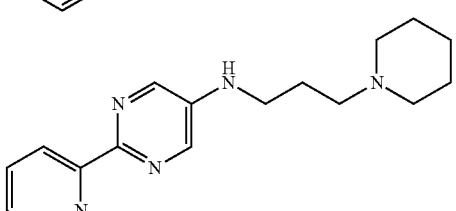
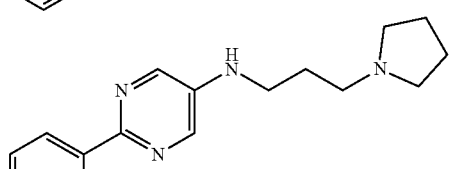
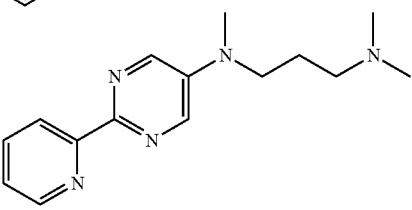
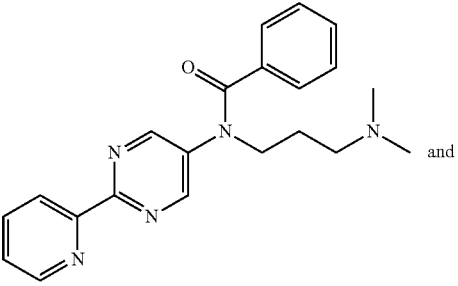
and
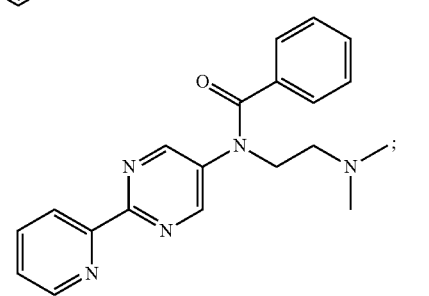
;
or a pharmaceutically acceptable salt thereof.
Synthesis
Compounds of Formula I can be prepared, for example, according to the procedure shown in Scheme 1. An amine-substituted pyridine, pyrimidine, or pyrazine (i) can be reacted with carboxylic acid (ii) in the presence of a C—N coupling agent and a base (e.g., 1-[bis(dimethylamino)methylene]-1H-1,2,3-triazolo[4,5-b]pyridinium 3-oxid hexafluorophosphate (HATU) and N,N-diisopropylethylamine (DIPEA)) to form the amide-substituted pyridine, pyrimidine, or pyrazine analog (iii).

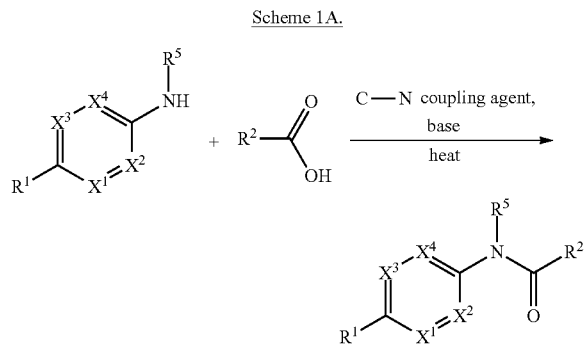

Scheme 1A.

Compounds of Formula I can be prepared, for example, according to the procedure shown in Scheme 1B. An amine substituted pyridine, pyrimidine, or pyrazine (i) can be reacted with an appropriately substituted acid chloride (ii) in the presence of base (e.g., a mixture of 4-dimethylaminopyridine and triethylamine) to form the amide-substituted pyridine, pyrimidine, or pyrazine analog (iii).

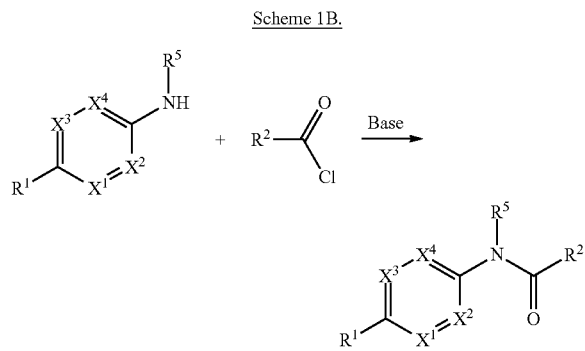

Scheme 1B.

Compounds of Formula II can be prepared, for example, according to the procedure shown in Scheme 2A. A chloro substituted pyridine, pyrimidine, or pyrazine (i) can be reacted with an appropriately substituted alcohol (ii) in the presence of base (e.g., sodium tert-butoxide) to form the ether-substituted pyridine, pyrimidine, or pyrazine analog (iii).

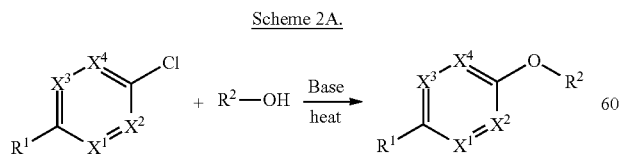

Scheme 2A.

Compounds of Formula II can also be prepared, for example, according to the procedure shown in Scheme 2B. A hydroxy substituted pyridine, pyrimidine, or pyrazine (i) can be reacted with an appropriately substituted alcohol (ii) in the presence of triphenylphosphine ($PPh_3$) and $^tBuO(O)CN\!=\!NC(O)O^tBu$ to form the ether-substituted pyridine, pyrimidine, or pyrazine analog (iii).

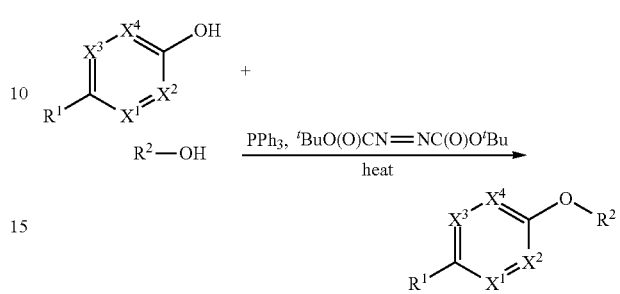

Scheme 2B.

Compounds of Formula III can be prepared, for example, according to the procedure shown in Scheme 3A. A chloro-substituted pyridine, pyrimidine, or pyrazine (i) can be reacted with an appropriately substituted amine (ii) in the presence of KHIMIDS and Brett-phos to form the amine-substituted pyridine, pyrimidine, or pyrazine analog (iii).

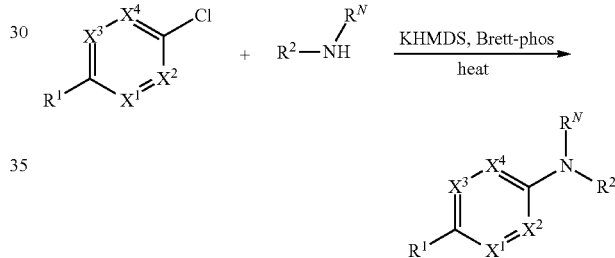

Scheme 3A.

Compounds of Formula III can also be prepared, for example, according to the procedure shown in Scheme 3B. A chloro-substituted pyridine, pyrimidine, or pyrazine (i) can be reacted with an appropriately substituted amine (ii) in the presence of ammonium chloride to form the amine-substituted pyridine, pyrimidine, or pyrazine analog (iii).

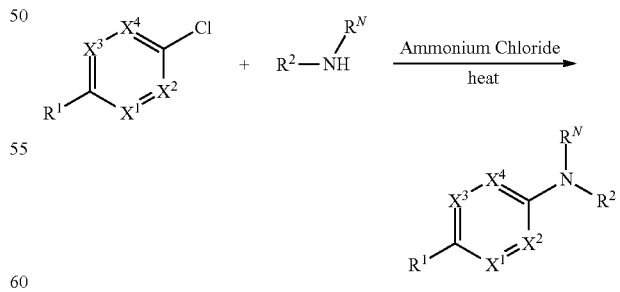

Scheme 3B.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula —NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula —C(O)NH$_2$.

As used herein, the term "carbonyl", employed alone or in combination with other terms, refers to a —C(=O)— group, which may also be written as C(O).

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "halo" refers to F, Cl, Br, or I. In some embodiments, a halo is F, Cl, or Br. In some embodiments, a halo is F or Cl.

As used herein, "$C_{n-m}$ haloalkoxy" refers to a group of formula —O-haloalkyl having n to m carbon atoms. An example haloalkoxy group is OCF$_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide-imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

Methods of Use

The present application further provides methods for the treatment of disorders associated with glutamate excitotoxicity in a subject in need thereof. A number of such disorders are known in the art, and can be readily identified by one of skill in the art. In some embodiments, the methods include a method for treating or preventing glutamate excitotoxicity in a subject in need thereof, the method comprising administering to the subject a therapeutically effective amount of a compound provided herein, or a pharmaceutically acceptable salt thereof. As used herein, the term "subject," refers to any animal, including mammals. For example, the term "subject" includes, but is not limited to, mice, rats, other rodents, rabbits, dogs, cats, swine, cattle, sheep, horses, primates, and humans. In some embodiments, the subject is a human.

In some embodiments, the methods described herein can include in vitro methods, e.g., contacting a sample (e.g., a cell or tissue) with a compound provided herein, or a pharmaceutically acceptable salt thereof.

In some embodiments, the disorder is an acute neurological condition such as ischemic stroke, epilepsy, hypoglycemia, hypoxia, or trauma (see e.g., J. Neurosci. 2016 Oct. 12; 36(41):10529-10544; J. Clin. Invest. 2014 March; 124(3): 1255-67; and Neurochem. Int. 2006 April; 48(5):394-403).

In some embodiments, the disorder is a chronic neurodegenerative disorder such as Parkinson's disease, Alzheimer's disease, multiple sclerosis, mesial temporal sclerosis, Huntington's disease, AIDS dementia complex, or amyotrophic lateral sclerosis (ALS) (see, e.g., Hu et al., "Glutamate receptors in preclinical research on Alzheimer's disease: Update on recent advances." Pharmacol Biochem Behav. 2011 Apr. 22 [Epub ahead of print, doi:10.1016/j.pbb.2011.04.013]; Wang and Qin, Apoptosis. 15(11):1382-402 (2010); Kaul and Lipton, Curr HIV Res. 4(3):307-18 (2006); Kim et al., J Cell Physiol. 226(10):2484-93 (2011); Sheldon and Robinson, Neurochem Int. 51(6-7):333-55 (2007); Guo et al., Hum. Mol. Genet. 2003, 12, 2519; Tian et al., J. Biol. Chem. 282:1727 (2007); Hazell, Neurochem. Int. 50:941 (2007); Seifert et al., Brain. Res. Rev. 63:212 (2010); Tian et al., J. Neurochem. 113:978 (2010); Olney, "Neurotoxicity of excitatory amino acids." In: McGeer E, Olney J, McGeer P, eds. *Kainic Acid as a Tool in Neurobiology.* New York: Raven Press; 1978:95-121; Olney, APMIS Suppl 40:103-112 (2010); J. Exp. Med. 2015 Mar. 9; 212 (3):319-32; Neurobiol. Aging. 2015 Jul; 36(7):2260-71; Neural. Plast. 2016; 2016:8941327; PLoS One. 2008 Sep. 5; 3(9):e3149; J. Clin. Invest. 2014 March; 124(3):1255-67; J. Neurochem. 2012 May; 121(4):629-38; and Curr. HIV Res. 2012 July; 10(5):392-406).

In some embodiments, the disorder is depression (see, e.g., Chen et al., Presynaptic glutamatergic dysfunction in bipolar disorder, Biol. Pshychiatry, 67(11): 1007-1009 (2010)).

In some embodiments, glutamate excitotoxicity can be a result of an environmental toxin, e.g., Tributyltin (Nakatsu et al., Toxicol. Sci. (January 2006) 89 (1): 235-242), lead, and domoic acid.

In some embodiments, excessive glutamate is associated with chronic pain disorders including migraine, fibromyalgia, temporomandibular disorders, neuropathic pain, visceral pain, or complex regional pain syndrome (see, e.g., Chizh et al., Amino Acids, 23(1-3):169-76 (2002); Descalzi et al., Mol Neurobiol. 40(3):253-9. Epub 2009 Oct. 11 (2009); Larsson, Mol Neurobiol. 40(3):260-88 (2009); Yogeswaari et al., Expert Opin Ther Targets. 13(8):925-43 (2009); Vargas, Curr Pain Headache Rep. 13(1):64-6 (2009); Adv. Pharmacol. 2016; 75:245-71; J. Neurochem. 2014 December; 131(6):712-30; Eurasian J Med. 2011 December; 43(3):182-5; and J. Pharmacol. Sci. 2010; 114(4):347-53).

Disruptions in glutamate homeostasis are associated with addictive disorders. As substance abuse develops into addiction, neurochemistry shifts from dopamine-based to predominantly glutamate-based. Thus, subjects suffering from drug addiction and dependence, including alcohol and cocaine addiction, can also be treated using the methods described herein. See, e.g., Tzschentke, Amino Acids 23(1-3):147-52 (2002); Reissner and Kalivas, Behav Pharmacol. 2010 September; 21(5-6):514-22 (2010); Myers et al., Neuropsychopharmacology. 36(1):274-93 (2011); World J. Psychiatry. 2016 Mar. 22; 6(1):31-42; CNS Neurol. Disord. Drug. Targets. 2015; 14(6):745-56; Neuroscientist. 2014 December; 20(6):610-22; and Behav. Pharmacol. 2010 September; 21(5-6):514-22.

Glutamate has also been shown to play a role in some psychotic disorders, including schizophrenia, bipolar disorder, and autism (see e.g., Curr Mol Pharmacol. 2013 July; 6(2):66-73; Eur J Pharmacol. 2012 May 5; 682(1-3):1-11; Iran J Child Neurol. 2015 Winter; 9(1):99-102; J Biomed Sci. 2005 December; 12(6):975-84. The methods and compounds described herein can be used to treat subjects with psychotic disorders such as schizophrenia, bipolar disorder, and autism.

Glutamate has also been shown to play a role in some cancers, including necrosis in glioblastoma, which is associated with poor prognosis. See, e.g., Noch and Khalili, Cancer Biol Ther. 8(19):1791-7 (2009). Thus, the compounds and compositions described herein can be used to treat subjects with cancers, e.g., brain cancers such as glioblastoma and glioma.

Glutamate has been shown to play a role in modulating various mood disorders, for example, major depressive disorder (Owen, Drugs today, 2012, 48(7):469-78), anxiety disorders (see e.g., Neuropsychiatr Dis Treat. 2013; 9:1101-12), depressive disorders (see e.g., Expert Rev Clin Pharmacol. 2016 Oct. 26; Biol Psychiatry. 2007 Jan. 15; 61(2): 250-2; and Biol Psychiatry. 2007 Jan. 15; 61(2):137-8), borderline personality disorder (see e.g., Neuropsychopharmacology. 2016 January; 41(2):410-8), attention-deficit-hyperactivity disorder (see e.g., Neuropsychopharmacology. 2016 January; 41(2):410-8; and World J. Biol. Psychiatry. 2016 Dec. 15:1-9), suicidal behavior (see e.g., Prog. Neuropsychopharmacol Biol. Psychiatry. 2016 Oct. 27), eating disorders (see e.g., Curr. Pharm. Des. 2011; 17(14):1396-409), posttraumatic stress disorder (see e.g., Neurosci. Lett. 2016 Dec. 1), gulf war illness (see e.g., J. Neurochem. 2011 October; 119(2):303-13), and obsessive-Compulsive Disorder (see e.g., Pharmacol. Ther. 2011 December; 132(3): 314-332).

The presence of a disorder associated with glutamate excitotoxicity can be diagnosed or determined using methods known in the art, including spectroscopy at 0.5 T to observe the combined glutamate and glutamine (glx) peak (see, e.g., Prost et al., Magn Reson Med 1997; 37:615-618; Mark et al., American Journal of Neuroradiology 22:1813-1824 (2001)). Other known clinical diagnostic methods can also be used to diagnose the presence of a disorder known to be associated with glutamate excitotoxicity, e.g., as described herein.

In some embodiments, glutamate excitotoxicity (and subsequent neurological damage) can be a result of an environmental toxin, e.g., Tributyltin (Nakatsu et al., Toxicol. Sci. (January 2006) 89 (1): 235-242), lead, and domoic acid. Subjects who have been or will be exposed to such toxins can be considered to have a disorder associated with glutamate excitotoxicity and can be treated using the methods described herein. In some embodiments subjects who have been exposed to an environmental toxin known to cause or contribute to glutamate excitotoxicity can be treated using the methods described herein before the onset of clinical (e.g., neurological) symptoms, to prevent or reduce the risk of a disorder associated with glutamate excitotoxicity.

In some embodiments, the present application provides a method for treating a disease or disorder selected from the group consisting of ischemic stroke, epilepsy, trauma, a chronic neurodegenerative disorder, a psychotic disorder, a pain disorder, an addiction, a cancer, a mood disorder, or depression in a subject in need thereof, the method comprising administering to the subject an effective amount of a compound provided herein, or a pharmaceutically acceptable salt thereof.

In some embodiments, the present application provides a method for treating a disease or disorder selected from the group consisting of ischemic stroke, epilepsy, trauma, a chronic neurodegenerative disorder, a psychotic disorder, a pain disorder, an addiction, a cancer, or depression in a subject in need thereof, the method comprising administering to the subject an effective amount of a compound provided herein, or a pharmaceutically acceptable salt thereof.

Example traumas include, but are not limited to, blunt trauma, an abrasion, an avulsion, an incision, a laceration, a puncture, a penetration, a surgical trauma, iatrogenic trauma, a spinal cord injury, a traumatic brain injury, or any combination thereof.

In some embodiments, the chronic neurodegenerative disorder is selected from the group consisting of mild cognitive impairment, Parkinson's disease, Alzheimer's disease, multiple sclerosis, mesial temporal sclerosis, Huntington's disease, AIDS dementia complex, and amyotrophic lateral sclerosis (ALS).

In some embodiments, the psychotic disorder is selected from the group consisting of schizophrenia, bipolar disorder, and autism.

In some embodiments, the pain disorder is selected from the group consisting of migraine, a temporomandibular disorder, neuropathic pain, visceral pain, or complex regional pain syndrome.

In some embodiments, the addiction is selected from the group consisting of alcohol addition, cocaine addiction, heroin addiction, methamphetamine addiction, and nicotine addiction. In some embodiments, the addiction is selected from the group consisting of alcohol addiction and cocaine addiction.

In some embodiments, the cancer is selected from the group consisting of brain cancer, glioblastoma, and glioma. In some embodiments, the cancer is glioblastoma. In some embodiments, the cancer is glioma.

In some embodiments, the mood disorder is selected from the group consisting of an anxiety disorder, a depressive disorder, borderline personality disorder, attention-deficit-hyperactivity disorder, suicidal behavior, an eating disorder, posttraumatic stress disorder, gulf war illness, and obsessive-Compulsive Disorder.

In some embodiments, the depression comprises major depressive disorder. In some embodiments, the depression is major depressive disorder.

In some embodiments, the present application provides a method for treating a disease or disorder selected from the group consisting of ischemic stroke, epilepsy, trauma, or a chronic neurodegenerative disorder, including mild cognitive impairment, Parkinson's disease, Alzheimer's disease, multiple sclerosis, mesial temporal sclerosis, Huntington's disease, AIDS dementia complex, or amyotrophic lateral sclerosis (ALS); a psychotic disorder including schizophrenia, bipolar disorder, and autism, a pain disorder including migraine, temporomandibular disorders, neuropathic pain, visceral pain, or complex regional pain syndrome; an addiction including alcohol addiction, cocaine addiction, heroin addiction, methamphetamine addiction, and nicotine addiction; or a cancer, including glioblastoma; or depression in a subject in need thereof, the method comprising administering to the subject an effective amount of a compound provided herein, or a pharmaceutically acceptable salt thereof.

The present application further provides a method for increasing EAAT2 protein expression in a cell or a subject in need thereof, the method comprising contacting the cell or administering to the subject an effective amount of a compound provided herein, or a pharmaceutically acceptable salt thereof.

The present application further provides a method for activating the NRF2 pathway in a cell or a subject in need thereof, the method comprising contacting the cell or administering to the subject an effective amount of a compound provided herein, or a pharmaceutically acceptable salt thereof.

As used herein, the phrase "effective amount" refers to the amount of active compound or pharmaceutical agent that elicits the biological or medicinal response that is being sought in a tissue, system, animal, individual or human by a researcher, veterinarian, medical doctor or other clinician. An effective amount of a compound provided herein can range, for example, from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

As used herein, to "treat" means to ameliorate at least one symptom of the disorder associated with glutamate excitotoxicity. Often, glutamate excitotoxicity results in neuronal cell death; thus, a treatment can result in a reduction in the rate or amount of neuronal cell death.

Combination Therapies

In some embodiments, the methods provided herein further comprise administering one or more additional therapeutic agents to the subject. In some embodiments, each of the one or more additional therapeutic agents is independently selected from the group consisting of a steroid, an anti-allergic agent, an anesthetic (e.g., for use in combination with a surgical procedure), an immunosuppressant, an anti-microbial agent, an anti-inflammatory agent, and a chemotherapeutic agent.

Example steroids include, but are not limited to, corticosteroids such as cortisone, dexamethasone, hydrocortisone, methylprednisolone, prednisolone, and prednisone.

Example anesthetics include, but are not limited to local anesthetics such as lidocaine, procain, and ropivacaine.

Example immunosuppressants include, but are not limited to, azathioprine, chlorambucil, cyclophosphamide, cyclosporine, daclizumab, infliximab, methotrexate, and tacrolimus.

Example anti-microbial agents include, but are not limited to, aminoglycosides (e.g., gentamicin, neomycin, and streptomycin), penicillins (e.g., amoxicillin and ampicillin), and macrolides (e.g., erythromycin).

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example chemotherapeutics include, but are not limited to, proteosome inhibitors (e.g., bortezomib), thalidomide, revlimid, and DNA-damaging agents such as melphalan, doxorubicin, cyclophosphamide, vincristine, etoposide, carmustine, and the like. For example, one or more of the following agents may be used in combination with the compounds provided herein and are presented as a non-limiting list: a cytostatic agent, cisplatin, taxol, etoposide, irinotecan, topotecan, paclitaxel, docetaxel, epothilones, tamoxifen, 5-fluorouracil, temozolomide, cyclophosphamide, gefitinib, erlotinib hydrochloride, imatinib mesylate, gemcitabine, uracil mustard, chlormethine, ifosfamide, chlorambucil, pipobroman, triethylenemelamine, triethylenethiophosphoramine, busulfan, lomustine, streptozocin, dacarbazine, floxuridine, cytarabine, 6-mercaptopurine, 6-thioguanine, fludarabine phosphate, oxaliplatin, folinic acid, pentostatin, vinblastine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methyltestosterone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, ifosfamide, rituximab, alemtuzumab, clofarabine, cladribine, aphidicolin, sunitinib, dasatinib, tezacitabine, triapine, trimidox, amidox, bendamustine, and ofatumumab.

Pharmaceutical Compositions

When employed as pharmaceuticals, the compounds provided herein and pharmaceutically acceptable salts thereof can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds provided herein, or a pharmaceutically acceptable salt thereof, are suitable for parenteral administration. In some embodiments, the compounds provided herein are suitable for intravenous administration. In some embodiments, the compounds provided herein are suitable for oral administration. In some embodiments, the compounds provided herein are suitable for topical administration.

Pharmaceutical compositions and formulations for topical administration may include, but are not limited to, transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the pharmaceutical compositions provided herein are suitable for intravenous administration. In some embodiments, the pharmaceutical compositions provided herein are suitable for oral administration. In some embodiments, the pharmaceutical compositions provided herein are suitable for topical administration.

Also provided are pharmaceutical compositions which contain, as the active ingredient, a compound provided herein, or a pharmaceutically acceptable salt thereof, in combination with one or more pharmaceutically acceptable carriers (e.g. excipients). In making the pharmaceutical compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be, for example, in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in an effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The compositions provided herein can be administered one from one or more times per day to one or more times per week; including once every other day. The skilled artisan will appreciate that certain factors can influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a compound described herein can include a single treatment or a series of treatments.

Dosage, toxicity and therapeutic efficacy of the compounds provided herein can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds exhibiting high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. General Procedure for Synthesis of Amide Analogs

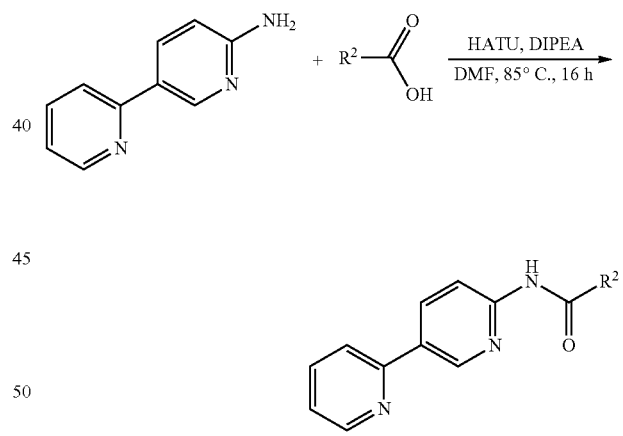

N,N-Diisopropylethylamine (DIPEA) (258 mg, 2.0 mmol) is slowly added dropwise to a solution of 1-[bis(dimethylamino)methylene]-1H-1,2,3-triazolo[4,5-b]pyridinium 3-oxid hexafluorophosphate (HATU) (456 mg, 1.2 mmol) in DMF (2.0 mL). The solution is stirred for 5 minutes and then added dropwise to a mixture of the appropriately substituted carboxylic acid (1.0 mmol) and 2,3'-bipyridin-6'-amine (171 mg, 1.0 mmol) in a reaction vial. The solution is then stirred at 85° C. for 16 hours. The reaction is monitored by TLC or LCMS. The residue is purified using a silica or basic alumina column chromatography and eluted with the appropriate solvent mixtures (e.g., ethyl acetate-methanol-triethylamine, or cyclohexane-ethyl acetate) to give the desired compound.

Example 2. Alternative Procedure for Synthesis of Amide Analogs

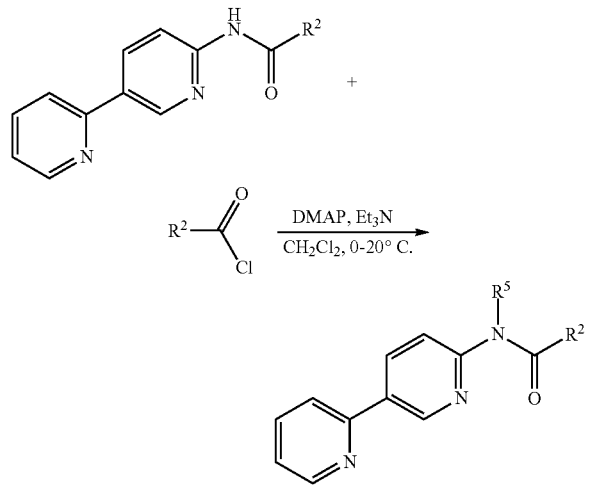

The appropriate amine product (0.17 mmol), DMAP (4.5 mg, 0.04 mmol) and triethylamine (41.8 µL, 0.3 mmol) are dissolved in dichloromethane (1 mL) and cooled to 0° C. The appropriately substituted acid chloride (0.4 mmol) is added dropwise to the stirring solution. The reaction mixture is slowly warmed to room temperature and then stirred for 5 hours. To the reaction mixture is added dichloromethane (2 mL) and sat. aqueous $NH_4Cl$ (1 mL) and the organic layer is extracted. The aqueous layer is then extracted with dichloromethane (2×2 mL) and the organic fractions are combined, dried over $Na_2SO_4$, filtered, and evaporated under reduced pressure. The residue is purified using a silica or basic alumina column chromatography and eluted with the appropriate solvent mixtures (e.g., ethyl acetate-methanol-triethylamine, or cyclohexane-ethyl acetate) to give the desired compound.

Examples 3-87

The compounds of Examples 3-87 can be prepared according to the procedures described in Examples 1-2 using appropriately substituted starting materials.

| Example No. | Compound Structure | Compound Name |
|---|---|---|
| 3 | 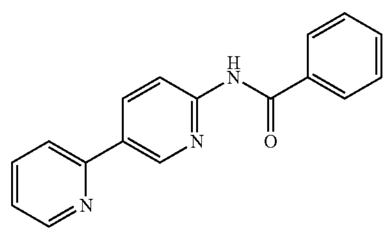 | N-([2,3,-bipyridin]-6'-yl)benzamide |
| 4 | 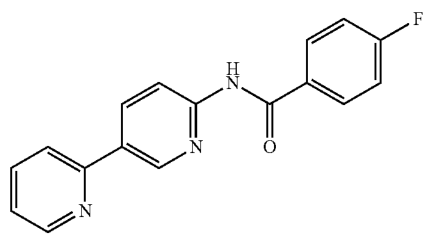 | N-([2,3'-bipyridin]-6'-yl)-4-fluorobenzamide |
| 5 | 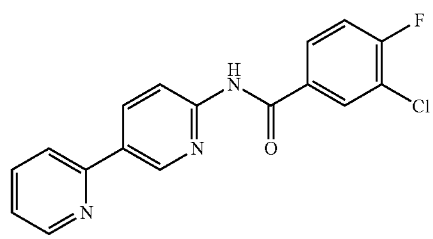 | N-([2,3'-bipyridin]-6'-yl)-3-chloro-4-fluorobenzamide |
| 6 | 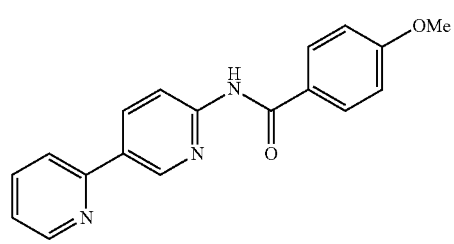 | N-([2,3'-bipyridin]-6'-yl)-4-methoxybenzamide |

-continued
| Example No. | Compound Structure | Compound Name |
|---|---|---|
| 7 | 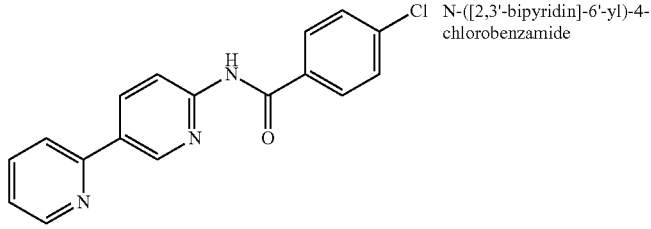 | N-([2,3'-bipyridin]-6'-yl)-4-chlorobenzamide |
| 8 | 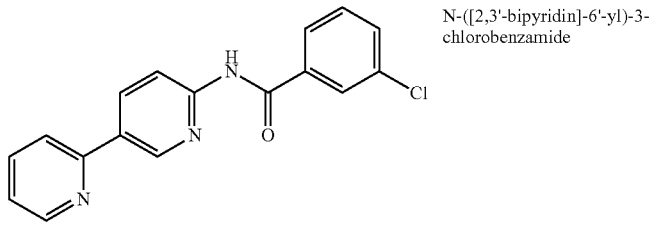 | N-([2,3'-bipyridin]-6'-yl)-3-chlorobenzamide |
| 9 | 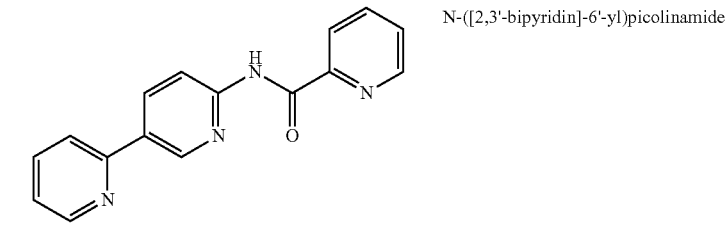 | N-([2,3'-bipyridin]-6'-yl)picolinamide |
| 10 | 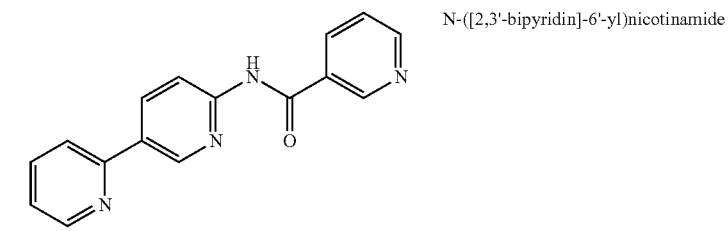 | N-([2,3'-bipyridin]-6'-yl)nicotinamide |
| 11 | 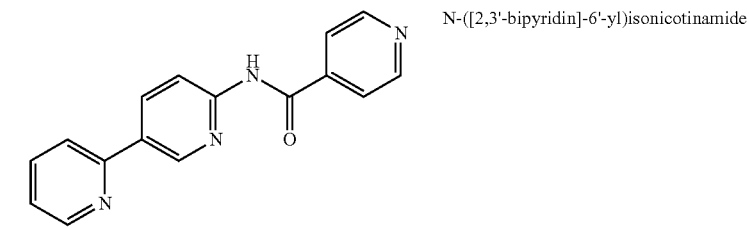 | N-([2,3'-bipyridin]-6'-yl)isonicotinamide |
| 12 | 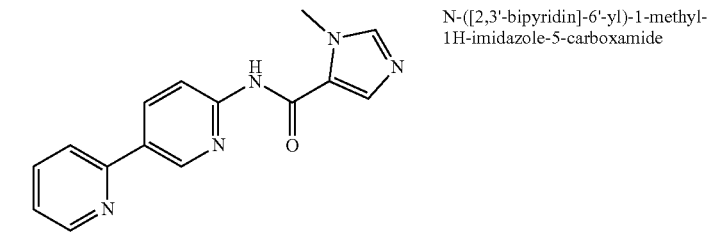 | N-([2,3'-bipyridin]-6'-yl)-1-methyl-1H-imidazole-5-carboxamide |

-continued

| Example No. | Compound Structure | Compound Name |
|---|---|---|
| 13 | 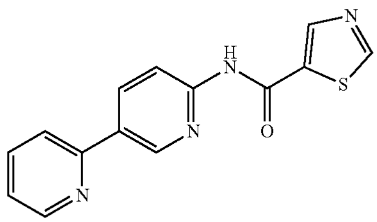 | N-([2,3'-bipyridin]-6'-yl)thiazole-5-carboxamide |
| 14 | 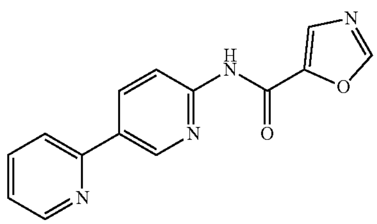 | N-([2,3'-bipyridin]-6'-yl)oxazole-5-carboxamide |
| 15 | 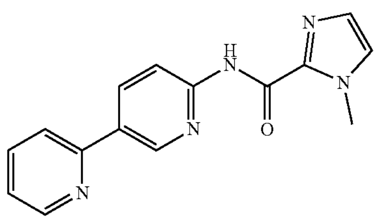 | N-([2,3'-bipyridin]-6'-yl)-1-methyl-1H-imidazole-2-carboxamide |
| 16 | 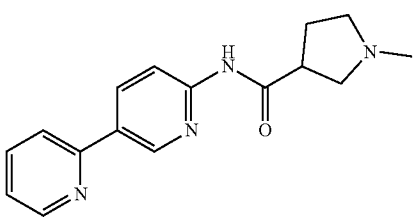 | N-([2,3'-bipyridin]-6'-yl)-1-methylpyrrolidine-3-carboxamide |
| 17 | 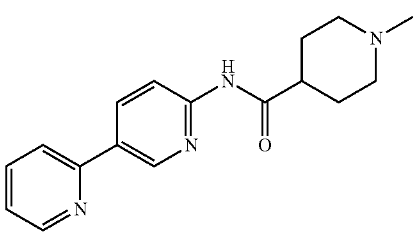 | N-([2,3'-bipyridin]-6'-yl)-1-methylpiperidine-4-carboxamide |
| 18 | 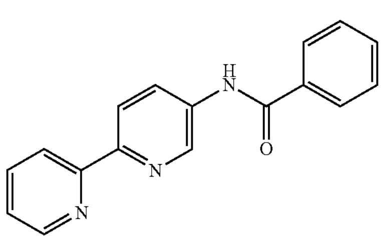 | N-([2,2'-bipyridin]-5-yl)benzamide |

| Example No. | Compound Structure | Compound Name |
|---|---|---|
| 19 | 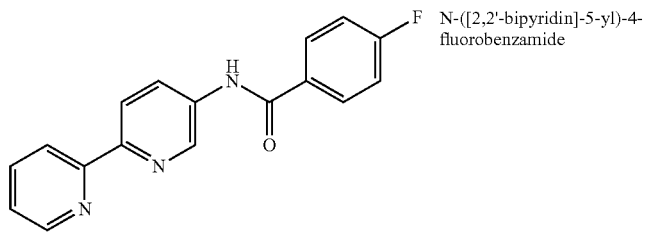 | N-([2,2'-bipyridin]-5-yl)-4-fluorobenzamide |
| 20 | 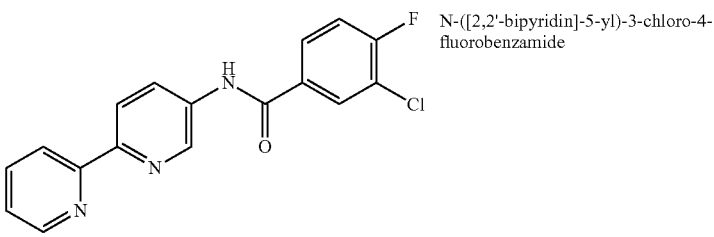 | N-([2,2'-bipyridin]-5-yl)-3-chloro-4-fluorobenzamide |
| 21 | 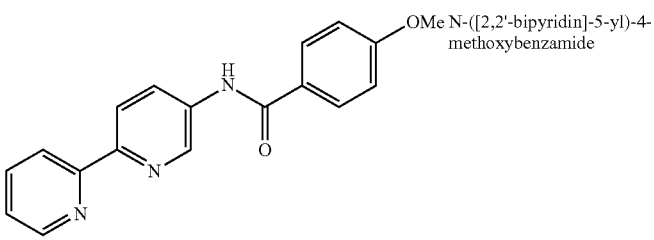 | N-([2,2'-bipyridin]-5-yl)-4-methoxybenzamide |
| 22 | 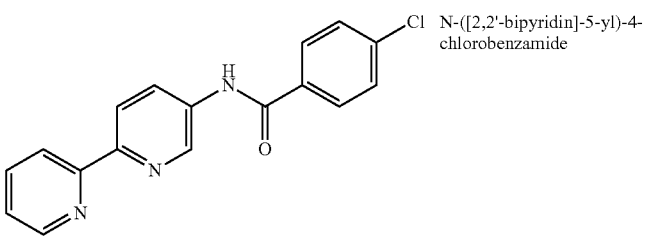 | N-([2,2'-bipyridin]-5-yl)-4-chlorobenzamide |
| 23 | 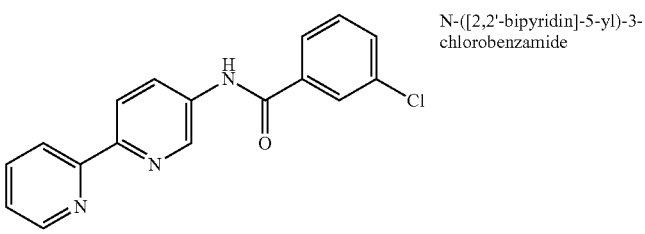 | N-([2,2'-bipyridin]-5-yl)-3-chlorobenzamide |
| 24 | 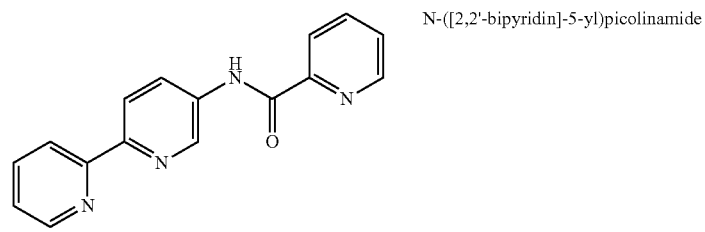 | N-([2,2'-bipyridin]-5-yl)picolinamide |

-continued

| Example No. | Compound Structure | Compound Name |
|---|---|---|
| 25 | 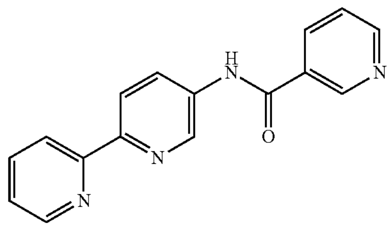 | N-([2,2'-bipyridin]-5-yl)nicotinamide |
| 26 | 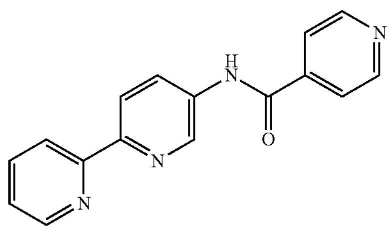 | N-([2,2'-bipyridin]-5-yl)isonicotinamide |
| 27 | 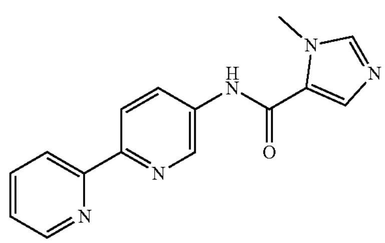 | N-([2,2'-bipyridin]-5-yl)-1-methyl-1H-imidazole-5-carboxamide |
| 28 | 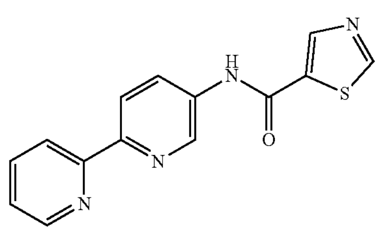 | N-([2,2'-bipyridin]-5-yl)thiazole-5-carboxamide |
| 29 | 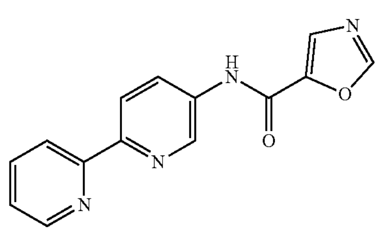 | N-([2,2'-bipyridin]-5-yl)oxazole-5-carboxamide |
| 30 | 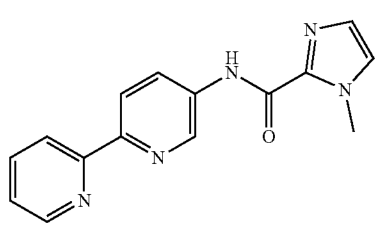 | N-([2,2'-bipyridin]-5-yl)-1-methyl-1H-imidazole-2-carboxamide |

-continued
| Example No. | Compound Structure | Compound Name |
|---|---|---|
| 31 | 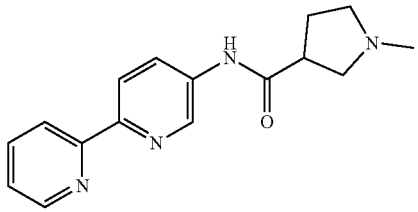 | N-([2,2'-bipyridin]-5-yl)-1-methylpyrrolidine-3-carboxamide |
| 32 | 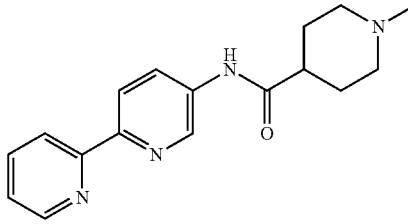 | N-([2,2'-bipyridin]-5-yl)-1-methylpiperidine-4-carboxamide |
| 33 | 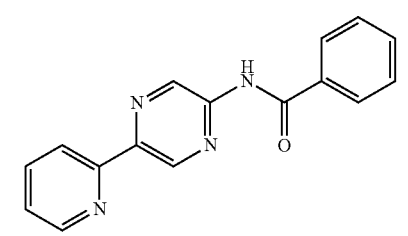 | N-(5-(pyridin-2-yl)pyrazin-2-yl)benzamide |
| 34 | 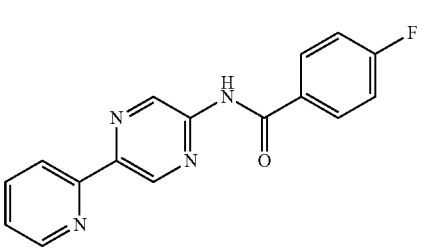 | 4-fluoro-N-(5-(pyridin-2-yl)pyrazin-2-yl)benzamide |
| 35 | 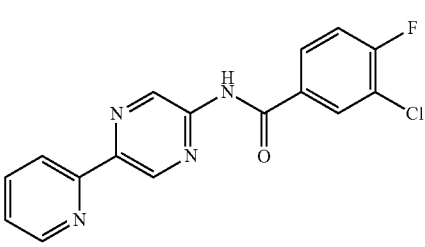 | 3-chloro-4-fluoro-N-(5-(pyridin-2-yl)pyrazin-2-yl)benzamide |
| 36 | 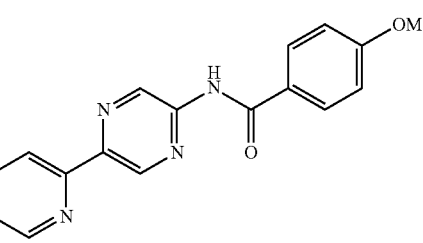 | 4-methoxy-N-(5-(pyridin-2-yl)pyrazin-2-yl)benzamide |

| Example No. | Compound Structure | Compound Name |
|---|---|---|
| 37 | 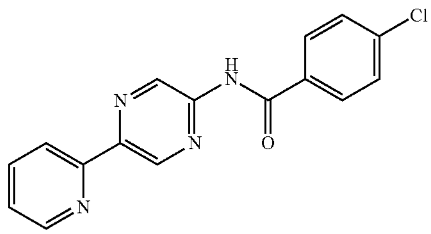 | 4-chloro-N-(5-(pyridin-2-yl)pyrazin-2-yl)benzamide |
| 38 | 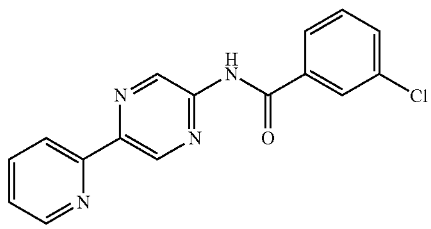 | 3-chloro-N-(5-(pyridin-2-yl)pyrazin-2-yl)benzamide |
| 39 | 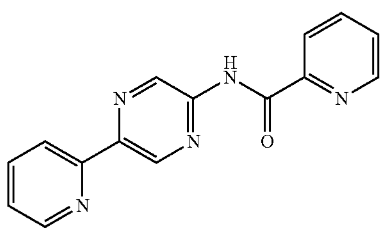 | N-(5-(pyridin-2-yl)pyrazin-2-yl)picolinamide |
| 40 | 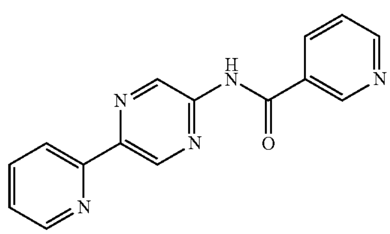 | N-(5-(pyridin-2-yl)pyrazin-2-yl)nicotinamide |
| 41 | 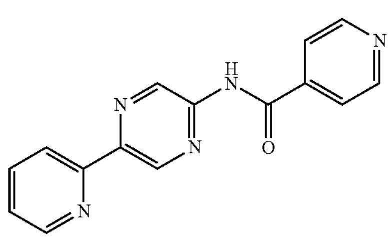 | N-(5-(pyridin-2-yl)pyrazin-2-yl)isonicotinamide |
| 42 | 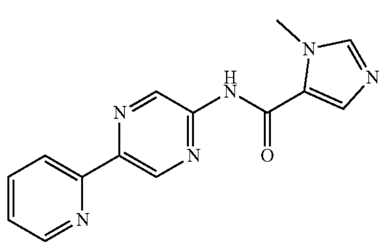 | 1-methyl-N-(5-(pyridin-2-yl)pyrazin-2-yl)-1H-imidazole-5-carboxamide |

| Example No. | Compound Structure | Compound Name |
|---|---|---|
| 43 | 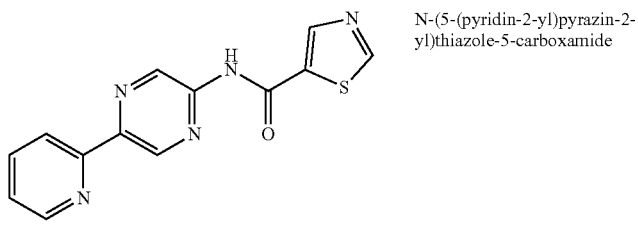 | N-(5-(pyridin-2-yl)pyrazin-2-yl)thiazole-5-carboxamide |
| 44 | 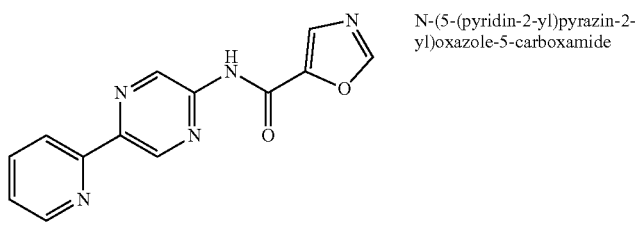 | N-(5-(pyridin-2-yl)pyrazin-2-yl)oxazole-5-carboxamide |
| 45 | 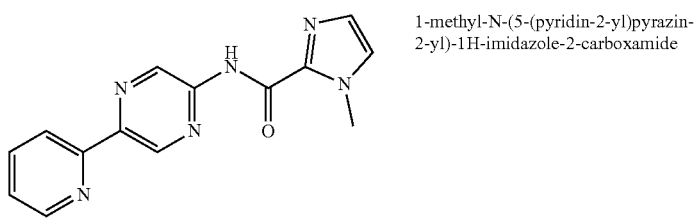 | 1-methyl-N-(5-(pyridin-2-yl)pyrazin-2-yl)-1H-imidazole-2-carboxamide |
| 46 | 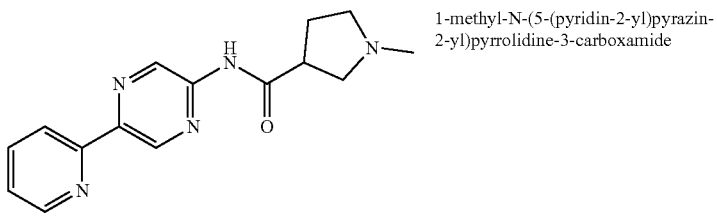 | 1-methyl-N-(5-(pyridin-2-yl)pyrazin-2-yl)pyrrolidine-3-carboxamide |
| 47 | 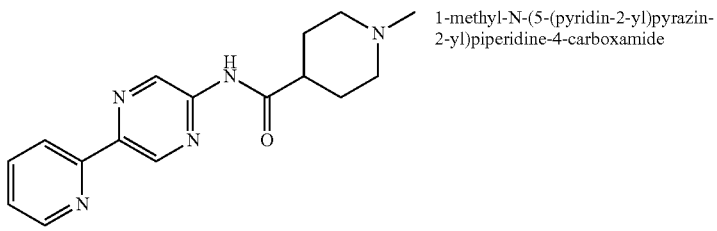 | 1-methyl-N-(5-(pyridin-2-yl)pyrazin-2-yl)piperidine-4-carboxamide |
| 48 | 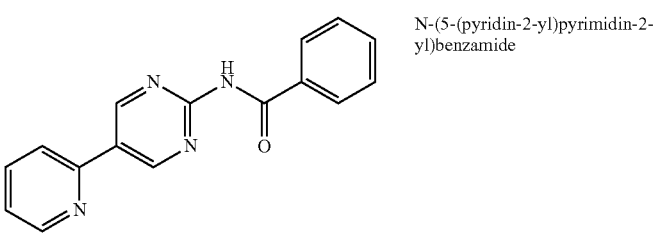 | N-(5-(pyridin-2-yl)pyrimidin-2-yl)benzamide |

-continued
| Example No. | Compound Structure | Compound Name |
|---|---|---|
| 49 | 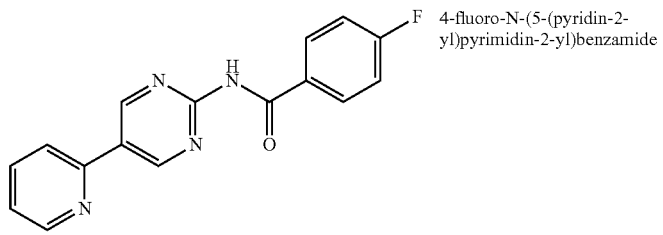 | 4-fluoro-N-(5-(pyridin-2-yl)pyrimidin-2-yl)benzamide |
| 50 | 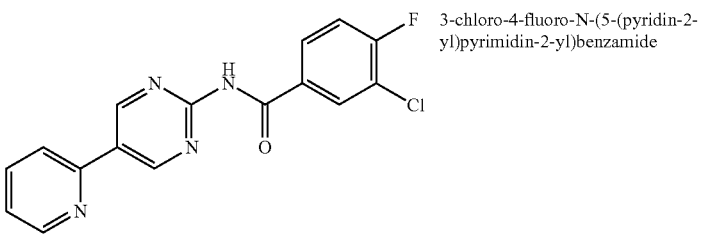 | 3-chloro-4-fluoro-N-(5-(pyridin-2-yl)pyrimidin-2-yl)benzamide |
| 51 | 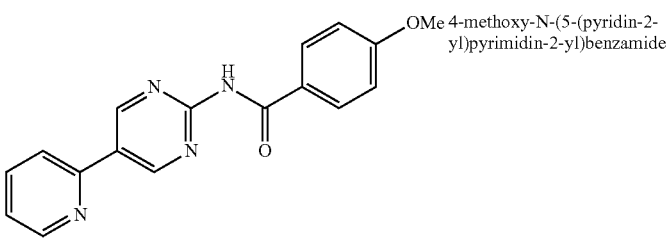 | 4-methoxy-N-(5-(pyridin-2-yl)pyrimidin-2-yl)benzamide |
| 52 | 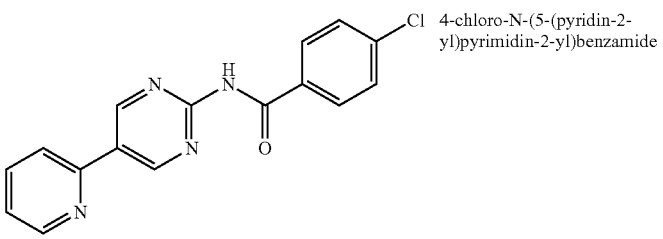 | 4-chloro-N-(5-(pyridin-2-yl)pyrimidin-2-yl)benzamide |
| 53 | 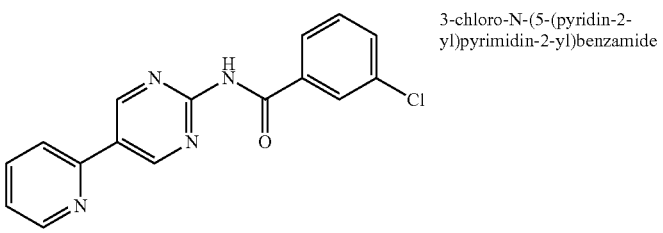 | 3-chloro-N-(5-(pyridin-2-yl)pyrimidin-2-yl)benzamide |
| 54 | 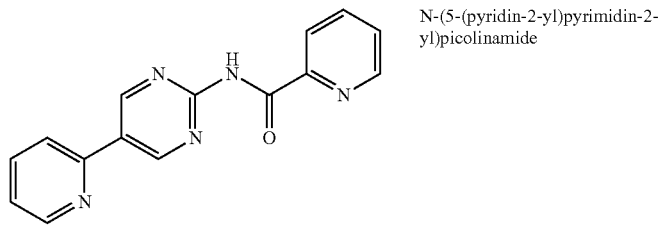 | N-(5-(pyridin-2-yl)pyrimidin-2-yl)picolinamide |

-continued

| Example No. | Compound Structure | Compound Name |
|---|---|---|
| 55 | 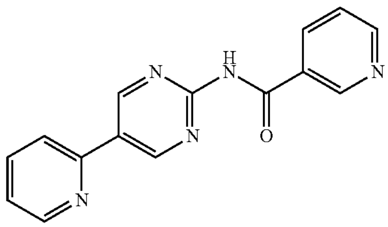 | N-(5-(pyridin-2-yl)pyrimidin-2-yl)nicotinamide |
| 56 | 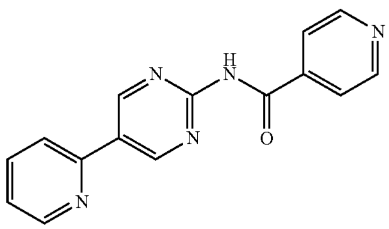 | N-(5-(pyridin-2-yl)pyrimidin-2-yl)isonicotinamide |
| 57 | 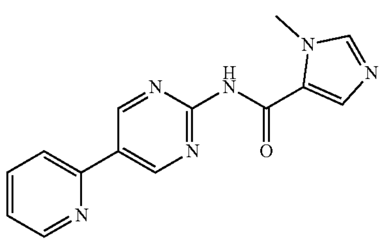 | 1-methyl-N-(5-(pyridin-2-yl)pyrimidin-2-yl)-1H-imidazole-5-carboxamide |
| 58 | 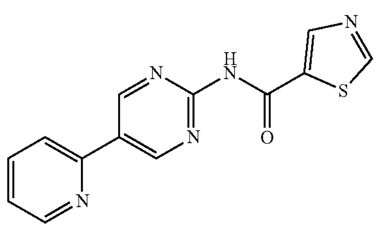 | N-(5-(pyridin-2-yl)pyrimidin-2-yl)thiazole-5-carboxamide |
| 59 | 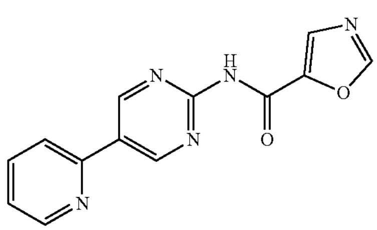 | N-(5-(pyridin-2-yl)pyrimidin-2-yl)oxazole-5-carboxamide |
| 60 | 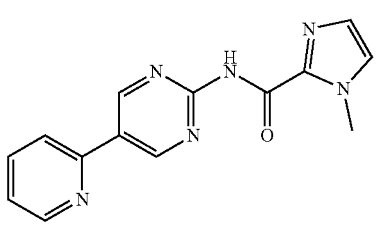 | 1-methyl-N-(5-(pyridin-2-yl)pyrimidin-2-yl)-1H-imidazole-2-carboxamide |

-continued
| Example No. | Compound Structure | Compound Name |
|---|---|---|
| 61 | 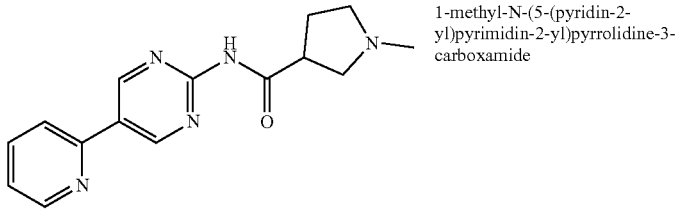 | 1-methyl-N-(5-(pyridin-2-yl)pyrimidin-2-yl)pyrrolidine-3-carboxamide |
| 62 | 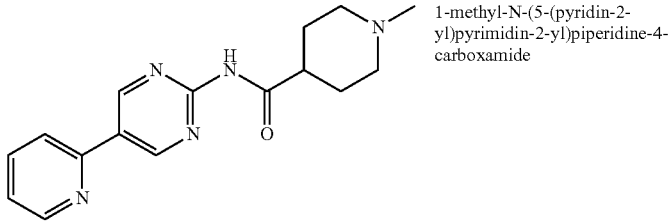 | 1-methyl-N-(5-(pyridin-2-yl)pyrimidin-2-yl)piperidine-4-carboxamide |
| 63 | 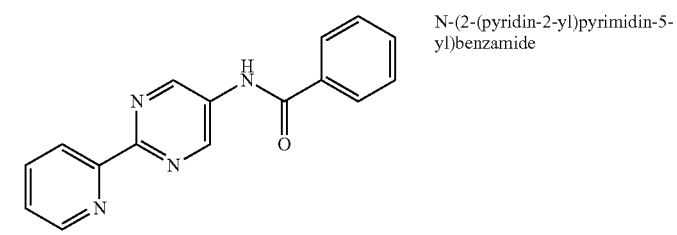 | N-(2-(pyridin-2-yl)pyrimidin-5-yl)benzamide |
| 64 | 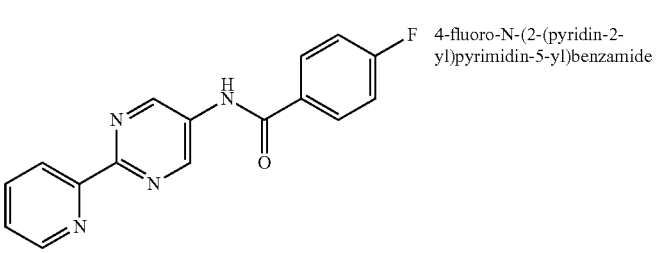 | 4-fluoro-N-(2-(pyridin-2-yl)pyrimidin-5-yl)benzamide |
| 65 | 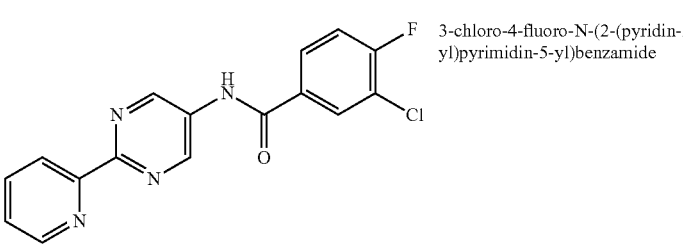 | 3-chloro-4-fluoro-N-(2-(pyridin-2-yl)pyrimidin-5-yl)benzamide |
| 66 | 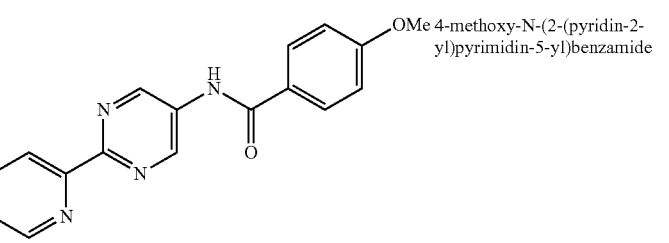 | 4-methoxy-N-(2-(pyridin-2-yl)pyrimidin-5-yl)benzamide |

-continued

| Example No. | Compound Structure | Compound Name |
|---|---|---|
| 67 | 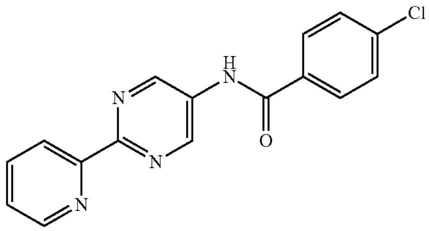 | 4-chloro-N-(2-(pyridin-2-yl)pyrimidin-5-yl)benzamide |
| 68 | 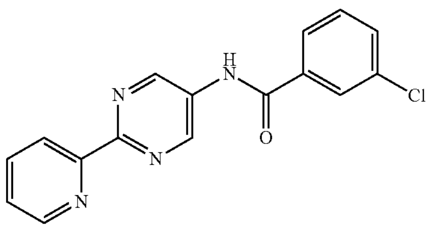 | 3-chloro-N-(2-(pyridin-2-yl)pyrimidin-5-yl)benzamide |
| 69 | 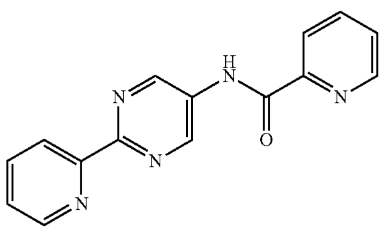 | N-(2-(pyridin-2-yl)pyrimidin-5-yl)picolinamide |
| 70 | 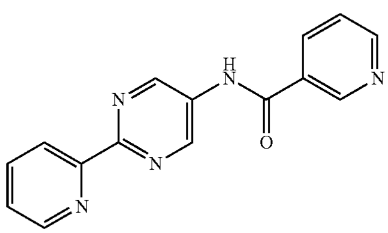 | N-(2-(pyridin-2-yl)pyrimidin-5-yl)nicotinamide |
| 71 | 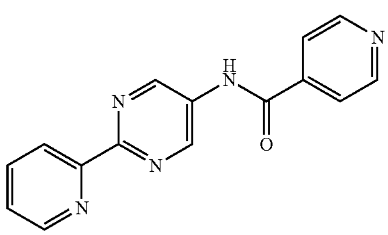 | N-(2-(pyridin-2-yl)pyrimidin-5-yl)isonicotinamide |
| 72 | 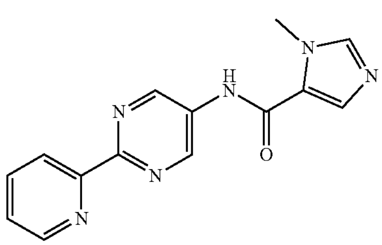 | 1-methyl-N-(2-(pyridin-2-yl)pyrimidin-5-yl)-1H-imidazole-5-carboxamide |

| Example No. | Compound Structure | Compound Name |
|---|---|---|
| 73 | 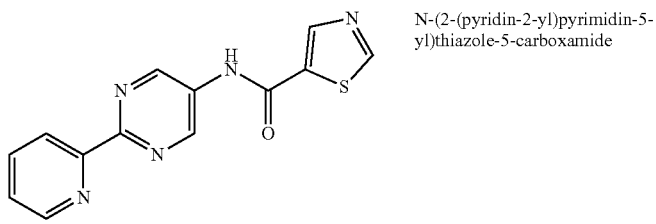 | N-(2-(pyridin-2-yl)pyrimidin-5-yl)thiazole-5-carboxamide |
| 74 | 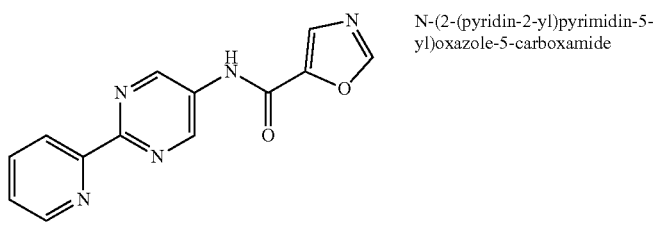 | N-(2-(pyridin-2-yl)pyrimidin-5-yl)oxazole-5-carboxamide |
| 75 | 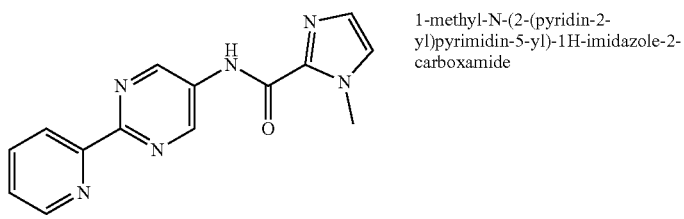 | 1-methyl-N-(2-(pyridin-2-yl)pyrimidin-5-yl)-1H-imidazole-2-carboxamide |
| 76 | 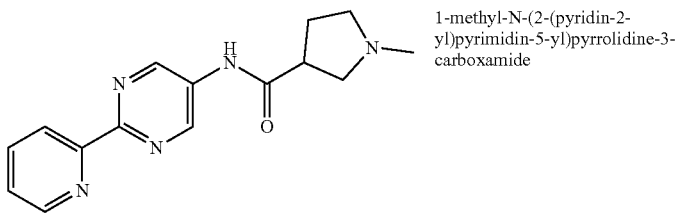 | 1-methyl-N-(2-(pyridin-2-yl)pyrimidin-5-yl)pyrrolidine-3-carboxamide |
| 77 | 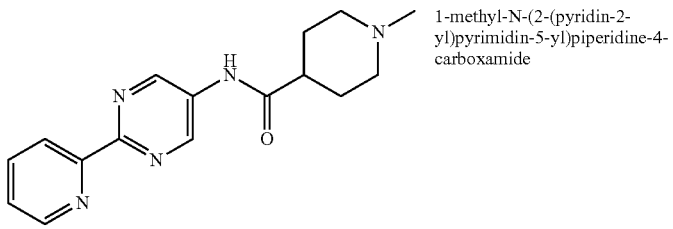 | 1-methyl-N-(2-(pyridin-2-yl)pyrimidin-5-yl)piperidine-4-carboxamide |
| 78 | 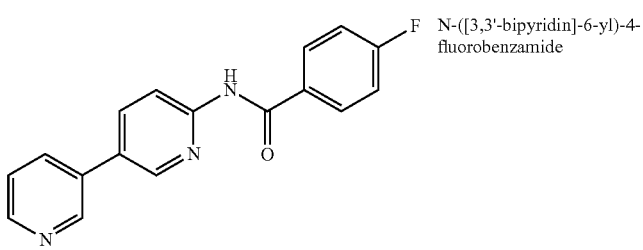 | N-([3,3'-bipyridin]-6-yl)-4-fluorobenzamide |

| Example No. | Compound Structure | Compound Name |
|---|---|---|
| 79 | 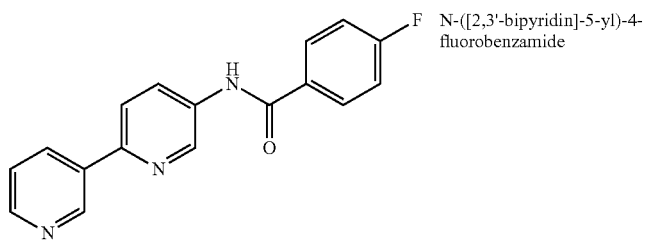 | N-([2,3'-bipyridin]-5-yl)-4-fluorobenzamide |
| 80 | 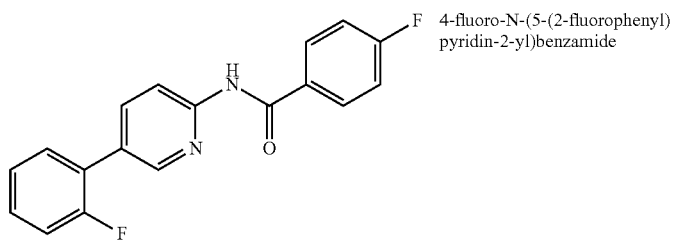 | 4-fluoro-N-(5-(2-fluorophenyl)pyridin-2-yl)benzamide |
| 81 | 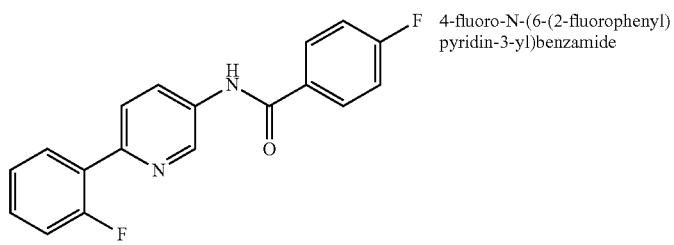 | 4-fluoro-N-(6-(2-fluorophenyl)pyridin-3-yl)benzamide |
| 82 | 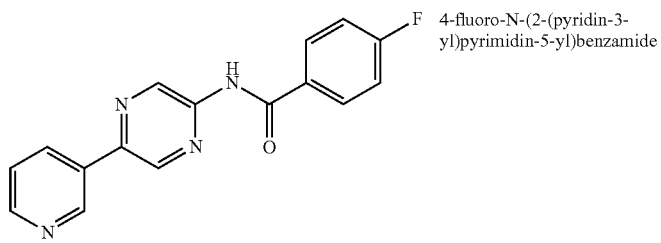 | 4-fluoro-N-(2-(pyridin-3-yl)pyrimidin-5-yl)benzamide |
| 83 | 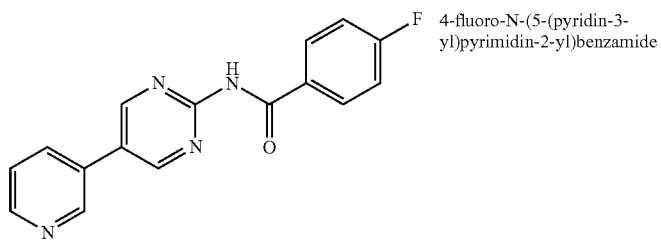 | 4-fluoro-N-(5-(pyridin-3-yl)pyrimidin-2-yl)benzamide |
| 84 | 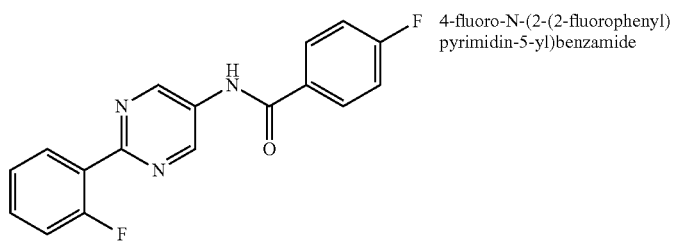 | 4-fluoro-N-(2-(2-fluorophenyl)pyrimidin-5-yl)benzamide |

-continued
| Example No. | Compound Structure | Compound Name |
|---|---|---|
| 85 | 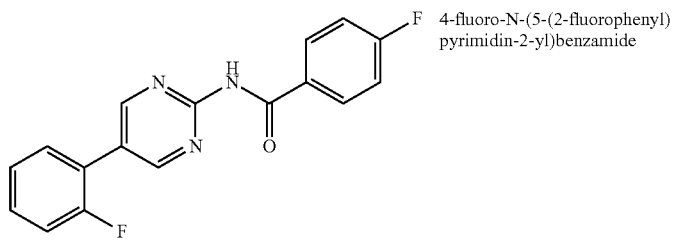 | 4-fluoro-N-(5-(2-fluorophenyl)pyrimidin-2-yl)benzamide |
| 86 | 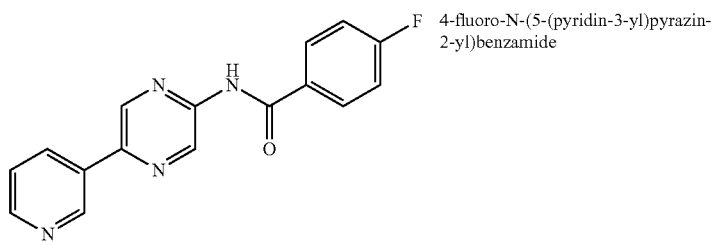 | 4-fluoro-N-(5-(pyridin-3-yl)pyrazin-2-yl)benzamide |
| 87 | 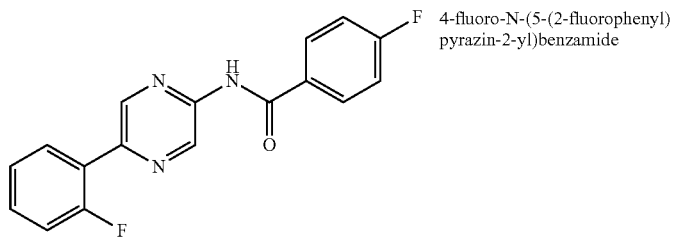 | 4-fluoro-N-(5-(2-fluorophenyl)pyrazin-2-yl)benzamide |
| 88 | 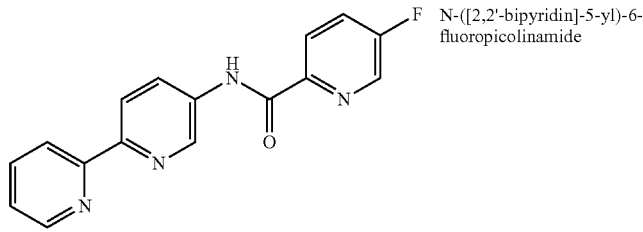 | N-([2,2'-bipyridin]-5-yl)-6-fluoropicolinamide |
| 89 | 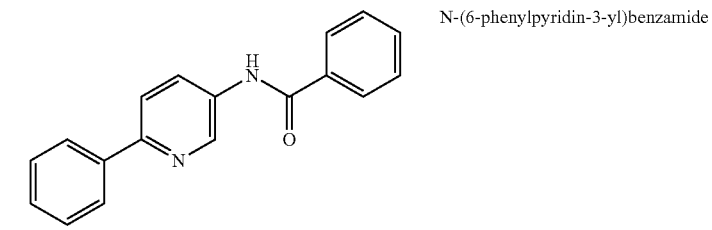 | N-(6-phenylpyridin-3-yl)benzamide |

Example 3: N-([2,3'-bipyridin]-6'-yl)benzamide

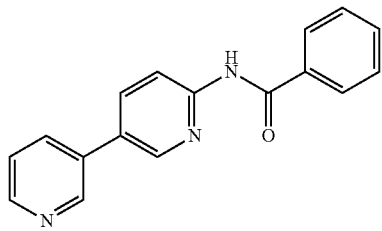 [SMILES: O=C(Nc1ccc(-c2cccnc2)cn1)c1ccccc1]

N-([2,3'-bipyridin]-6'-yl)benzamide was prepared using the general procedure described in Example 1. $^1$H NMR (CDCl$_3$, 400 MHz): δ$_H$ 8.96 (s, 1H), 8.72-8.68 (m, 2H), 8.52 (d, 1H), 8.39 (d, 1H), 7.95-7.91 (m, 2H), 7.82-7.70 (m, 2H), 7.60-7.45 (m, 3H), MS (ESI): m/z 276 (M+H).

Example 18: N-([2,2'-bipyridin]-5-yl)benzamide

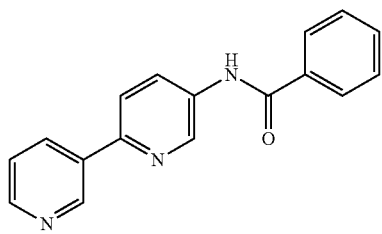 [SMILES: O=C(Nc1ccc(-c2cccnc2)nc1)c1ccccc1]

N-([2,2'-bipyridin]-5-yl)benzamide was prepared using the general procedure described in Example 1. $^1$H NMR (CDCl$_3$, 400 MHz): δ$_H$ 8.82 (d, 1H, J=2.5 Hz), 8.69 (d, 1H, J=4.75 Hz), 8.45-8.35 (m, 2H), 8.10 (d, 1H, J=1.25 Hz), 7.93-7.90 (m, 2H), 7.59-7.47 (m, 3H), 7.32-7.30 (m, 1H), 7.19 (d, 1H, J=1.75 Hz). MS (ESI): m/z 276 (M+H)$^+$.

Example 19: N-([2,2'-bipyridin]-5-yl)-4-fluorobenzamide

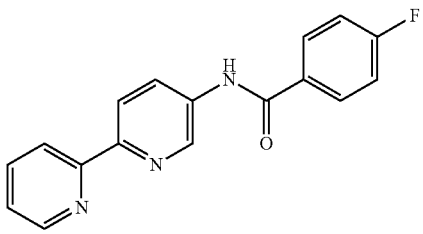 [SMILES: O=C(Nc1ccc(-c2ccccn2)nc1)c1ccc(F)cc1]

N-([2,2'-bipyridin]-5-yl)-4-fluorobenzamide was prepared using the general procedure described in Example 1. $^1$H NMR (DMSO, 400 MHz): δ$_H$ 10.8 (s, 1H), 9.15 (s, 1H), 8.72 (d, 1H, J=4.5 Hz), 8.50-8.45 (m, 3H), 8.19-8.08 (m, 3H), 7.62 (d, 1H, J=6.5 Hz), 7.40 (t, 2H, J=6.5 Hz), MS (ESI): m/z 294 (M+H)$^+$.

Example 20: N-([2,2'-bipyridin]-5-yl)-3-chloro-4-fluorobenzamide

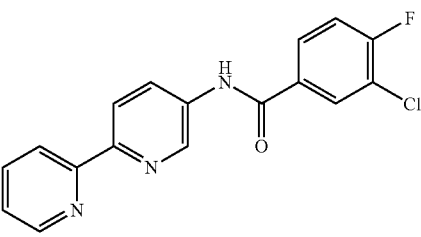

N-([2,2'-bipyridin]-5-yl)-3-chloro-4-fluorobenzamide was prepared using the general procedure described in Example 1. $^1$H NMR (DMSO, 400 MHz): δ$_H$ 11.1 (s, 1H), 9.20 (s, 1H), 8.75 (d, 1H, J=4.5 Hz), 8.53-8.51 (m, 3H), 8.30 (d, 1H, J=7.0 Hz), 8.26 (t, 1H, J=7.5 Hz), 8.11-8.06 (m, 1H), 7.69 (t, 1H, J=7.0 Hz), 7.62 (t, 1H, J=9.0 Hz). MS (ESI): m/z 329 (M+H)$^+$.

Example 21: N-([2,2'-bipyridin]-5-yl)-4-methoxybenzamide

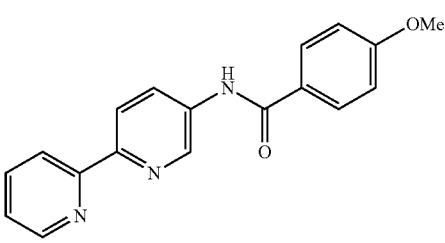

N-([2,2'-bipyridin]-5-yl)-4-methoxybenzamide was prepared using the general procedure described in Example 1. $^1$H NMR (DMSO, 400 MHz): δ$_H$ 10.75 (s, 1H), 9.23 (s, 1H), 8.76 (d, 1H, J=4.5 Hz), 8.55-8.49 (m, 3H), 8.26 (t, 1H, J=7.5 Hz), 8.07-8.03 (m, 2H), 7.69 (d, 1H, J=6.5 Hz), 7.11-7.08 (m, 2H), 3.84 (s, 3H). MS (ESI): m/z 306 (M+H)$^+$.

Example 22: N-([2,2'-bipyridin]-5-yl)-4-chlorobenzamide

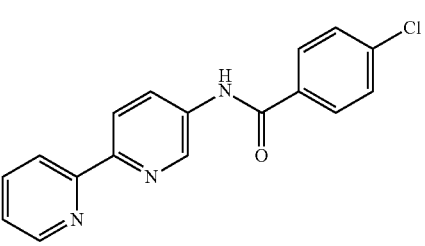

N-([2,2'-bipyridin]-5-yl)-4-chlorobenzamide was prepared using the general procedure described in Example 1. $^1$H NMR (DMSO, 400 MHz): δ$_H$ 10.79 (s, 1H), 9.10 (s, 1H), 8.69 (d, 1H, J=4.5 Hz), 8.45-8.40 (m, 3H), 8.08-8.02 (m, 3H), 7.63 (d, 2H, J=8.5 Hz), 7.53-7.52 (m, 1H). MS (ESI): m/z 311 (M+H)$^+$.

Example 23: N-([2,2'-bipyridin]-5-yl)-3-chlorobenzamide

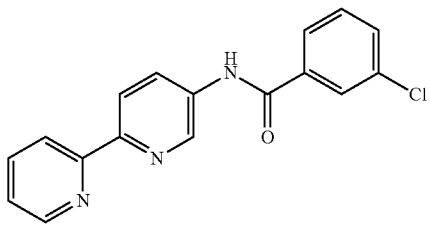 [SMILES: O=C(Nc1ccc(-c2ccccn2)nc1)c1cccc(Cl)c1]

N-([2,2'-bipyridin]-5-yl)-3-chlorobenzamide was prepared using the general procedure described in Example 1. $^1$H NMR (DMSO, 400 MHz): $\delta_H$ 10.9 (s, 1H), 9.16 (s, 1H), 8.74 (d, 1H, J=4.4 Hz), 8.51 (s, 1H), 8.48 (s, 2H), 8.21 (t, 1H, J=7.25 Hz), 8.08 (t, 1H, J=2.0 Hz), 7.98 (d, 1H, J=7.8 Hz), 7.70 (d, 1H, J=9.0 Hz), 7.63-7.58 (m, 2H). MS (ESI): m/z 311 (M+H)$^+$.

Example 33: N-(5-(pyridin-2-yl)pyrazin-2-yl)benzamide

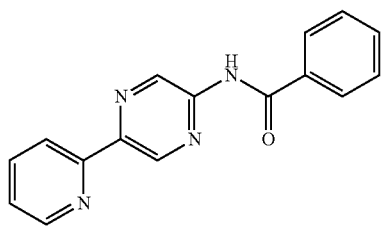

N-(5-(pyridin-2-yl)pyrazin-2-yl)benzamide was prepared using the general procedure described in Example 1. $^1$H NMR (CDCl$_3$, 400 MHz): $\delta_H$ 9.75 (d, 1H, J=1.50 Hz), 9.35 (d, 1H, J=1.50 Hz), 8.69 (d, 1H, J=4.0 Hz), 8.61 (br s, 1H), 8.37 (d, 1H, J=8.0 Hz), 7.97 (m, 2H), 7.84 (t, 1H, J=7.75 Hz), 7.54 (m, 3H), 7.34 (t, 1H, J=6.25 Hz). MS (ESI): m/z 277 (M+H)$^+$.

Example 48: N-(5-(pyridin-2-yl)pyrimidin-2-yl)benzamide

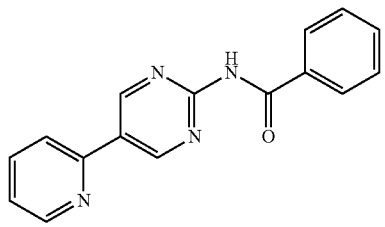 [SMILES: O=C(Nc1ncc(-c2ccccn2)cn1)c1ccccc1]

N-(5-(pyridin-2-yl)pyrimidin-2-yl)benzamide was prepared using the general procedure described in Example 1. $^1$H NMR (CDCl$_3$, 400 MHz): $\delta_H$ 9.28 (s, 2H), 8.73 (d, 1H, J=4.75 Hz), 8.40 (d, 1H, J=8.0 Hz), 7.98-7.97 (m, 2H), 7.82-7.79 (td, 1H, J=7.75 Hz), 7.74-7.65 (m, 3H), 7.53-7.45 (m, 1H). MS (ESI): m/z 277 (M+H)$^+$.

Example 63: N-(2-(pyridin-2-yl)pyrimidin-5-yl)benzamide

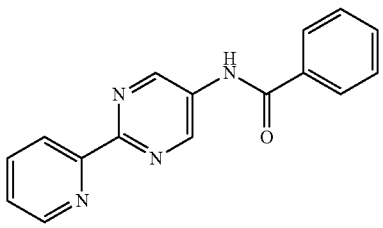

N-(2-(pyridin-2-yl)pyrimidin-5-yl)benzamide was prepared using the general procedure described in Example 1. $^1$H NMR (CDCl$_3$, 400 MHz): $\delta_H$ 9.33 (s, 2H), 8.78 (s, 1H), 8.52 (d, 1H, J=8.0 Hz), 8.27 (br s, 1H), 7.97 (d, 2H, J=7.25 Hz), 7.87 (t, 2H, J=7.0 Hz), 7.63-7.65 (m, 1H), 7.54-7.39 (m, 4H). MS (ESI): m/z 277 (M+H)$^+$.

Example 88: N-([2,2'-bipyridin]-5-yl)-6-fluoropicolinamide

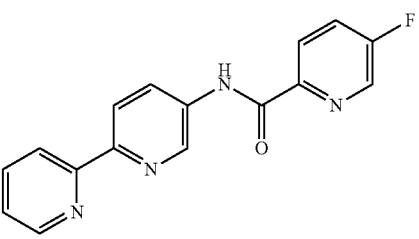 [SMILES: O=C(Nc1ccc(-c2ccccn2)nc1)c1ccc(F)cn1]

N-([2,2'-bipyridin]-5-yl)-6-fluoropicolinamide was prepared using the general procedure described in Example 1. $^1$H NMR (CDCl$_3$, 400 MHz): $\delta_H$ 11.0 (s, 1H), 9.17 (d, 1H, J=2.5 Hz), 8.77 (d, 1H, J=2.5 Hz, 8.67 (d, 1H, J=4.0 Hz), 8.50 (dd, 1H, J=8.75 Hz), 8.37 (dd, 2H, J=8.5 Hz), 8.27 (q, 1H, J=8.5 Hz, H$_1$), 7.96 (d, 2H, J=8.25 Hz), 7.43-7.41 (m, 1H). MS (ESI): m/z 295 (M+H)$^+$.

Example 89: N-(6-phenylpyridin-3-yl)benzamide

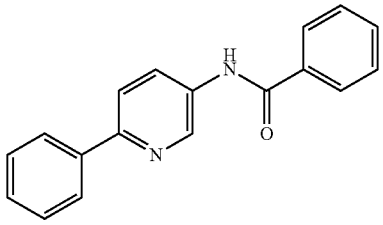

N-(6-phenylpyridin-3-yl)benzamide was prepared using the general procedure described in Example 1. $^1$H NMR (CDCl$_3$, 400 MHz): $\delta_H$ 8.73 (s, 1H), 8.41 (d, 1H, J=2.5 Hz), 7.98 (d, 2H, J=1.5 Hz), 7.95 (s, 1H), 7.91 (d, 2H, J=7.0 Hz), 7.77 (d, 1H, J=8.5 Hz), 7.61-7.38 (m, 6H). MS (ESI): m/z 275 (M+H)$^+$.

Example 90. General Procedure for Synthesis of Ether Analogs

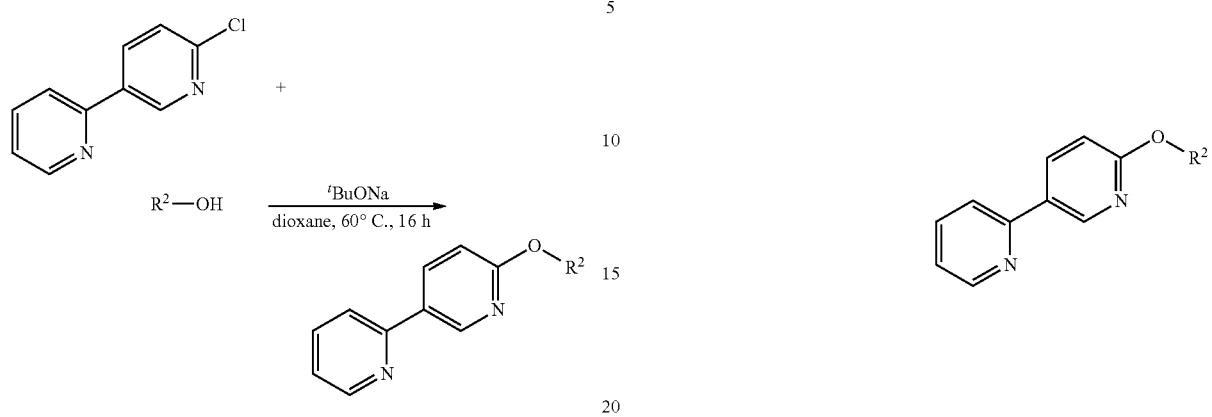

To a solution of an appropriately substituted alcohol (1 mmol) and anhydrous 1,4-dioxane (1 mL) is added sodium tert-butoxide (106 mg, 1.1 mmol). The tube is flushed with argon, capped, and the mixture is stirred at room temperature for five minutes. A solution of 6'-chloro-2,3'-bipyridine (190 mg, 1 mmol) in anhydrous 1,4-dioxane (1 mL) is then added and the mixture is stirred at 60° C. for 16 hours. The mixture is partitioned between ethyl acetate (3×5 mL) and 5% aqueous $NaH_2PO_4$ (5 mL). The organic layer is evaporated and the residue is purified using silica or basic alumina column chromatography and eluted with the appropriate solvent mixtures (e.g., ethyl acetate-methanol-triethylamine, or cyclohexane-ethyl acetate) to give the desired compound.

Example 91. Alternative Procedure for Synthesis of Ether Analogs

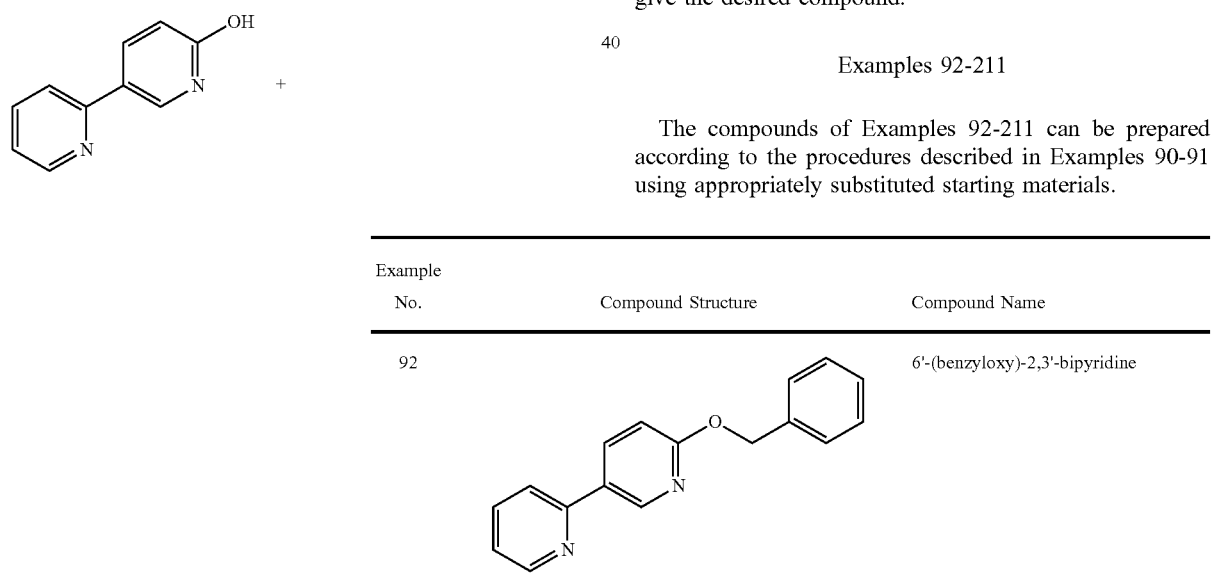

2,2'-Bipyridin-5-ol (138 mg, 0.8 mmol), an appropriately substituted alcohol (0.8 mmol), di-tert-butyl azodicarboxylate, (219 mg, 0.95 mmol) and polymer-bound triphenylphosphine (314 mg, 1.2 mmol) are dissolved in dichloromethane (6 mL). The reaction mixture is heated to 40° C. for 24 hours. The reaction is then diluted with dichloromethane (15 mL), washed with saturated sodium bicarbonate solution and brine. The organic layer is dried with $NaSO_4$ and concentrated in vacuo. The residue is purified using a silica or basic alumina column chromatography and eluted with the appropriate solvent mixtures (e.g., ethyl acetate-methanol-triethylamine, or cyclohexane-ethyl acetate) to give the desired compound.

Examples 92-211

The compounds of Examples 92-211 can be prepared according to the procedures described in Examples 90-91 using appropriately substituted starting materials.

| Example No. | Compound Structure | Compound Name |
|---|---|---|
| 92 | 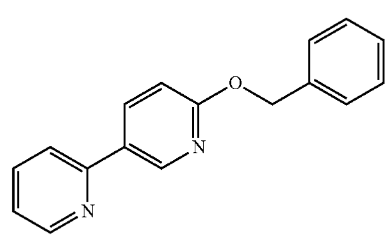 [SMILES: c1ccc(COc2ccc(-c3ccccn3)cn2)cc1] | 6'-(benzyloxy)-2,3'-bipyridine |

| Example No. | Compound Structure | Compound Name |
|---|---|---|
| 93 | 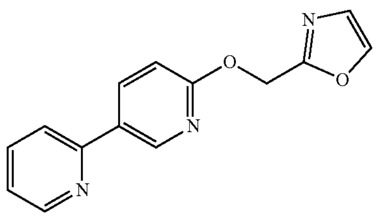 [SMILES: c1ccc(-c2ccc(OCc3ncco3)nc2)nc1] | 2-(([2,3'-bipyridin]-6'-yloxy)methyl)oxazole |
| 94 | 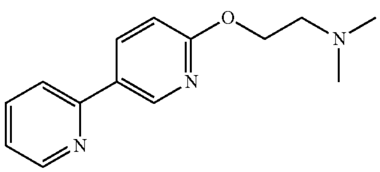 [SMILES: CN(C)CCOc1ccc(-c2ccccn2)cn1] | 2-([2,3'-bipyridin]-6'-yloxy)-N,N-dimethylethan-1-amine |
| 95 | 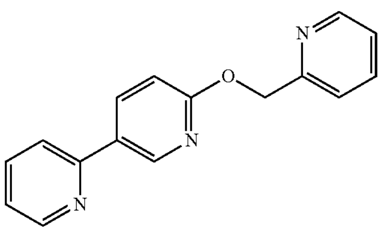 [SMILES: c1ccc(COc2ccc(-c3ccccn3)cn2)nc1] | 6'-(pyridin-2-ylmethoxy)-2,3'-bipyridine |
| 96 | 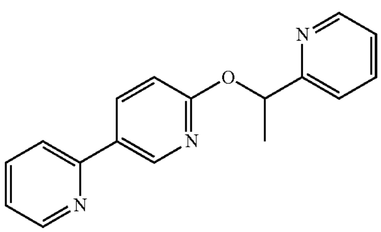 [SMILES: CC(Oc1ccc(-c2ccccn2)cn1)c1ccccn1] | 6'-(1-(pyridin-2-yl)ethoxy)-2,3'-bipyridine |
| 97 | 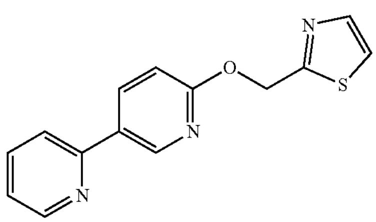 | 2-(([2,3'-bipyridin]-6'-yloxy)methyl)thiazole |
| 98 | 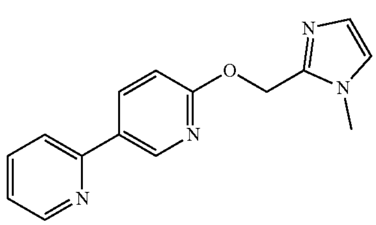 [SMILES: Cn1ccnc1COc1ccc(-c2ccccn2)cn1] | 6'-((1-methyl-1H-imidazol-2-yl)methoxy)-2,3'-bipyridine |
| 99 | 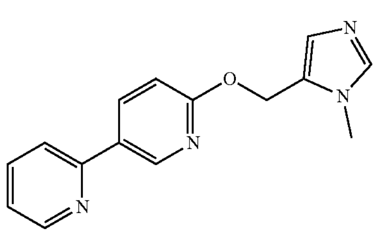 [SMILES: Cn1cncc1COc1ccc(-c2ccccn2)cn1] | 6'-((1-methyl-1H-imidazol-5-yl)methoxy)-2,3'-bipyridine |

-continued

| Example No. | Compound Structure | Compound Name |
|---|---|---|
| 100 | 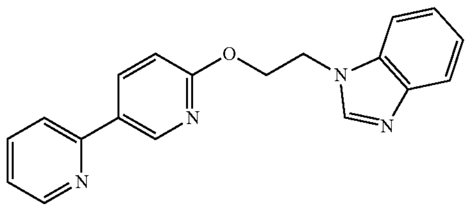 [SMILES: c1ccc(-c2ccc(OCCn3cnc4ccccc43)nc2)nc1] | 1-(2-([2,3'-bipyridin]-6'-yloxy)ethyl)-1H-benzo[d]imidazole |
| 101 | 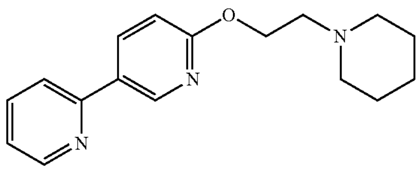 [SMILES: c1ccc(-c2ccc(OCCN3CCCCC3)nc2)nc1] | 6'-(2-(piperidin-1-yl)ethoxy)-2,3'-bipyridine |
| 102 | 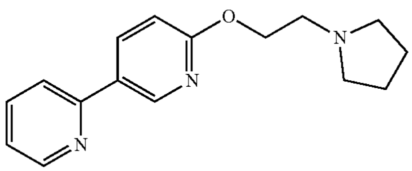 [SMILES: c1ccc(-c2ccc(OCCN3CCCC3)nc2)nc1] | 6'-(2-(pyrrolidin-1-yl)ethoxy)-2,3'-bipyridine |
| 103 | 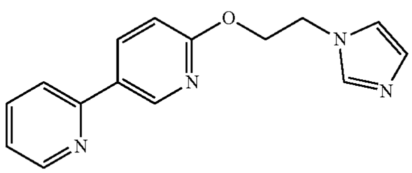 | 6'-(2-(1H-imidazol-1-yl)ethoxy)-2,3'-bipyridine |
| 104 | 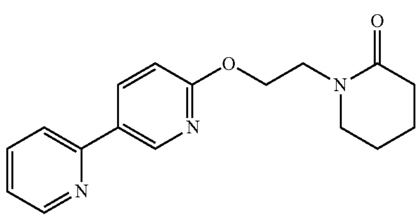 [SMILES: O=C1CCCCN1CCOc1ccc(-c2ccccn2)cn1] | 1-(2-([2,3'-bipyridin]-6'-yloxy)ethyl)piperidin-2-one |
| 105 | 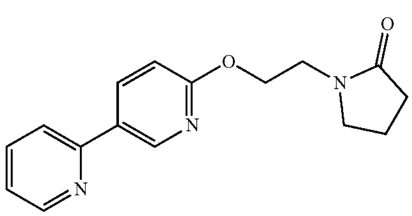 [SMILES: O=C1CCCN1CCOc1ccc(-c2ccccn2)cn1] | 1-(2-([2,3'-bipyridin]-6'-yloxy)ethyl)pyrrolidin-2-one |
| 106 | 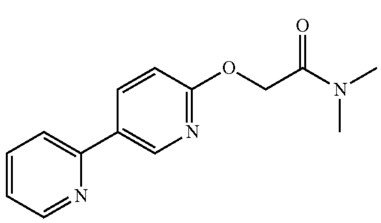 | 2-([2,3'-bipyridin]-6'-yloxy)-N,N-dimethylacetamide |
| 107 | 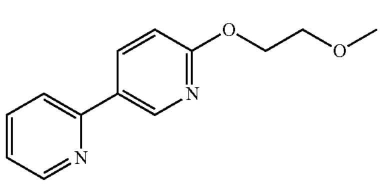 [SMILES: COCCOc1ccc(-c2ccccn2)cn1] | 6'-(2-methoxyethoxy)-2,3'-bipyridine |

-continued

| Example No. | Compound Structure | Compound Name |
|---|---|---|
| 108 | 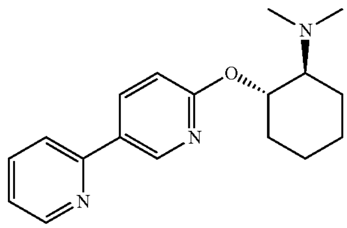 [SMILES: CN(C)[C@H]1CCCC[C@@H]1Oc1ccc(-c2ccccn2)cn1] | (1S,2S)-2-([2,3'-bipyridin]-6'-yloxy)-N,N-dimethylcyclohexan-1-amine |
| 109 | 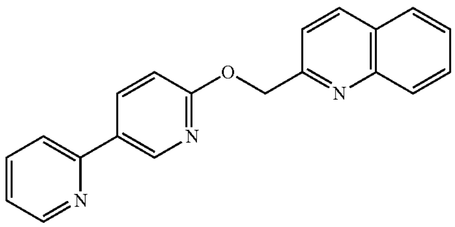 [SMILES: c1ccc(-c2ccc(OCc3ccc4ccccc4n3)nc2)nc1] | 2-(([2,3'-bipyridin]-6'-yloxy)methyl)quinolone |
| 110 | 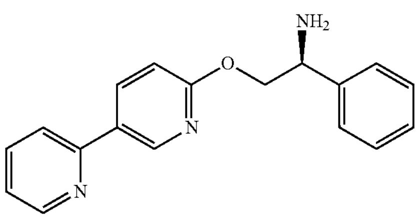 [SMILES: N[C@H](COc1ccc(-c2ccccn2)cn1)c1ccccc1] | (S)-2-([2,3'-bipyridin]-6'-yloxy)-1-phenylethan-1-amine |
| 111 | 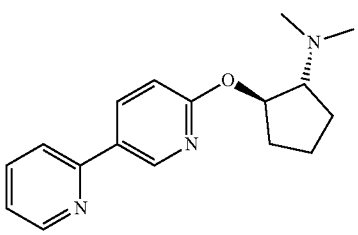 | (1R,2R)-2-([2,3'-bipyridin]-6'-yloxy)-N,N-dimethylcyclopentan-1-amine |
| 112 | 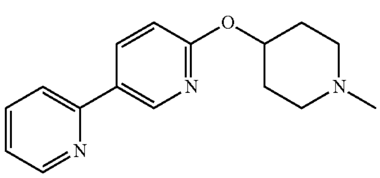 [SMILES: CN1CCC(Oc2ccc(-c3ccccn3)cn2)CC1] | 6'-((1-methylpiperidin-4-yl)oxy)-2,3'-bipyridine |
| 113 | 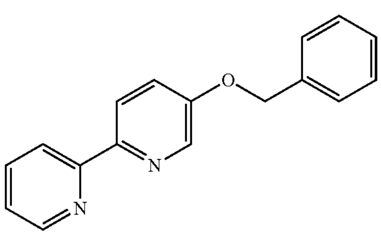 [SMILES: c1ccc(COc2ccc(-c3ccccn3)nc2)cc1] | 5-(benzyloxy)-2,2'-bipyridine |
| 114 | 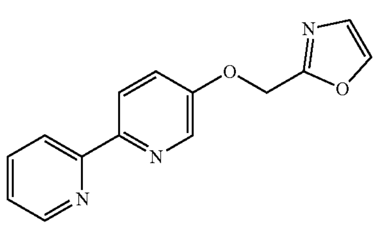 [SMILES: c1ccc(-c2ccc(OCc3ncco3)cn2)nc1] | 2-(([2,2'-bipyridin]-5-yloxy)methyl)oxazole |

-continued

| Example No. | Compound Structure | Compound Name |
|---|---|---|
| 115 | 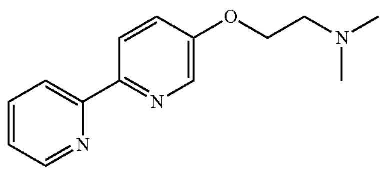 [SMILES: CN(C)CCOc1ccc(-c2ccccn2)nc1] | 2-([2,2'-bipyridin]-5-yloxy)-N,N-dimethylethan-1-amine |
| 116 | 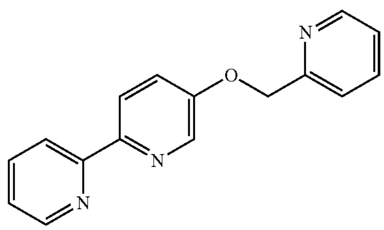 [SMILES: c1ccc(COc2ccc(-c3ccccn3)nc2)nc1] | 5-(pyridin-2-ylmethoxy)-2,2'-bipyridine |
| 117 | 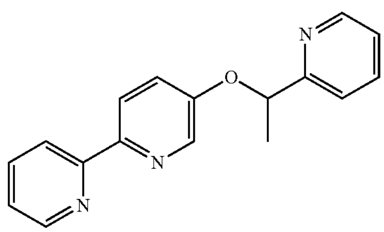 [SMILES: CC(Oc1ccc(-c2ccccn2)nc1)c1ccccn1] | 5-(1-(pyridin-2-yl)ethoxy)-2,2'-bipyridine |
| 118 | 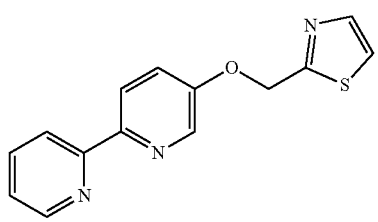 | 2-(([2,2'-bipyridin]-5-yloxy)methyl)thiazole |
| 119 | 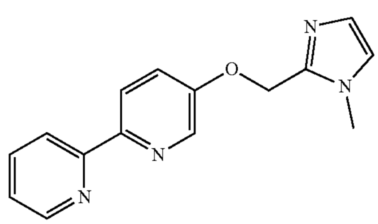 [SMILES: Cn1ccnc1COc1ccc(-c2ccccn2)nc1] | 5-((1-methyl-1H-imidazol-2-yl)methoxy)-2,2'-bipyridine |
| 120 | 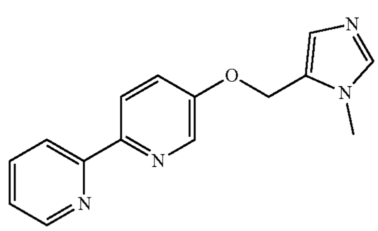 [SMILES: Cn1cncc1COc1ccc(-c2ccccn2)nc1] | 5-((1-methyl-1H-imidazol-5-yl)methoxy)-2,2'-bipyridine |
| 121 | 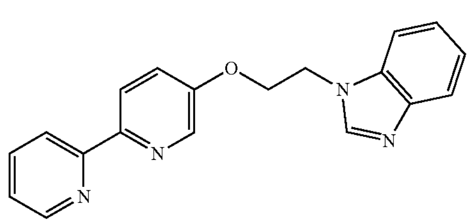 [SMILES: c1ccc(-c2ccc(OCCn3cnc4ccccc43)cn2)nc1] | 1-(2-([2,2'-bipyridin]-5-yloxy)ethyl)-1H-benzo[d]imidazole |

-continued
| Example No. | Compound Structure | Compound Name |
|---|---|---|
| 122 | 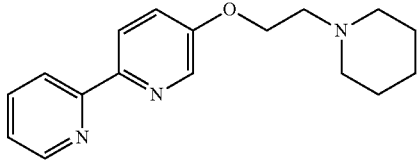 [SMILES: c1ccc(-c2ccc(OCCN3CCCCC3)cn2)nc1] | 5-(2-(piperidin-1-yl)ethoxy)-2,2'-bipyridine |
| 123 | 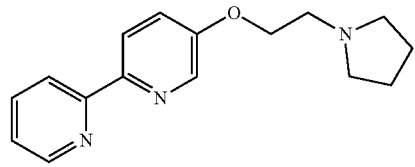 [SMILES: c1ccc(-c2ccc(OCCN3CCCC3)cn2)nc1] | 5-(2-(pyrrolidin-1-yl)ethoxy)-2,2'-bipyridine |
| 124 | 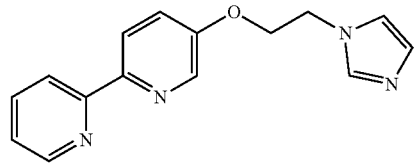 [SMILES: c1ccc(-c2ccc(OCCn3ccnc3)cn2)nc1] | 5-(2-(1H-imidazol-1-yl)ethoxy)-2,2'-bipyridine |
| 125 | 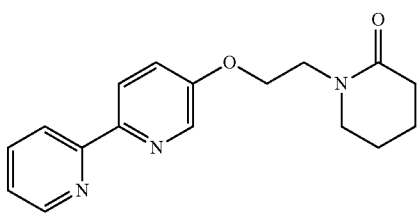 [SMILES: O=C1CCCCN1CCOc1ccc(-c2ccccn2)nc1] | 1-(2-([2,2'-bipyridin]-5-yloxy)ethyl)piperidin-2-one |
| 126 | 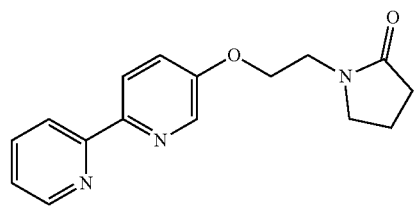 [SMILES: O=C1CCCN1CCOc1ccc(-c2ccccn2)nc1] | 1-(2-([2,2'-bipyridin]-5-yloxy)ethyl)pyrrolidin-2-one |
| 127 | 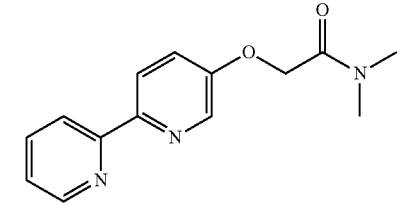 [SMILES: CN(C)C(=O)COc1ccc(-c2ccccn2)nc1] | 2-([2,2'-bipyridin]-5-yloxy)-N,N-dimethylacetamide |
| 128 | 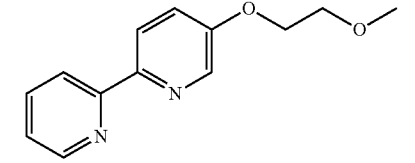 [SMILES: COCCOc1ccc(-c2ccccn2)nc1] | 5-(2-methoxyethoxy)-2,2'-bipyridine |

-continued

| Example No. | Compound Name |
|---|---|
| 129 | (1S,2S)-2-([2,2'-bipyridin]-5-yloxy)-N,N-dimethylcyclohexan-1-amine |
| 130 | 2-(([2,2'-bipyridin]-5-yloxy)methyl)quinolone |
| 131 | (S)-2-([2,2'-bipyridin]-5-yloxy)-1-phenylethan-1-amine |
| 132 | (1R,2R)-2-([2,2'-bipyridin]-5-yloxy)-N,N-dimethylcyclopentan-1-amine |
| 133 | 5-((1-methylpiperidin-4-yl)oxy)-2,2'-bipyridine |
| 134 | 2-(benzyloxy)-5-(pyridin-2-yl)pyrazine |
| 135 | 2-(((5-(pyridin-2-yl)pyrazin-2-yl)oxy)methyl)oxazole |

-continued

| Example No. | Compound Structure | Compound Name |
|---|---|---|
| 136 | 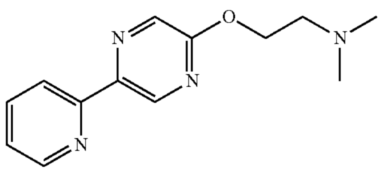 [SMILES: CN(C)CCOc1cnc(-c2ccccn2)cn1] | N,N-dimethyl-2-((5-(pyridin-2-yl)pyrazin-2-yl)oxy)ethan-1-amine |
| 137 | 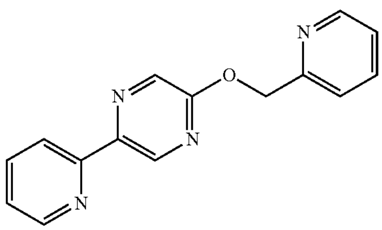 [SMILES: c1ccc(COc2cnc(-c3ccccn3)cn2)nc1] | 2-(pyridin-2-yl)-5-(pyridin-2-ylmethoxy)pyrazine |
| 138 | 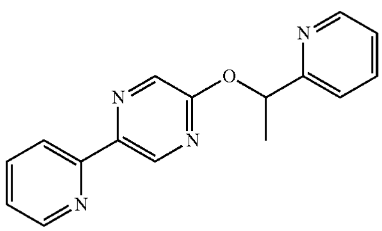 [SMILES: CC(Oc1cnc(-c2ccccn2)cn1)c1ccccn1] | 2-(pyridin-2-yl)-5-(1-(pyridin-2-yl)ethoxy)pyrazine |
| 139 | 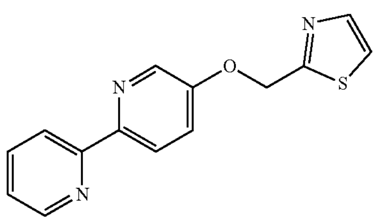 [SMILES: c1ccc(-c2ccc(OCc3nccs3)cn2)nc1] | 2-(((5-(pyridin-2-yl)pyrazin-2-yl)oxy)methyl)thiazole |
| 140 | 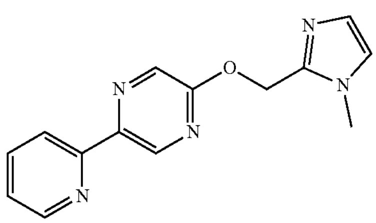 | 2-((1-methyl-1H-imidazol-2-yl)methoxy)-5-(pyridin-2-yl)pyrazine |
| 141 | 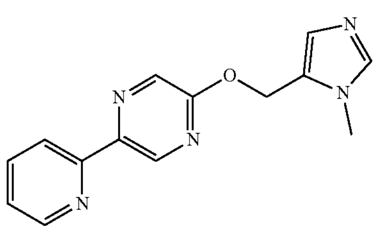 [SMILES: Cn1cncc1COc1cnc(-c2ccccn2)cn1] | 2-((1-methyl-1H-imidazol-5-yl)methoxy)-5-(pyridin-2-yl)pyrazine |
| 142 | 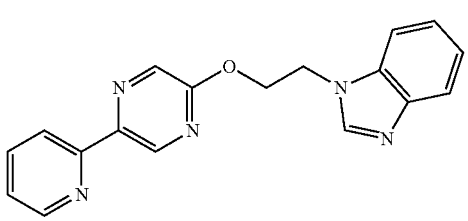 [SMILES: c1ccc(-c2cnc(OCCn3cnc4ccccc43)cn2)nc1] | 1-(2-((5-(pyridin-2-yl)pyrazin-2-yl)oxy)ethyl)-1H-benzo[d]imidazole |

-continued

| Example No. | Compound Structure | Compound Name |
|---|---|---|
| 143 | 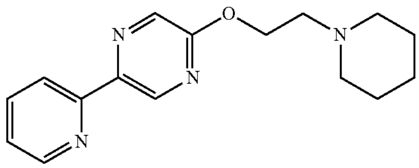 [SMILES: c1ccc(-c2cnc(OCCN3CCCCC3)cn2)nc1] | 2-(2-(piperidin-1-yl)ethoxy)-5-(pyridin-2-yl)pyrazine |
| 144 | 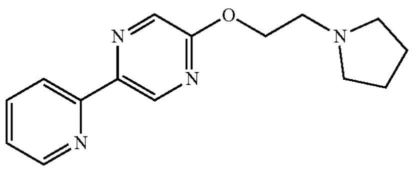 [SMILES: c1ccc(-c2cnc(OCCN3CCCC3)cn2)nc1] | 2-(pyridin-2-yl)-5-(2-(pyrrolidin-1-yl)ethoxy)pyrazine |
| 145 | 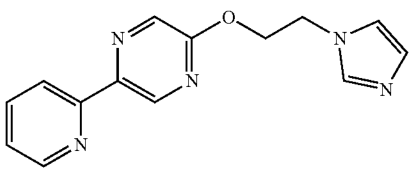 [SMILES: c1ccc(-c2cnc(OCCn3ccnc3)cn2)nc1] | 2-(2-(1H-imidazol-1-yl)ethoxy)-5-(pyridin-2-yl)pyrazine |
| 146 | 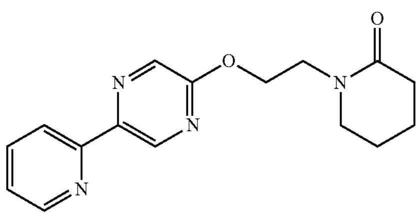 [SMILES: O=C1CCCCN1CCOc1cnc(-c2ccccn2)cn1] | 1-(2-((5-(pyridin-2-yl)pyrazin-2-yl)oxy)ethyl)piperidin-2-one |
| 147 | 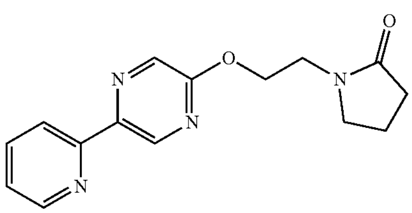 [SMILES: O=C1CCCN1CCOc1cnc(-c2ccccn2)cn1] | 1-(2-((5-(pyridin-2-yl)pyrazin-2-yl)oxy)ethyl)pyrrolidin-2-one |
| 148 | 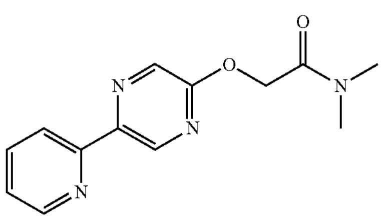 [SMILES: CN(C)C(=O)COc1cnc(-c2ccccn2)cn1] | N,N-dimethyl-2-((5-(pyridin-2-yl)pyrazin-2-yl)oxy)acetamide |
| 149 | 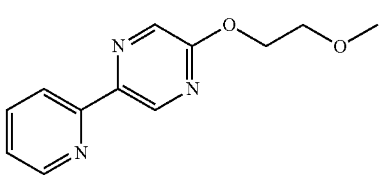 [SMILES: COCCOc1cnc(-c2ccccn2)cn1] | 2-(2-methoxyethoxy)-5-(pyridin-2-yl)pyrazine |
| 150 | 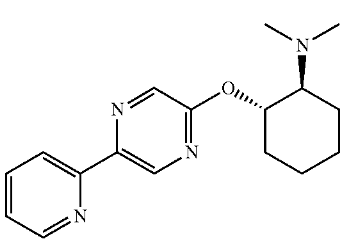 [SMILES: CN(C)[C@H]1CCCC[C@@H]1Oc1cnc(-c2ccccn2)cn1] | (1S,2S)-N,N-dimethyl-2-((5-(pyridin-2-yl)pyrazin-2-yl)oxy)cyclohexan-1-amine |

| Example No. | Compound Structure | Compound Name |
|---|---|---|
| 151 | 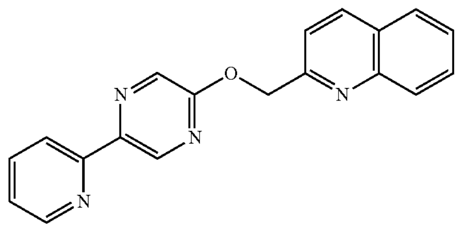 [SMILES: c1ccc(-c2cnc(OCc3ccc4ccccc4n3)cn2)nc1] | 2-(((5-(pyridin-2-yl)pyrazin-2-yl)oxy)methyl)quinolone |
| 152 | 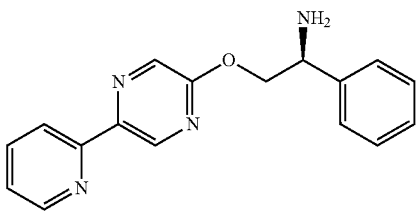 [SMILES: N[C@H](COc1cnc(-c2ccccn2)cn1)c1ccccc1] | (S)-1-phenyl-2-((5-(pyridin-2-yl)pyrazin-2-yl)oxy)ethan-1-amine |
| 153 | 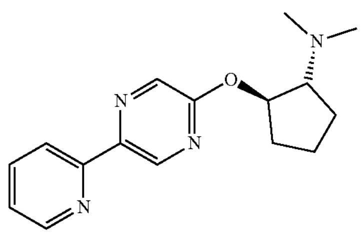 | (1R,2R)-N,N-dimethyl-2-((5-(pyridin-2-yl)pyrazin-2-yl)oxy)cyclopentan-1-amine |
| 154 | 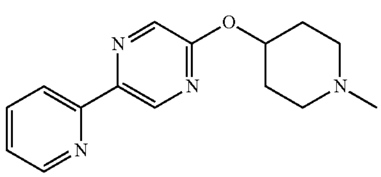 [SMILES: CN1CCC(Oc2cnc(-c3ccccn3)cn2)CC1] | 2-((1-methylpiperidin-4-yl)oxy)-5-(pyridin-2-yl)pyrazine |
| 155 | 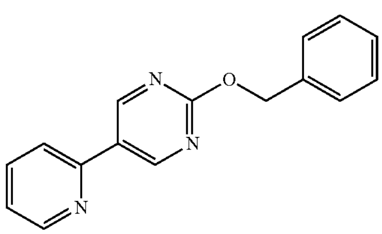 [SMILES: c1ccc(COc2ncc(-c3ccccn3)cn2)cc1] | 2-(benzyloxy)-5-(pyridin-2-yl)pyrimidine |
| 156 | 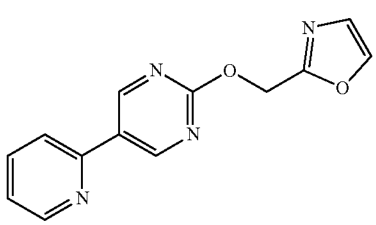 [SMILES: c1ccc(-c2cnc(OCc3ncco3)nc2)nc1] | 2-(((5-(pyridin-2-yl)pyrimidin-2-yl)oxy)methyl)oxazole |
| 157 | 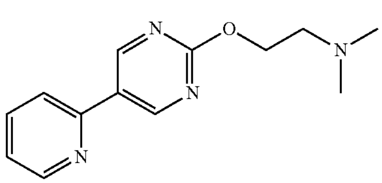 [SMILES: CN(C)CCOc1ncc(-c2ccccn2)cn1] | N,N-dimethyl-2-((5-(pyridin-2-yl)pyrimidin-2-yl)oxy)ethan-1-amine |

-continued

| Example No. | Compound Structure | Compound Name |
|---|---|---|
| 158 | 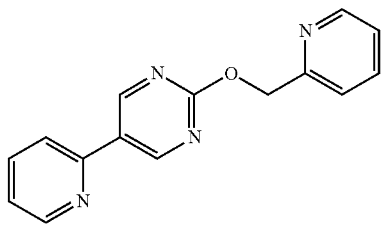 | 5-(pyridin-2-yl)-2-(pyridin-2-ylmethoxy)pyrimidine |
| 159 | 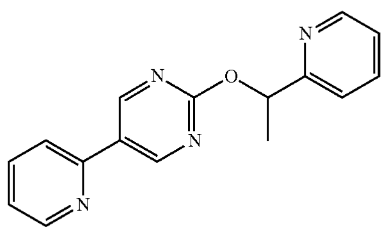 [SMILES: CC(Oc1ncc(-c2ccccn2)cn1)c1ccccn1] | 5-(pyridin-2-yl)-2-(1-(pyridin-2-yl)ethoxy)pyrimidine |
| 160 | 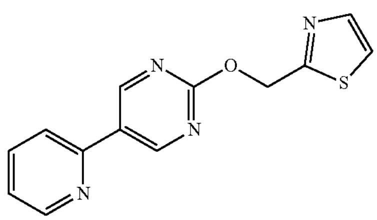 | 2-(((5-(pyridin-2-yl)pyrimidin-2-yl)oxy)methyl)thiazole |
| 161 | 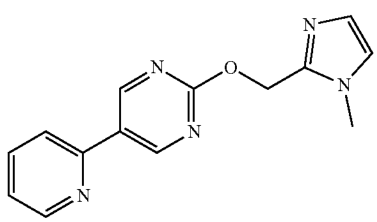 [SMILES: Cn1ccnc1COc1ncc(-c2ccccn2)cn1] | 2-((1-methyl-1H-imidazol-2-yl)methoxy)-5-(pyridin-2-yl)pyrimidine |
| 162 | 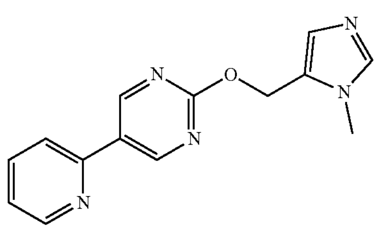 [SMILES: Cn1cncc1COc1ncc(-c2ccccn2)cn1] | 2-((1-methyl-1H-imidazol-5-yl)methoxy)-5-(pyridin-2-yl)pyrimidine |
| 163 | 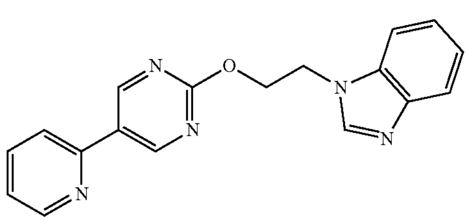 [SMILES: c1ccc(-c2cnc(OCCn3cnc4ccccc43)nc2)nc1] | 1-(2-((5-(pyridin-2-yl)pyrimidin-2-yl)oxy)ethyl)-1H-benzo[d]imidazole |
| 164 | 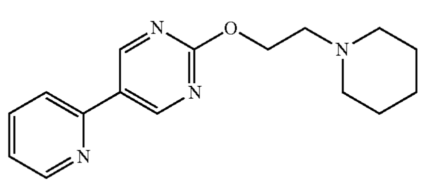 [SMILES: c1ccc(-c2cnc(OCCN3CCCCC3)nc2)nc1] | 2-(2-(piperidin-1-yl)ethoxy)-5-(pyridin-2-yl)pyrimidine |

| Example No. | Compound Structure | Compound Name |
|---|---|---|
| 165 | 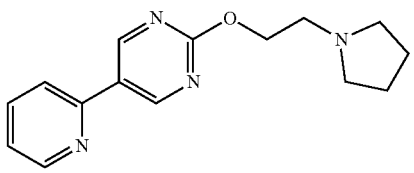 [SMILES: c1ccc(-c2cnc(OCCN3CCCC3)nc2)nc1] | 5-(pyridin-2-yl)-2-(2-(pyrrolidin-1-yl)ethoxy)pyrimidine |
| 166 | 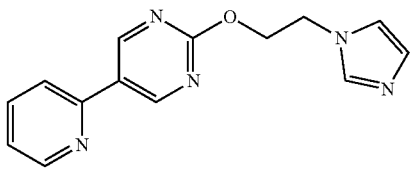 [SMILES: c1ccc(-c2cnc(OCCn3ccnc3)nc2)nc1] | 2-(2-(1H-imidazol-1-yl)ethoxy)-5-(pyridin-2-yl)pyrimidine |
| 167 | 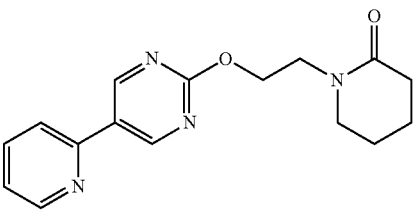 [SMILES: O=C1CCCCN1CCOc1ncc(-c2ccccn2)cn1] | 1-(2-((5-(pyridin-2-yl)pyrimidin-2-yl)oxy)ethyl)piperidin-2-one |
| 168 | 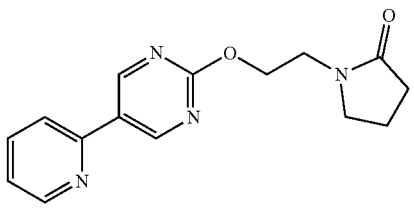 | 1-(2-((5-(pyridin-2-yl)pyrimidin-2-yl)oxy)ethyl)pyrrolidin-2-one |
| 169 | 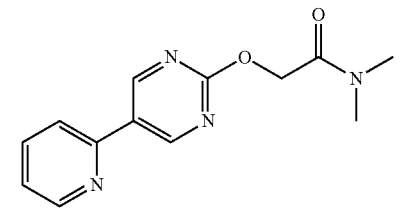 [SMILES: CN(C)C(=O)COc1ncc(-c2ccccn2)cn1] | N,N-dimethyl-2-((5-(pyridin-2-yl)pyrimidin-2-yl)oxy)acetamide |
| 170 | 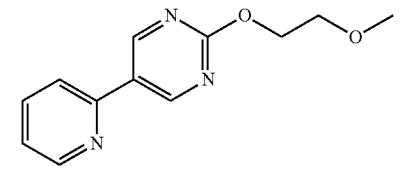 [SMILES: COCCOc1ncc(-c2ccccn2)cn1] | 2-(2-methoxyethoxy)-5-(pyridin-2-yl)pyrimidine |
| 171 | 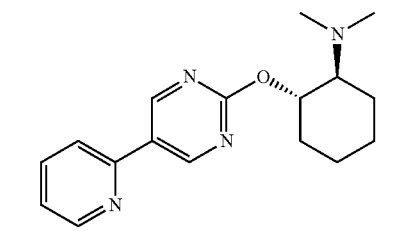 [SMILES: CN(C)[C@H]1CCCC[C@@H]1Oc1ncc(-c2ccccn2)cn1] | (1S,2S)-N,N-dimethyl-2-((5-(pyridin-2-yl)pyrimidin-2-yl)oxy)cyclohexan-1-amine |

| Example No. | Compound Structure | Compound Name |
|---|---|---|
| 172 | 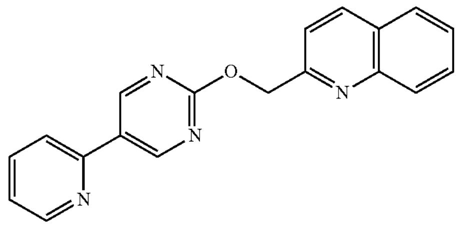 [SMILES: c1ccc(-c2cnc(OCc3ccc4ccccc4n3)nc2)nc1] | 2-(((5-(pyridin-2-yl)pyrimidin-2-yl)oxy)methyl)quinolone |
| 173 | 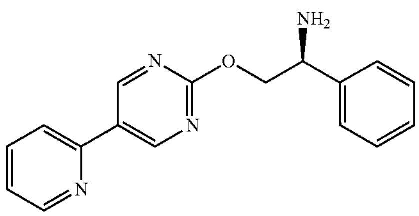 [SMILES: N[C@H](COc1ncc(-c2ccccn2)cn1)c1ccccc1] | (S)-1-phenyl-2-((5-(pyridin-2-yl)pyrimidin-2-yl)oxy)ethan-1-amine |
| 174 | 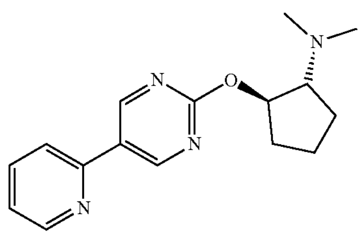 | (1R,2R)-N,N-dimethyl-2-((5-(pyridin-2-yl)pyrimidin-2-yl)oxy)cyclopentan-1-amine |
| 175 | 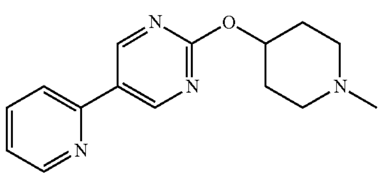 [SMILES: CN1CCC(Oc2ncc(-c3ccccn3)cn2)CC1] | 2-((1-methylpiperidin-4-yl)oxy)-5-(pyridin-2-yl)pyrimidine |
| 176 | 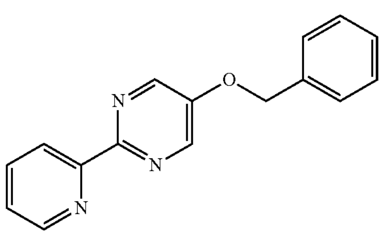 [SMILES: c1ccc(COc2cnc(-c3ccccn3)nc2)cc1] | 5-(benzyloxy)-2-(pyridin-2-yl)pyrimidine |
| 177 | 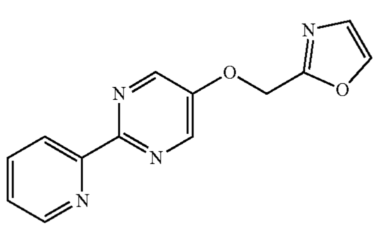 [SMILES: c1ccc(-c2ncc(OCc3ncco3)cn2)nc1] | 2-(((2-(pyridin-2-yl)pyrimidin-5-yl)oxy)methyl)oxazole |
| 178 | 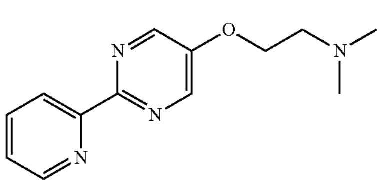 [SMILES: CN(C)CCOc1cnc(-c2ccccn2)nc1] | N,N-dimethyl-2-((2-(pyridin-2-yl)pyrimidin-5-yl)oxy)ethan-1-amine |

-continued

| Example No. | Compound Structure | Compound Name |
|---|---|---|
| 179 | 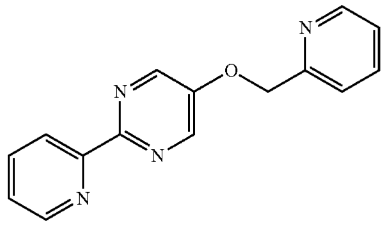 | 2-(pyridin-2-yl)-5-(pyridin-2-ylmethoxy)pyrimidine |
| 180 | 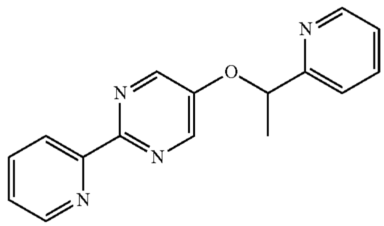 | 2-(pyridin-2-yl)-5-(1-(pyridin-2-yl)ethoxy)pyrimidine |
| 181 | 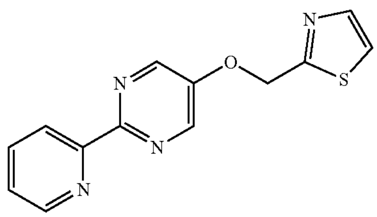 | 2-(((2-(pyridin-2-yl)pyrimidin-5-yl)oxy)methyl)thiazole |
| 182 | 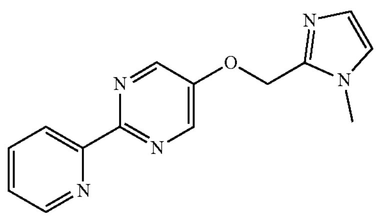 [SMILES: Cn1ccnc1COc1cnc(-c2ccccn2)nc1] | 5-((1-methyl-1H-imidazol-2-yl)methoxy)-2-(pyridin-2-yl)pyrimidine |
| 183 | 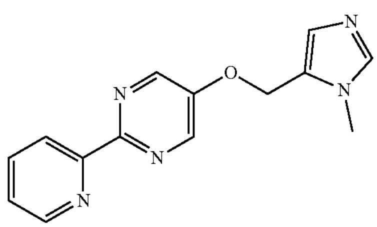 [SMILES: Cn1cncc1COc1cnc(-c2ccccn2)nc1] | 5-((1-methyl-1H-imidazol-5-yl)methoxy)-2-(pyridin-2-yl)pyrimidine |
| 184 | 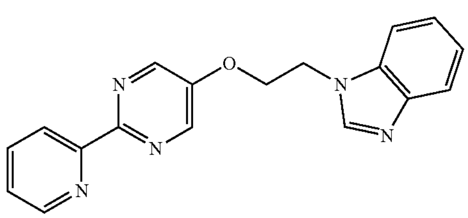 [SMILES: c1ccc(-c2ncc(OCCn3cnc4ccccc43)cn2)nc1] | 1-(2-((2-(pyridin-2-yl)pyrimidin-5-yl)oxy)ethyl)-1H-benzo[d]imidazole |
| 185 | 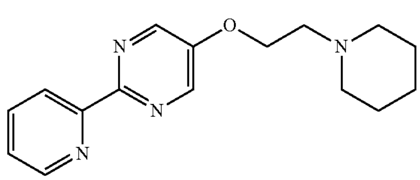 | 5-(2-(piperidin-1-yl)ethoxy)-2-(pyridin-2-yl)pyrimidine |

-continued

| Example No. | Compound Structure | Compound Name |
|---|---|---|
| 186 | 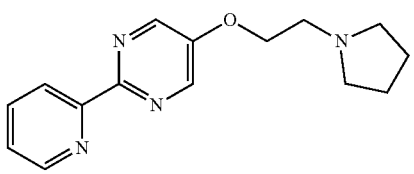 [SMILES: c1ccc(-c2ncc(OCCN3CCCC3)cn2)nc1] | 2-(pyridin-2-yl)-5-(2-(pyrrolidin-1-yl)ethoxy)pyrimidine |
| 187 | 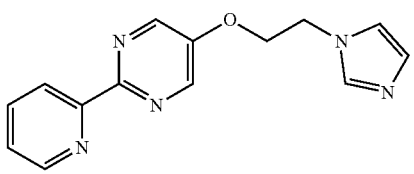 [SMILES: c1ccc(-c2ncc(OCCn3ccnc3)cn2)nc1] | 5-(2-(1H-imidazol-1-yl)ethoxy)-2-(pyridin-2-yl)pyrimidine |
| 188 | 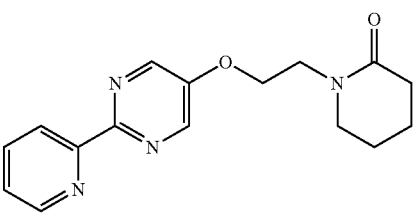 [SMILES: O=C1CCCCN1CCOc1cnc(-c2ccccn2)nc1] | 1-(2-((2-(pyridin-2-yl)pyrimidin-5-yl)oxy)ethyl)piperidin-2-one |
| 189 | 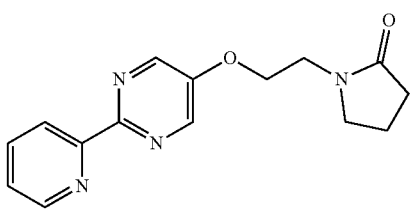 [SMILES: O=C1CCCN1CCOc1cnc(-c2ccccn2)nc1] | 1-(2-((2-(pyridin-2-yl)pyrimidin-5-yl)oxy)ethyl)pyrrolidin-2-one |
| 190 | 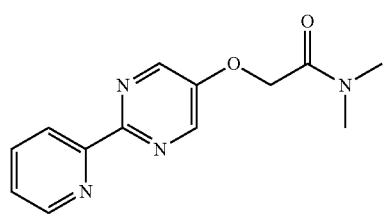 [SMILES: CN(C)C(=O)COc1cnc(-c2ccccn2)nc1] | N,N-dimethyl-2-((2-(pyridin-2-yl)pyrimidin-5-yl)oxy)acetamide |
| 191 | 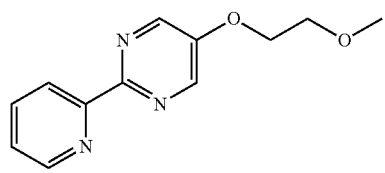 [SMILES: COCCOc1cnc(-c2ccccn2)nc1] | 5-(2-methoxyethoxy)-2-(pyridin-2-yl)pyrimidine |
| 192 | 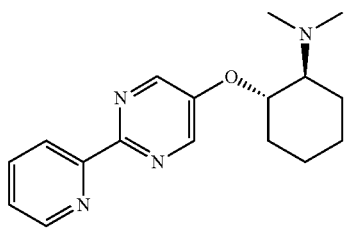 [SMILES: CN(C)[C@H]1CCCC[C@@H]1Oc1cnc(-c2ccccn2)nc1] | (1S,2S)-N,N-dimethyl-2-((2-(pyridin-2-yl)pyrimidin-5-yl)oxy)cyclohexan-1-amine |

-continued

| Example No. | Compound Structure | Compound Name |
|---|---|---|
| 193 | 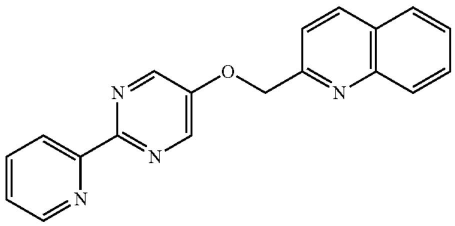 [SMILES: c1ccc(-c2ncc(OCc3ccc4ccccc4n3)cn2)nc1] | 2-(((2-(pyridin-2-yl)pyrimidin-5-yl)oxy)methyl)quinolone |
| 194 | 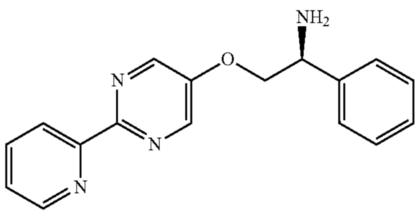 [SMILES: N[C@H](COc1cnc(-c2ccccn2)nc1)c1ccccc1] | (S)-1-phenyl-2-((2-(pyridin-2-yl)pyrimidin-5-yl)oxy)ethan-1-amine |
| 195 | 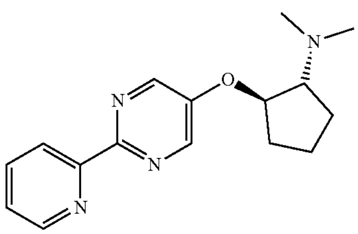 | (1R,2R)-N,N-dimethyl-2-((2-(pyridin-2-yl)pyrimidin-5-yl)oxy)cyclopentan-1-amine |
| 196 | 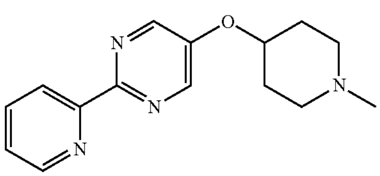 [SMILES: CN1CCC(Oc2cnc(-c3ccccn3)nc2)CC1] | 5-((1-methylpiperidin-4-yl)oxy)-2-(pyridin-2-yl)pyrimidine |
| 197 | 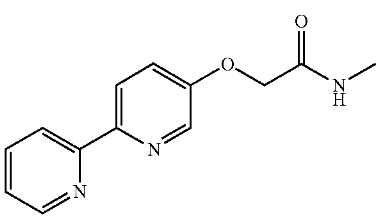 [SMILES: CNC(=O)COc1ccc(-c2ccccn2)nc1] | 2-([2,2'-bipyridin]-5-yloxy)-N-methylacetamide |
| 198 | 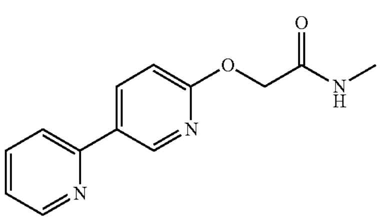 [SMILES: CNC(=O)COc1ccc(-c2ccccn2)cn1] | 2-([2,3'-bipyridin]-6'-yloxy)-N-methylacetamide |
| 199 | 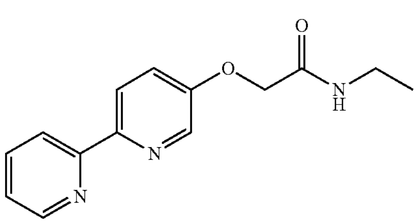 [SMILES: CCNC(=O)COc1ccc(-c2ccccn2)nc1] | 2-([2,2'-bipyridin]-5-yloxy)-N-ethylacetamide |

-continued

| Example No. | Compound Structure | Compound Name |
|---|---|---|
| 200 | 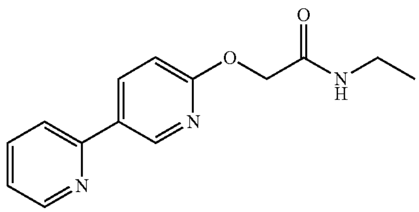 [SMILES: CCNC(=O)COc1ccc(-c2ccccn2)cn1] | 2-([2,3'-bipyridin]-6'-yloxy)-N-ethylacetamide |
| 201 | 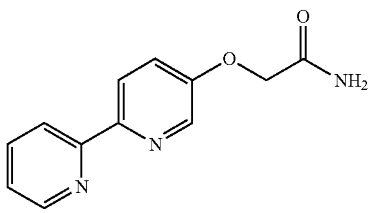 [SMILES: NC(=O)COc1ccc(-c2ccccn2)nc1] | 2-([2,2'-bipyridin]-5-yloxy)acetamide |
| 202 | 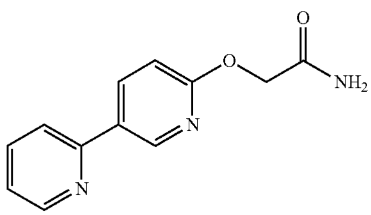 | 2-([2,3'-bipyridin]-6'-yloxy)acelamide |
| 203 | 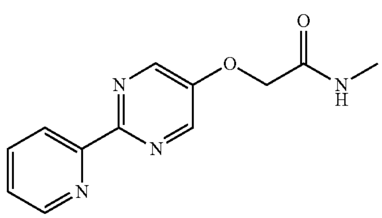 [SMILES: CNC(=O)COc1cnc(-c2ccccn2)nc1] | N-methyl-2-((2-(pyridin-2-yl)pyrimidin-5-yl)oxy)acetamide |
| 204 | 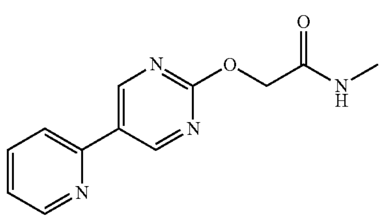 | N-methyl-2-((5-(pyridin-2-yl)pyrimidin-2-yl)oxy)acetamide |
| 205 | 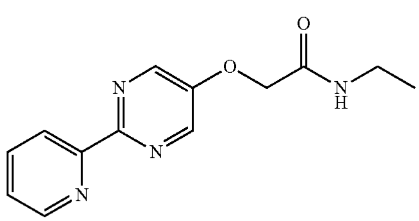 | N-ethyl-2-((2-(pyridin-2-yl)pyrimidin-5-yl)oxy)acetamide |
| 206 | 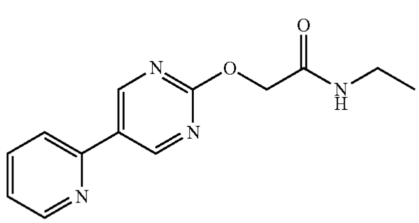 [SMILES: CCNC(=O)COc1ncc(-c2ccccn2)cn1] | N-ethyl-2-((5-(pyridin-2-yl)pyrimidin-2-yl)oxy)acetamide |

| Example No. | Compound Structure | Compound Name |
|---|---|---|
| 207 | 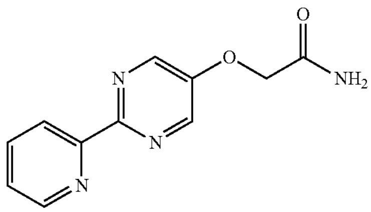 | 2-((2-(pyridin-2-yl)pyrimidin-5-yl)oxy)acetamide |
| 208 | 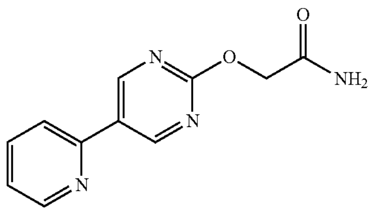 [SMILES: NC(=O)COc1ncc(-c2ccccn2)cn1] | 2-((5-(pyridin-2-yl)pyrimidin-2-yl)oxy)acetamide |
| 209 | 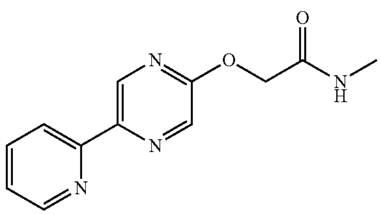 [SMILES: CNC(=O)COc1cnc(-c2ccccn2)cn1] | N-methyl-2-((5-(pyridin-2-yl)pyrazin-2-yl)oxy)acetamide |
| 210 | 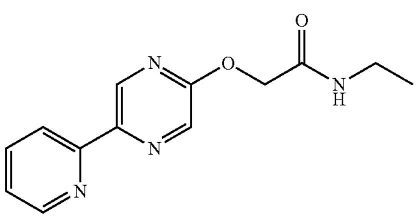 [SMILES: CCNC(=O)COc1cnc(-c2ccccn2)cn1] | N-ethyl-2-((5-(pyridin-2-yl)pyrazin-2-yl)oxy)acetamide |
| 211 | 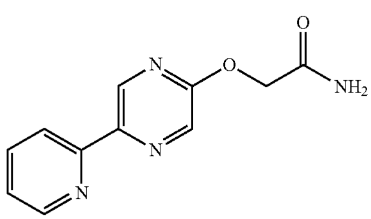 [SMILES: NC(=O)COc1cnc(-c2ccccn2)cn1] | 2-((5-(pyridin-2-yl)pyrazin-2-yl)oxy)acetamide |
| 212 | 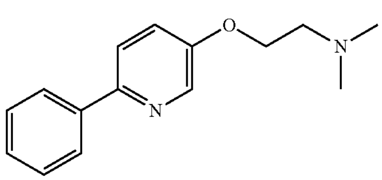 [SMILES: CN(C)CCOc1ccc(-c2ccccc2)nc1] | N,N-dimethyl-2-((6-phenylpyridin-3-yl)oxy)ethan-1-amine |
| 213 | 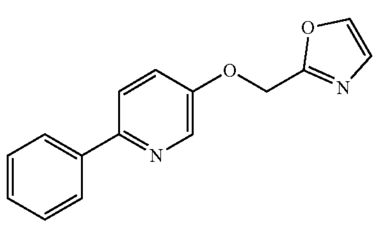 [SMILES: c1ccc(-c2ccc(OCc3ncco3)cn2)cc1] | 2-(((6-phenylpyridin-3-yl)oxy)methyl)oxazole |

Example 94: 2-([2,3'-bipyridin]-6'-yloxy)-N,N-dimethylethan-1-amine

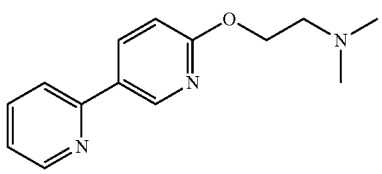

2-([2,3'-bipyridin]-6'-yloxy)-N,N-dimethylethan-1-amine was prepared using the general procedure described in Example 90. $^1$H NMR (CDCl$_3$, 400 MHz): $\delta_H$ 8.73 (s, 1H), 8.65 (d, 1H), 8.22 (d, 1H), 7.78-7.71 (m, 1H), 7.69-7.62 (m, 1H), 7.15-7.00 (m, 1H), 6.85 (d, 1H), 4.46 (m, 2H), 2.76 (m, 2H), 2.38 (s, 6H). MS (ESI): m/z 244 (M+H)$^+$.

Example 136: N,N-dimethyl-2-((5-(pyridin-2-yl)pyrazin-2-yl)oxy)ethan-1-amine

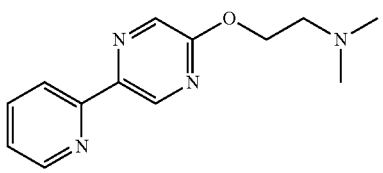

N,N-dimethyl-2-((5-(pyridin-2-yl)pyrazin-2-yl)oxy)ethan-1-amine was prepared using the general procedure described in Example 90. $^1$H NMR (CDCl$_3$, 400 MHz): $\delta_H$ 9.11 (d, 1H, J=1.25 Hz), 8.65 (d, 1H, J=4.25 Hz), 8.30 (d, 1H, J=1.25 Hz), 8.21 (d, 1H, J=8.0 Hz), 7.78 (t, 1H, J=7.75 Hz), 7.28-7.26 (m, 1H), 4.50 (t, 2H, J=5.5 Hz), 2.75 (t, 2H, J=5.5 Hz), 2.35 (s, 6H). MS (ESI): m/z 245 (M+H)$^+$.

Example 157: N,N-dimethyl-2-((5-(pyridin-2-yl)pyrimidin-2-yl)oxy)ethan-1-amine

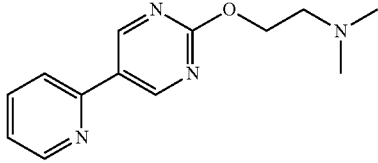 [SMILES: CN(C)CCOc1ncc(-c2ccccn2)cn1]

N,N-dimethyl-2-((5-(pyridin-2-yl)pyrimidin-2-yl)oxy)ethan-1-amine was prepared using the general procedure described in Example 90. $^1$H NMR (CDCl$_3$, 400 MHz): $\delta_H$ 9.12 (s, 2H), 8.71-8.69 (m, 1H), 7.82-7.78 (m, 1H), 7.68 (d, 1H, J=8.0 Hz), 7.32-7.25 (m, 1H), 4.91 (t, 2H, J=5.0 Hz), 3.41 (t, 2H, J=5.0 Hz), 2.84 (s, 6H). MS (ESI): m/z 245 (M+H)$^+$.

Example 212: N,N-dimethyl-2-((6-phenylpyridin-3-yl)oxy)ethan-1-amine

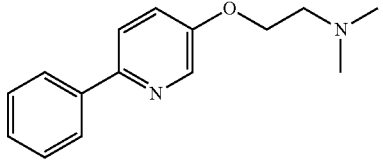 [SMILES: CN(C)CCOc1ccc(-c2ccccc2)nc1]

N,N-dimethyl-2-((6-phenylpyridin-3-yl)oxy)ethan-1-amine was prepared using the general procedure described in Example 91. $^1$H NMR (CDCl$_3$, 400 MHz): $\delta_H$ 8.40 (d, 1H, J=3.0 Hz), 7.91 (d, 2H, J=7.5 Hz), 7.63 (d, 1H, J=8.5 Hz), 7.44-7.34 (m, 3H), 7.28-7.25 (m, 1H), 4.12 (t, 2H, J=5.65 Hz), 2.75 (t, 2H, J=5.65 Hz), 2.23 (s, 6H). MS (ESI): m/z 243 (M+H)$^+$.

Example 213: 2-(((6-phenylpyridin-3-yl)oxy)methyl)oxazole

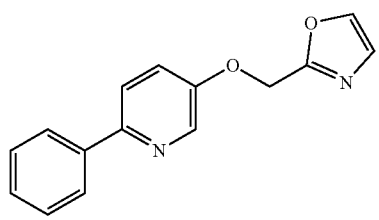 [SMILES: c1ccc(-c2ccc(OCc3ncco3)cn2)cc1]

2-(((6-phenylpyridin-3-yl)oxy)methyl)oxazole was prepared using the general procedure described in Example 91. $^1$H NMR (CDCl$_3$, 400 MHz): $\delta_H$ 8.65 (d, 1H, J=3.0 Hz), 7.92 (d, 2H, J=8.5 Hz), 7.71 (s, 1H), 7.68 (d, 1H, J=8.8 Hz), 7.46-7.37 (m, 4H), 7.17 (s, 1H), 5.24 (s, 2H). MS (ESI): m/z 253 (M+H)$^+$.

Example 214. General Procedure for Synthesis of Amine Analogs

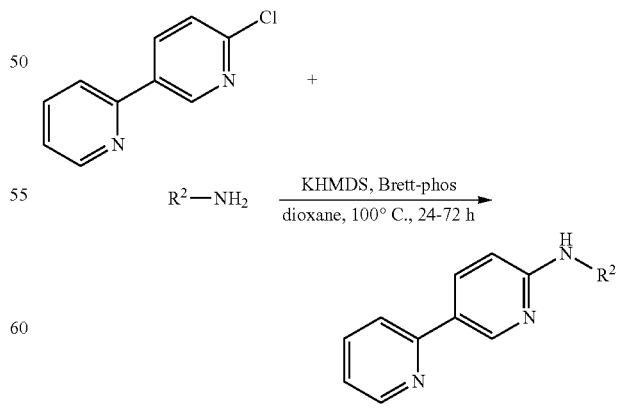

A mixture of 6'-chloro-2,3'-bipyridine (95 mg, 0.5 mmol) an appropriately substituted amine (1 mmol) in anhydrous 1,4-dioxane (5 mL), and potassium bis(trimethylsilyl)amide (KHMDS, 263 mg, 1.3 mmol) is purged with argon for 10-15 minutes. 2-(Dicyclohexylphosphino)3,6-dimethoxy-2',4',6'-triisopropyl-1,1'-biphenyl (Brett-phos, 13.7 mg, 1.5 mol %) is added and the reaction mixture is stirred and heated at 100° C. for 24-72 hours. The solution is cooled, saturated aqueous NaHCO₃ (10 mL) and dichloromethane (25 mL) are added, and the phases are separated. The aqueous phase is extracted with dichloromethane (2×25 mL). The combined organics are dried with Na₂SO₄ and evaporated. The residue is purified using a silica or basic alumina column chromatography and eluted with the appropriate solvent mixtures (e.g., ethyl acetate-methanol-triethylamine, or cyclohexane-ethyl acetate) to give the desired compound.

Example 215. Alternative Procedure for Synthesis of Amine Analogs

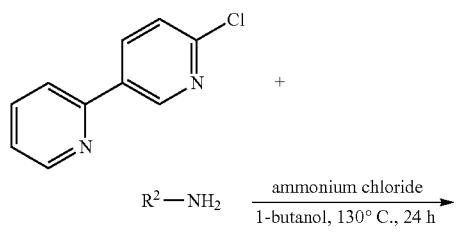

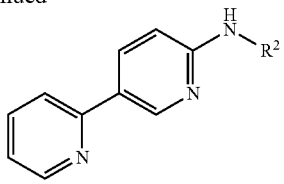

6'-chloro-2,3'-bipyridine (95 mg, 0.5 mmol), ammonium chloride (31.1 mg, 0.58 mmol) and an appropriately substituted amine (2.5 mmol) in 1-butanol (5 mL) are heated to 130° C. for 24 hours. The solvent is removed in vacuo and the residue is then partitioned between ethyl acetate and water (2:1, 15 mL). The aqueous layer is then extracted with EtOAc (2×5 mL) and the organic fractions combined and dried over Na₂SO₄. The reaction mixture is filtered and concentrated in vacuo. The residue is purified using a silica or basic alumina column chromatography and eluted with the appropriate solvent mixtures (e.g., ethyl acetate-methanol-triethylamine, or cyclohexane-ethyl acetate) to give the desired compound.

Examples 216-275

The compounds of Examples 216-275 can be prepared according to the procedures described in Examples 214-215 using appropriately substituted starting materials.

| Example No. | Compound Structure | Compound Name |
|---|---|---|
| 216 | 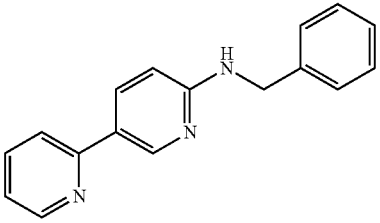 | N-benzyl-[2,3'-bipyridin]-6'-amine |
| 217 | 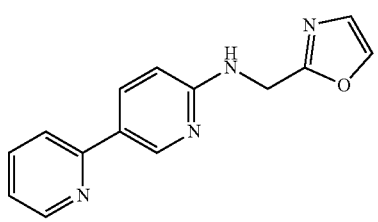 [SMILES: c1ccc(-c2ccc(NCc3ncco3)nc2)nc1] | N-(oxazol-2-ylmethyl)-[2,3'-bipyridin]-6'-amine |
| 218 | 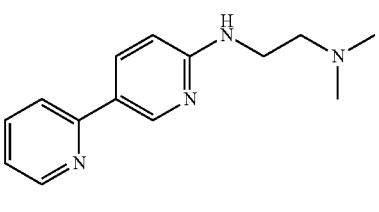 [SMILES: CN(C)CCNc1ccc(-c2ccccn2)cn1] | N1-([2,3'-bipyridin]-6'-yl)-N2,N2-dimethylethane-1,2-diamine |
| 219 | 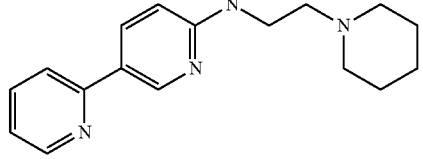 | N-(2-(piperidin-1-yl)ethyl)-[2,3'-bipyridin]-6'-amine |

-continued

| Example No. | Compound Structure | Compound Name |
|---|---|---|
| 220 | 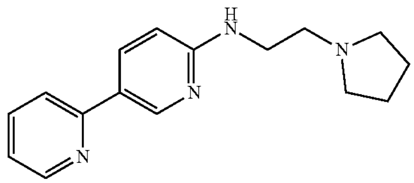 [SMILES: c1ccc(-c2ccc(NCCN3CCCC3)nc2)nc1] | N-(2-(pyrrolidin-1-yl)ethyl)-[2,3'-bipyridin]-6'-amine |
| 221 | 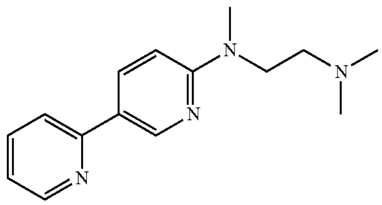 [SMILES: CN(C)CCN(C)c1ccc(-c2ccccn2)cn1] | N1-([2,3'-bipyridin]-6'-yl)-N1,N2,N2-trimethylethane-1,2-diamine |
| 222 | 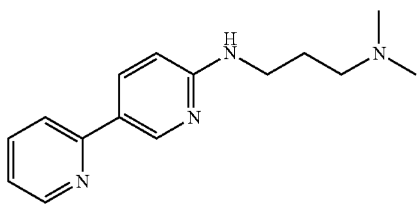 | N1-([2,3'-bipyridin]-6'-yl)-N3,N3-dimethylpropane-1,3-diamine |
| 223 | 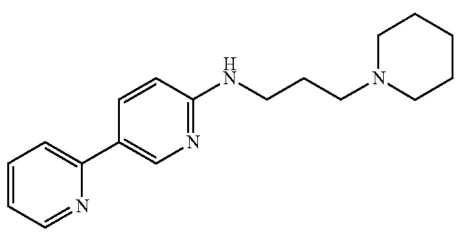 [SMILES: c1ccc(-c2ccc(NCCCN3CCCCC3)nc2)nc1] | N-(3-(piperidin-1-yl)propyl)-[2,3'-bipyridin]-6'-amine |
| 224 | 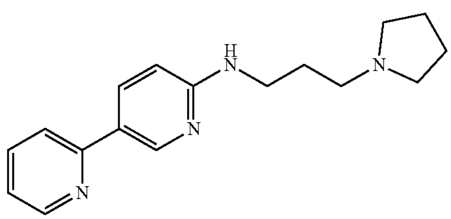 [SMILES: c1ccc(-c2ccc(NCCCN3CCCC3)nc2)nc1] | N-(3-(pyrrolidin-1-yl)propyl)-[2,3'-bipyridin]-6'-amine |
| 225 | 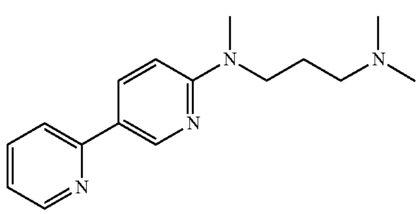 [SMILES: CN(C)CCCN(C)c1ccc(-c2ccccn2)cn1] | N1-([2,3'-bipyridin]-6'-yl)-N1,N3,N3-trimethylpropane-1,3-diamine |
| 226 | 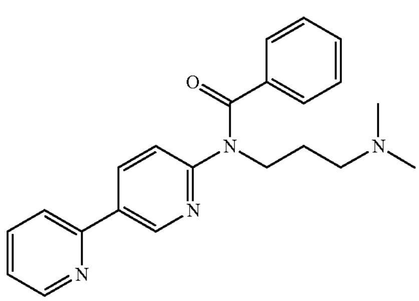 [SMILES: CN(C)CCCN(C(=O)c1ccccc1)c1ccc(-c2ccccn2)cn1] | N-([2,3'-bipyridin]-6'-yl)-N-(3-(dimethylamino)propyl)benzamide |

-continued
| Example No. | Compound Structure | Compound Name |
|---|---|---|
| 227 | 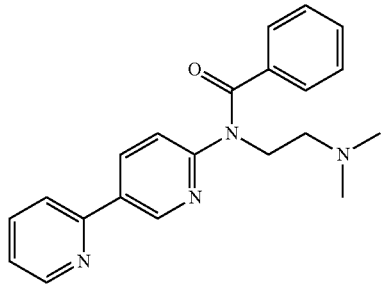 [SMILES: CN(C)CCN(C(=O)c1ccccc1)c1ccc(-c2ccccn2)cn1] | N-([2,3'-bipyridin]-6'-yl)-N-(2-(dimethylamino)ethyl)benzamide |
| 228 | 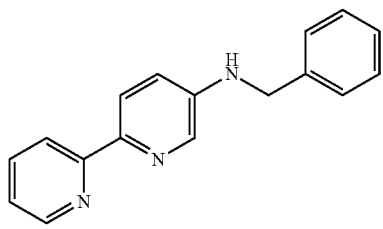 [SMILES: c1ccc(CNc2ccc(-c3ccccn3)nc2)cc1] | N-benzyl-[2,2'-bipyridin]-5-amine |
| 229 | 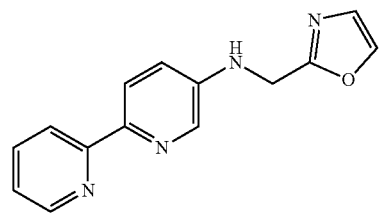 [SMILES: c1ccc(-c2ccc(NCc3ncco3)cn2)nc1] | N-(oxazol-2-ylmethyl)-[2,2'-bipyridin]-5-amine |
| 230 | 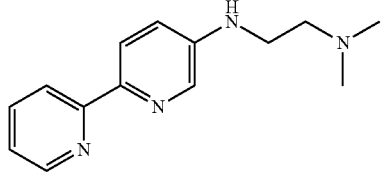 [SMILES: CN(C)CCNc1ccc(-c2ccccn2)nc1] | N1-([2,2'-bipyridin]-5-yl)-N2,N2-dimethylethane-1,2-diamine |
| 231 | 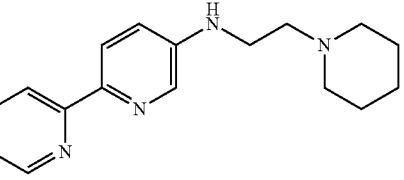 | N-(2-(piperidin-1-yl)ethyl)-[2,2'-bipyridin]-5-amine |
| 232 | 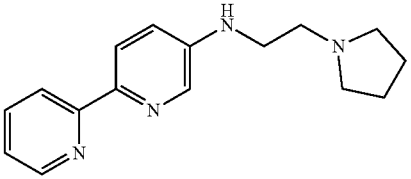 [SMILES: c1ccc(-c2ccc(NCCN3CCCC3)cn2)nc1] | N-(2-(pyrrolidin-1-yl)ethyl)-[2,2'-bipyridin]-5-amine |
| 233 | 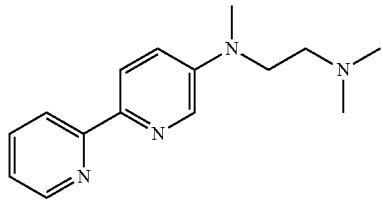 [SMILES: CN(C)CCN(C)c1ccc(-c2ccccn2)nc1] | N1-([2,2'-bipyridin]-5-yl)-N1,N2,N2-trimethylethane-1,2-diamine |

-continued

| Example No. | Compound Structure | Compound Name |
|---|---|---|
| 234 | 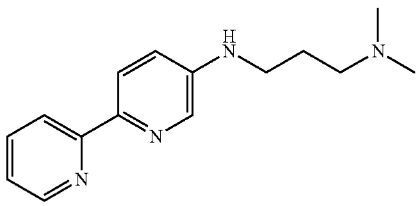 [SMILES: CN(C)CCCNc1ccc(-c2ccccn2)nc1] | N1-([2,2'-bipyridin]-5-yl)-N3,N3-dimethylpropane-1,3-diamine |
| 235 | 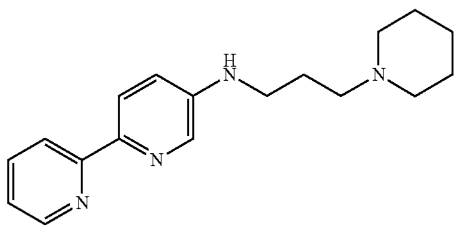 [SMILES: c1ccc(-c2ccc(NCCCN3CCCCC3)cn2)nc1] | N-(3-(piperidin-1-yl)propyl)-[2,2'-bipyridin]-5-amine |
| 236 | 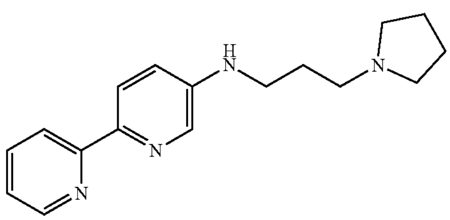 [SMILES: c1ccc(-c2ccc(NCCCN3CCCC3)cn2)nc1] | N-(3-(pyrrolidin-1-yl)propyl)-[2,2'-bipyridin]-5-amine |
| 237 | 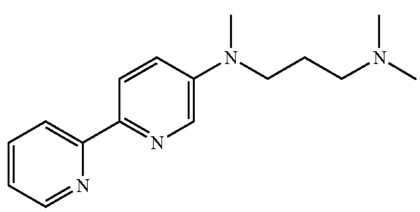 [SMILES: CN(C)CCCN(C)c1ccc(-c2ccccn2)nc1] | N1-([2,2'-bipyridin]-5-yl)-N1,N3,N3-trimethylpropane-1,3-diamine |
| 238 | 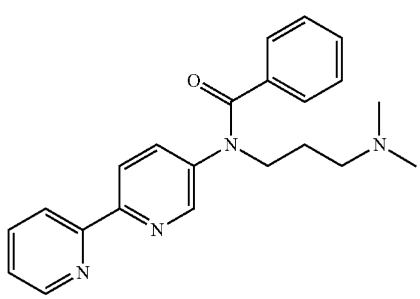 [SMILES: CN(C)CCCN(C(=O)c1ccccc1)c1ccc(-c2ccccn2)nc1] | N-([2,2'-bipyridin]-5-yl)-N-(3-(dimethylamino)propyl)benzamide |
| 239 | 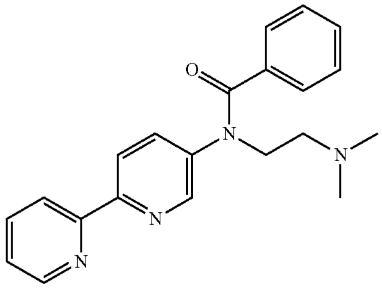 [SMILES: CN(C)CCN(C(=O)c1ccccc1)c1ccc(-c2ccccn2)nc1] | N-([2,2'-bipyridin]-5-yl)-N-(2-(dimethylamino)ethyl)benzamide |

| Example No. | Compound Structure | Compound Name |
|---|---|---|
| 240 | 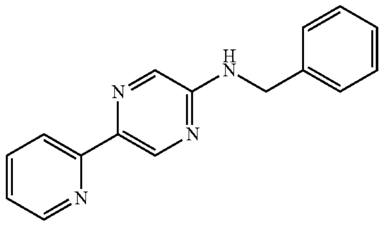 | N-benzyl-5-(pyridin-2-yl)pyrazin-2-amine |
| 241 | 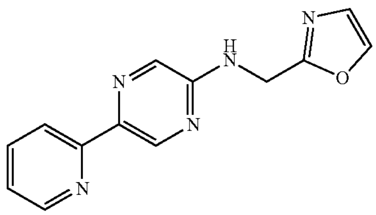 [SMILES: c1ccc(-c2cnc(NCc3ncco3)cn2)nc1] | N-(oxazol-2-ylmethyl)-5-(pyridin-2-yl)pyrazin-2-amine |
| 242 | 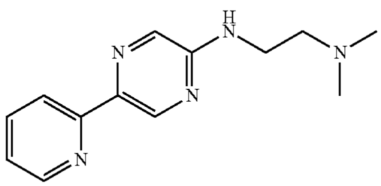 [SMILES: CN(C)CCNc1cnc(-c2ccccn2)cn1] | N1,N1-dimethyl-N2-(5-(pyridin-2-yl)pyrazin-2-yl)ethane-1,2-diamine |
| 243 | 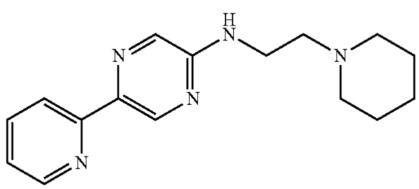 [SMILES: c1ccc(-c2cnc(NCCN3CCCCC3)cn2)nc1] | N-(2-(piperidin-1-yl)ethyl)-5-(pyridin-2-yl)pyrazin-2-amine |
| 244 | 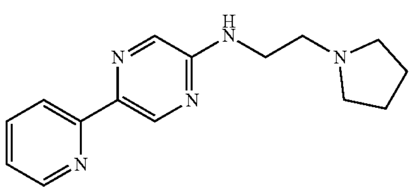 [SMILES: c1ccc(-c2cnc(NCCN3CCCC3)cn2)nc1] | 5-(pyridin-2-yl)-N-(2-(pyrrolidin-1-yl)ethyl)pyrazin-2-amine |
| 245 | 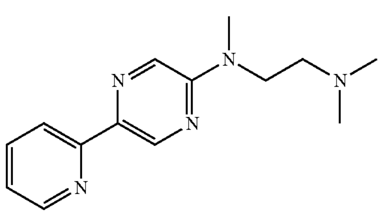 [SMILES: CN(C)CCN(C)c1cnc(-c2ccccn2)cn1] | N1,N1,N2-trimethyl-N2-(5-(pyridin-2-yl)pyrazin-2-yl)ethane-1,2-diamine |
| 246 | 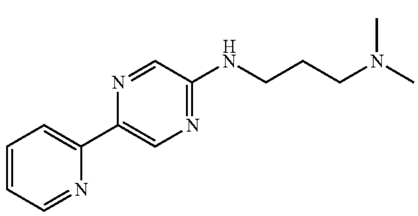 [SMILES: CN(C)CCCNc1cnc(-c2ccccn2)cn1] | N1,N1-dimethyl-N3-(5-(pyridin-2-yl)pyrazin-2-yl)propane-1,3-diamine |

-continued

| Example No. | Compound Structure | Compound Name |
|---|---|---|
| 247 | 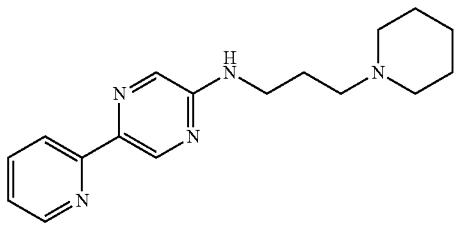 [SMILES: c1ccc(-c2cnc(NCCCN3CCCCC3)cn2)nc1] | N-(3-(piperidin-1-yl)propyl)-5-(pyridin-2-yl)pyrazin-2-amine |
| 248 | 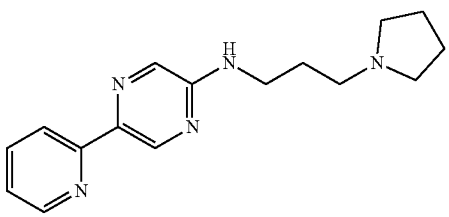 [SMILES: c1ccc(-c2cnc(NCCCN3CCCC3)cn2)nc1] | 5-(pyridin-2-yl)-N-(3-(pyrrolidin-1-yl)propyl)pyrazin-2-amine |
| 249 | 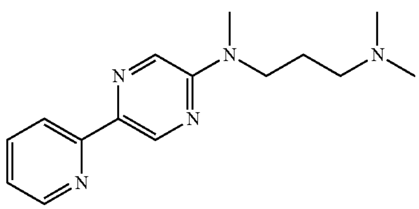 [SMILES: CN(C)CCCN(C)c1cnc(-c2ccccn2)cn1] | N1,N1,N3-trimethyl-N3-(5-(pyridin-2-yl)pyrazin-2-yl)propane-1,3-diamine |
| 250 | 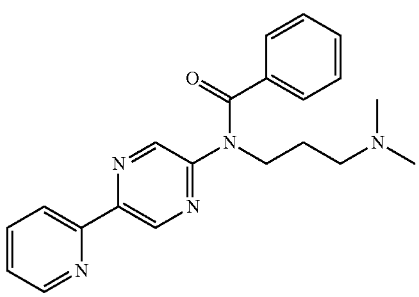 [SMILES: CN(C)CCCN(C(=O)c1ccccc1)c1cnc(-c2ccccn2)cn1] | N-(3-(dimethylamino)propyl)-N-(5-(pyridin-2-yl)pyrazin-2-yl)benzamide |
| 251 | 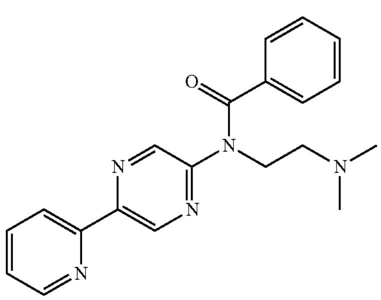 [SMILES: CN(C)CCN(C(=O)c1ccccc1)c1cnc(-c2ccccn2)cn1] | N-(2-(dimethylamino)ethyl)-N-(5-(pyridin-2-yl)pyrazin-2-yl)benzamide |
| 252 | 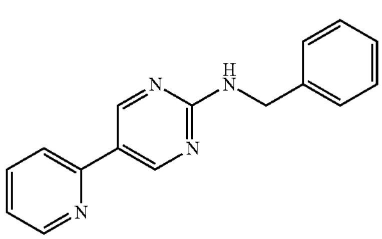 [SMILES: c1ccc(CNc2ncc(-c3ccccn3)cn2)cc1] | N-benzyl-5-(pyridin-2-yl)pyrimidin-2-amine |

| Example No. | Compound Structure | Compound Name |
|---|---|---|
| 253 | 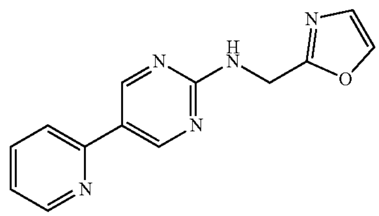 [SMILES: c1ccc(-c2cnc(NCc3ncco3)nc2)nc1] | N-(oxazol-2-ylmethyl)-5-(pyridin-2-yl)pyrimidin-2-amine |
| 254 | 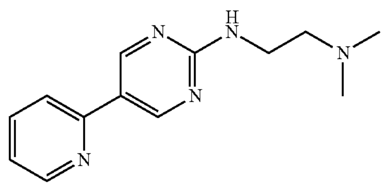 [SMILES: CN(C)CCNc1ncc(-c2ccccn2)cn1] | N1,N1-dimethyl-N2-(5-(pyridin-2-yl)pyrimidin-2-yl)ethane-1,2-diamine |
| 255 | 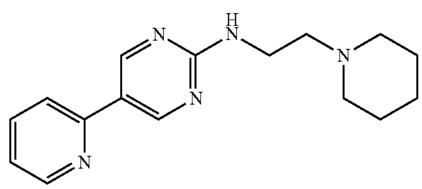 [SMILES: c1ccc(-c2cnc(NCCN3CCCCC3)nc2)nc1] | N-(2-(piperidin-1-yl)ethyl)-5-(pyridin-2-yl)pyrimidin-2-amine |
| 256 | 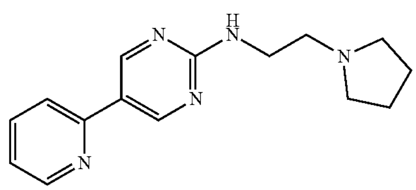 [SMILES: c1ccc(-c2cnc(NCCN3CCCC3)nc2)nc1] | 5-(pyridin-2-yl)-N-(2-(pyrrolidin-1-yl)ethyl)pyrimidin-2-amine |
| 257 | 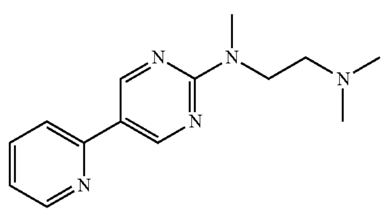 [SMILES: CN(C)CCN(C)c1ncc(-c2ccccn2)cn1] | N1,N1,N2-trimethyl-N2-(5-(pyridin-2-yl)pyrimidin-2-yl)ethane-1,2-diamine |
| 258 | 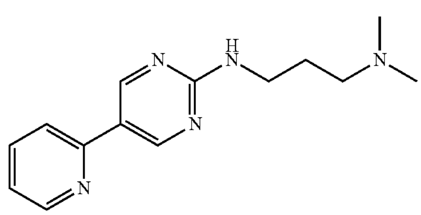 [SMILES: CN(C)CCCNc1ncc(-c2ccccn2)cn1] | N1,N1-dimethyl-N3-(5-(pyridin-2-yl)pyrimidin-2-yl)propane-1,3-diamine |
| 259 | 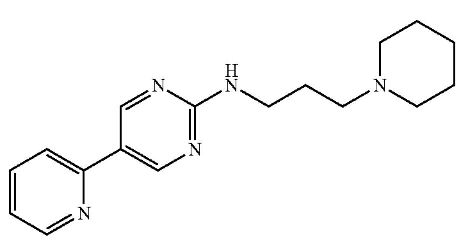 [SMILES: c1ccc(-c2cnc(NCCCN3CCCCC3)nc2)nc1] | N-(3-(piperidin-1-yl)propyl)-5-(pyridin-2-yl)pyrimidin-2-amine |

| Example No. | Compound Structure | Compound Name |
|---|---|---|
| 260 | 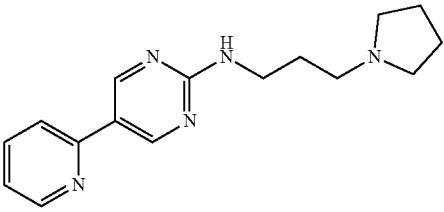 [SMILES: c1ccc(-c2cnc(NCCCN3CCCC3)nc2)nc1] | 5-(pyridin-2-yl)-N-(3-(pyrrolidin-1-yl)propyl)pyrimidin-2-amine |
| 261 | 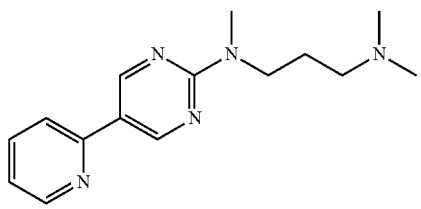 [SMILES: CN(C)CCCN(C)c1ncc(-c2ccccn2)cn1] | N1,N1,N3-trimethyl-N3-(5-(pyridin-2-yl)pyrimidin-2-yl)propane-1,3-diamine |
| 262 | 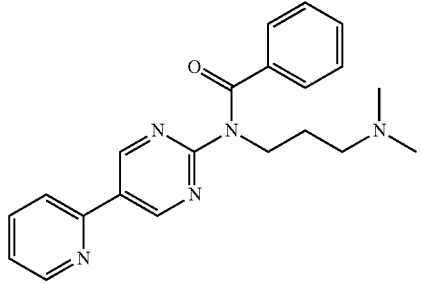 [SMILES: CN(C)CCCN(C(=O)c1ccccc1)c1ncc(-c2ccccn2)cn1] | N-(3-(dimethylamino)propyl)-N-(5-(pyridin-2-yl)pyrimidin-2-yl)benzamide |
| 263 | 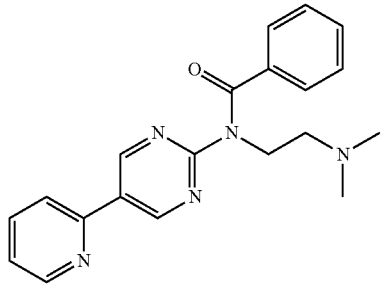 [SMILES: CN(C)CCN(C(=O)c1ccccc1)c1ncc(-c2ccccn2)cn1] | N-(2-(dimethylamino)ethyl)-N-(5-(pyridin-2-yl)pyrimidin-2-yl)benzamide |
| 264 | 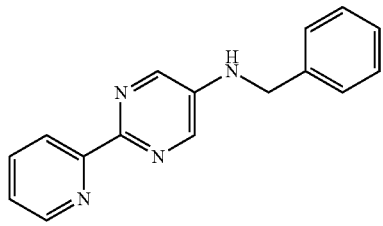 [SMILES: c1ccc(CNc2cnc(-c3ccccn3)nc2)cc1] | N-benzyl-2-(pyridin-2-yl)pyrimidin-5-amine |
| 265 | 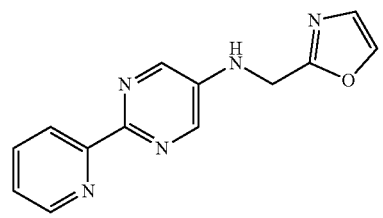 [SMILES: c1ccc(-c2ncc(NCc3ncco3)cn2)nc1] | N-(oxazol-2-ylmethyl)-2-(pyridin-2-yl)pyrimidin-5-amine |

| Example No. | Compound Structure | Compound Name |
|---|---|---|
| 266 | 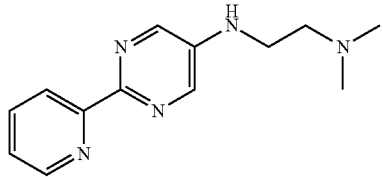 [SMILES: CN(C)CCNc1cnc(-c2ccccn2)nc1] | N1,N1-dimethyl-N2-(2-(pyridin-2-yl)pyrimidin-5-yl)ethane-1,2-diamine |
| 267 | 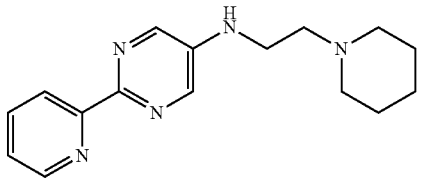 [SMILES: c1ccc(-c2ncc(NCCN3CCCCC3)cn2)nc1] | N-(2-(piperidin-1-yl)ethyl)-2-(pyridin-2-yl)pyrimidin-5-amine |
| 268 | 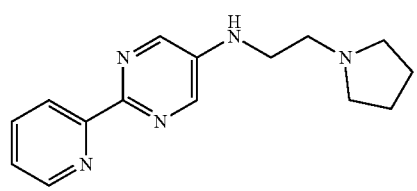 [SMILES: c1ccc(-c2ncc(NCCN3CCCC3)cn2)nc1] | 2-(pyridin-2-yl)-N-(2-(pyrrolidin-1-yl)ethyl)pyrimidin-5-amine |
| 269 | 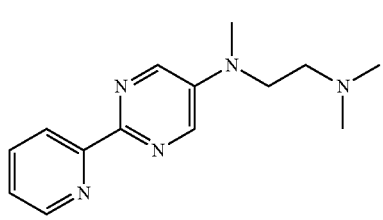 [SMILES: CN(C)CCN(C)c1cnc(-c2ccccn2)nc1] | N1,N1,N2-trimethyl-N2-(2-(pyridin-2-yl)pyrimidin-5-yl)ethane-1,2-diamine |
| 270 | 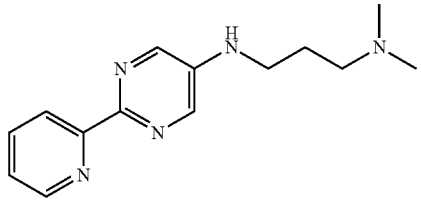 [SMILES: CN(C)CCCNc1cnc(-c2ccccn2)nc1] | N1,N1-dimethyl-N3-(2-(pyridin-2-yl)pyrimidin-5-yl)propane-1,3-diamine |
| 271 | 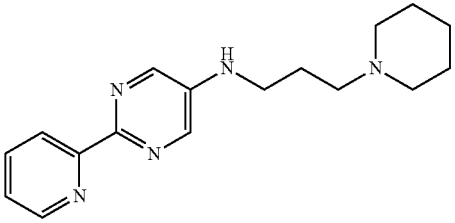 [SMILES: c1ccc(-c2ncc(NCCCN3CCCCC3)cn2)nc1] | N-(3-(piperidin-1-yl)propyl)-2-(pyridin-2-yl)pyrimidin-5-amine |

| Example No. | Compound Structure | Compound Name |
|---|---|---|
| 272 | 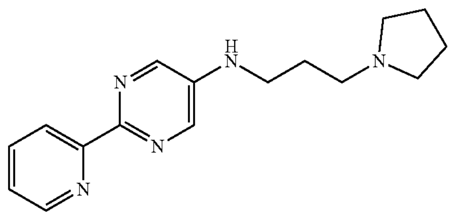 [SMILES: c1ccc(-c2ncc(NCCCN3CCCC3)cn2)nc1] | 2-(pyridin-2-yl)-N-(3-(pyrrolidin-1-yl)propyl)pyrimidin-5-amine |
| 273 | 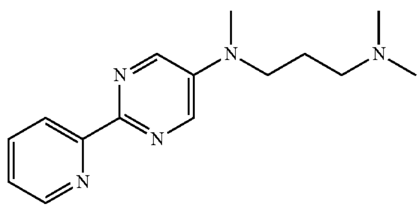 [SMILES: CN(C)CCCN(C)c1cnc(-c2ccccn2)nc1] | N1,N1,N3-trimethyl-N3-(2-(pyridin-2-yl)pyrimidin-5-yl)propane-1,3-diamine |
| 274 | 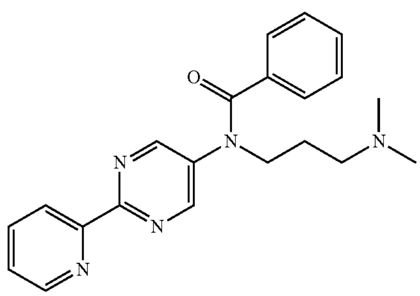 [SMILES: CN(C)CCCN(C(=O)c1ccccc1)c1cnc(-c2ccccn2)nc1] | N-(3-(dimethylamino)propyl)-N-(2-(pyridin-2-yl)pyrimidin-5-yl)benzamide |
| 275 | 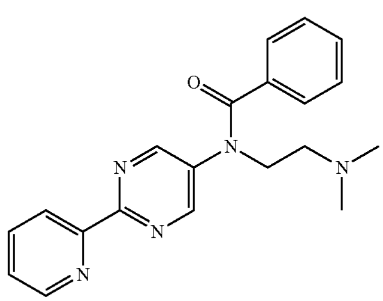 [SMILES: CN(C)CCN(C(=O)c1ccccc1)c1cnc(-c2ccccn2)nc1] | N-(2-(dimethylamino)ethyl)-N-(2-(pyridin-2-yl)pyrimidin-5-yl)benzamide |

Example 276. Evaluation of the Biological Activity of Example Compounds

In vitro assay in primary astrocyte cultures. Example compounds were initially evaluated in PA-EAAT2 cells, a primary astrocyte stably expressing human EAAT2 mRNAs (Kong et al., *J Clin Invest.* 124:1255-67). Cells were treated with the example compounds at 0.25 µM, 0.5 µM, 1 µM, 2.5 µM, 5 µM, 10 µM, and 25 µM for 24 hr and then harvested for measuring EAAT2 protein levels by Western blot analysis. Table 1 shows the fold increases in EAAT2 protein levels relative to DMSO controls at indicated concentration that reaches maximum activity.

In vivo assay in wild-type mice. Example compounds that were capable of increasing EAAT2 protein expression in cultured astrocytes were further evaluated in C57BL/6J mice. Mice were treated by oral gavage with the compound at 40 mg/kg. At 24 hr post-treatment, mice were euthanized and forebrains were harvested for the gliosome preparation (Dunkley et al., *Nat Protoc* 3, 1718-1728). Gliosomes are enriched with astrocytic processes, and majority of EAAT2 is localized in astrocytic processes (gliosomes). EAAT2 protein levels in gliosomes were determined by Western blot analysis. Table 1 shows the fold increases in EAAT2 protein levels relative to vehicle controls.

TABLE 1

| | | Biological Activity of Example Compounds | |
|---|---|---|---|
| Example | Compound Structure | In vitro - fold increase for EAAT2 in cultured astrocytes at indicated concentration (maximum activity) | In vivo - fold increase for EAAT2 in mouse forebrain at 24 hr post treatment (40 mg/kg by PO) |
| 3 | (structure) | 1.68 (5 μM) | 1.42 |
| 48 | (structure) | 1.58 (2.5 μM) | 1.45 |
| 63 | (structure) | 1.32 (5 μM) | no increase |
| 18 | (structure) | 2.45 (1 μM) | 1.56 |
| 33 | (structure) | no increase | no increase |
| 19 | (structure) | 1.97 (1 μM) | 1.41 |

TABLE 1-continued

Biological Activity of Example Compounds

| Example | Compound Structure | In vitro - fold increase for EAAT2 in cultured astrocytes at indicated concentration (maximum activity) | In vivo - fold increase for EAAT2 in mouse forebrain at 24 hr post treatment (40 mg/kg by PO) |
|---|---|---|---|
| 22 | *4-Cl-benzamide of 6-(pyridin-2-yl)pyridin-3-amine* | 1.64 (0.5 μM) | 1.20 |
| 21 | *4-OMe-benzamide of 6-(pyridin-2-yl)pyridin-3-amine* | 1.73 (0.5 μM) | 1.34 |
| 20 | *4-F-3-Cl-benzamide of 6-(pyridin-2-yl)pyridin-3-amine* | no increase | no increase |
| 23 | *3-Cl-benzamide of 6-(pyridin-2-yl)pyridin-3-amine* | 1.84 (2.5 μM) | 1.45 |
| 94 | *2-(dimethylamino)ethoxy derivative of 2,2'-bipyridine* | 1.51 (5 μM) | 1.49 |
| 157 | *2-(dimethylamino)ethoxy pyrimidine-pyridine derivative* | 1.54 (1 μM) | 1.37 |

TABLE 1-continued

Biological Activity of Example Compounds

| Example | Compound Structure | In vitro - fold increase for EAAT2 in cultured astrocytes at indicated concentration (maximum activity) | In vivo - fold increase for EAAT2 in mouse forebrain at 24 hr post treatment (40 mg/kg by PO) |
|---|---|---|---|
| 136 | 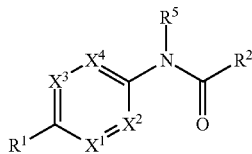 | no increase | no increase |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

What is claimed is:

1. A compound of Formula I:

I or a pharmaceutically acceptable salt thereof, wherein:
$X^1$ is CH or N;
$X^2$ is CH or N;
$X^3$ is $CR^3$ or N;
$X^4$ is $CR^4$ or N;
wherein the ring comprising $X^1$, $X^2$, $X^3$, and $X^4$ forms a pyridine ring, a pyrazine ring, or a pyrimidine ring;
$R^1$ is unsubstituted pyridyl;
$R^2$ is selected from the group consisting of phenyl, imidazolyl, thiazolyl, oxazolyl, pyrrolidinyl, and piperidinyl, each of which is optionally substituted by 1, 2, 3, or 4 independently selected $R^B$ groups;
$R^3$, $R^4$, and $R^5$ are each independently selected from H and $C_{1-6}$ alkyl;
each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;
each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;
each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and
each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

2. The compound of claim 1, or a pharmaceutically acceptable salt thereof, wherein each $R^B$ is independently selected from the group consisting of halo, $C_{1-6}$ alkyl, and $OR^a$.

3. The compound of claim 2, or a pharmaceutically acceptable salt thereof, wherein each $R^B$ is independently selected from the group consisting of F, Cl, $C_{1-3}$ alkyl, and $C_{1-3}$ alkoxy.

4. The compound of claim 1, or a pharmaceutically acceptable salt thereof, wherein $R^3$ is H.

5. The compound of claim 1, or a pharmaceutically acceptable salt thereof, wherein $R^4$ is H.

6. The compound of claim 1, or a pharmaceutically acceptable salt thereof, wherein $R^5$ is H.

7. The compound of claim 1, or a pharmaceutically acceptable salt thereof, wherein the ring comprising $X^1$, $X^2$, $X^3$, and $X^4$ forms a pyridine ring.

8. The compound of claim 1, or a pharmaceutically acceptable salt thereof, wherein the ring comprising $X^1$, $X^2$, $X^3$, and $X^4$ forms a pyrazine ring.

9. The compound of claim 1, or a pharmaceutically acceptable salt thereof, wherein the ring comprising $X^1$, $X^2$, $X^3$, and $X^4$ forms a pyrimidine ring.

10. The compound of claim 1, or a pharmaceutically acceptable salt thereof, wherein:
    the ring comprising $X^1$, $X^2$, $X^3$, and $X^4$ forms a pyridine ring, a pyrazine ring, or a pyrimidine ring;
    $R^1$ is unsubstituted pyridyl;
    $R^2$ is selected from the group consisting of phenyl, imidazolyl, thiazolyl, oxazolyl, pyrrolidinyl, and piperidinyl, each of which is optionally substituted by 1, 2, 3, or 4 independently selected $R^B$ groups;
    each $R^B$ is independently selected from the group consisting of halo, $C_{1-6}$ alkyl, and $OR^a$;
    $R^3$ is H;
    $R^4$ is H; and
    $R^5$ is H.

11. The compound of claim 1, or a pharmaceutically acceptable salt thereof, wherein:
    the ring comprising $X^1$, $X^2$, $X^3$, and $X^4$ forms a pyridine ring, a pyrazine ring, or a pyrimidine ring;
    $R^1$ is an unsubstituted 5-6 membered heteroaryl;
    $R^2$ is selected from the group consisting of phenyl, 5-6 membered heteroaryl, and 4-6 membered heterocycloalkyl, each of which is optionally substituted by 1 or 2 independently selected $R^B$ groups;
    each $R^B$ is independently selected from the group consisting of halo, $C_{1-6}$ alkyl, and $OCH_3$;
    $R^3$ is H;
    $R^4$ is H; and
    $R^5$ is H.

12. The compound of claim 1, or a pharmaceutically acceptable salt thereof, wherein the compound of Formula I is selected from the group consisting of:

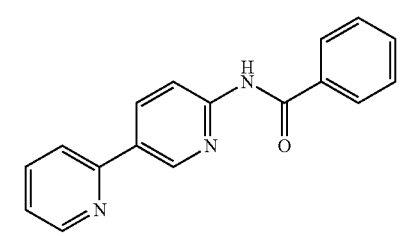 [SMILES: O=C(Nc1ccc(-c2ccccn2)cn1)c1ccccc1]

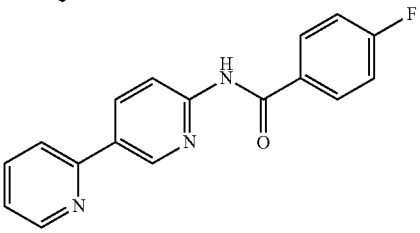

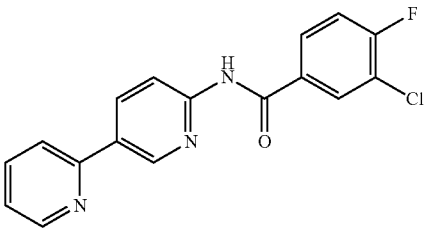

-continued

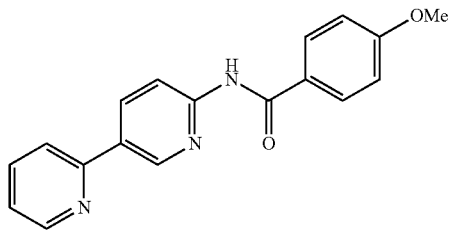

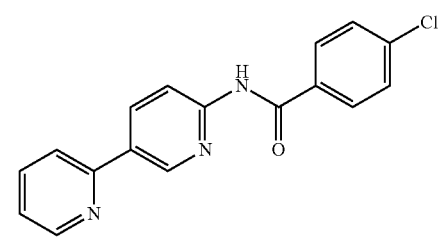

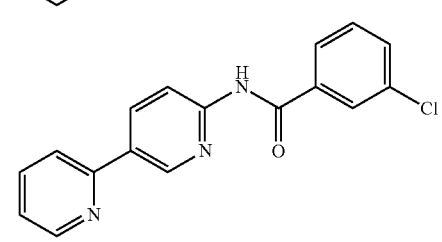

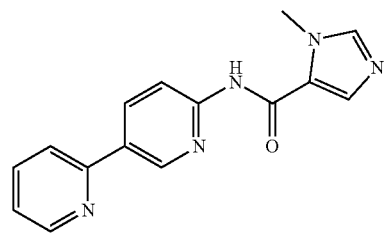

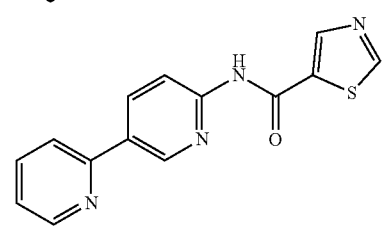

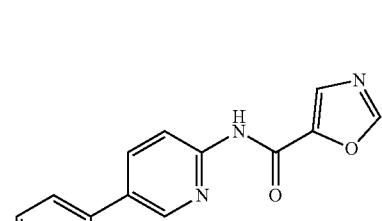

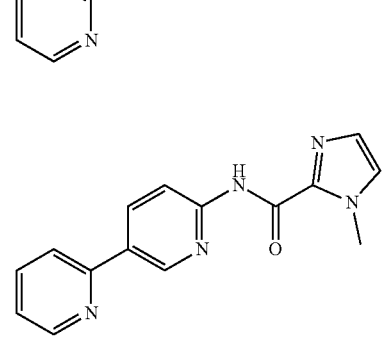

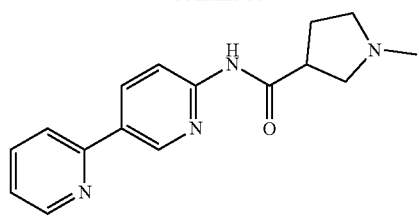
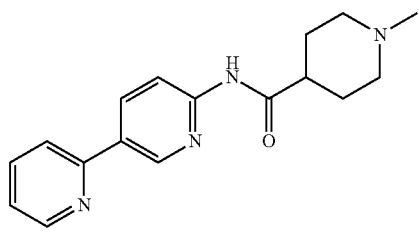
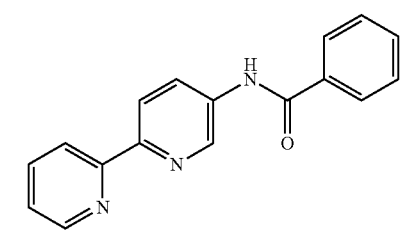
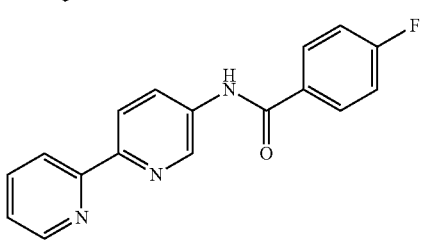
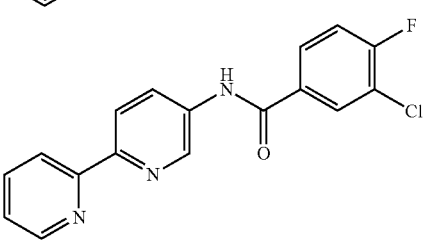
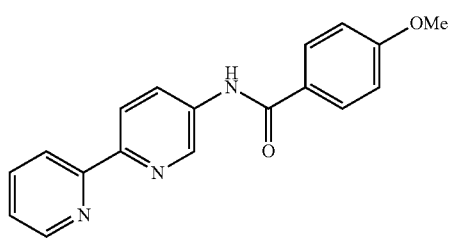
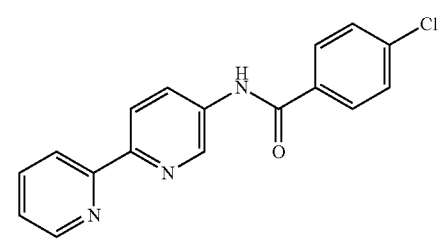
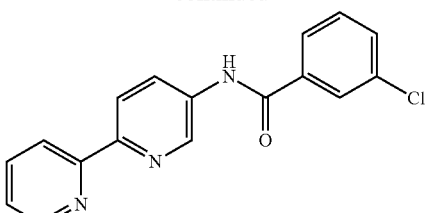
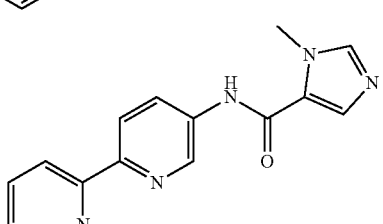
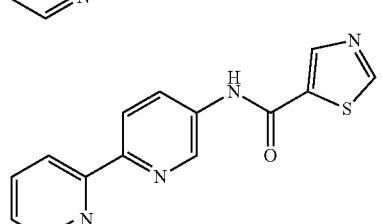
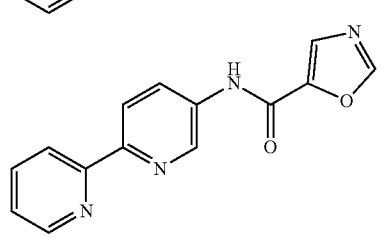
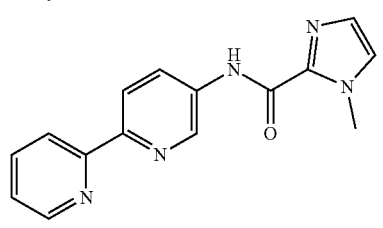
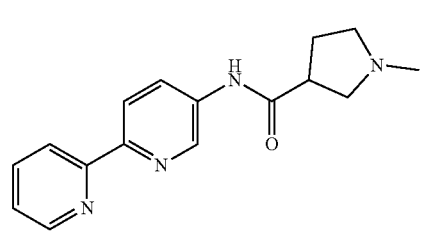
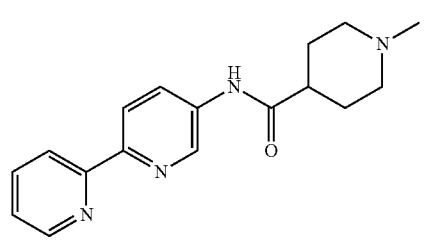

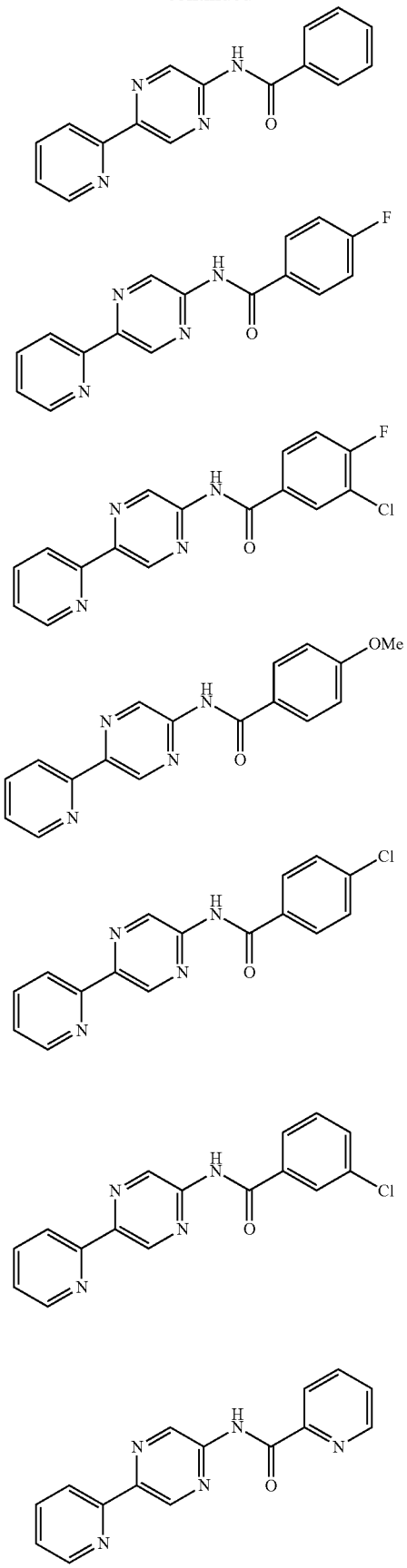
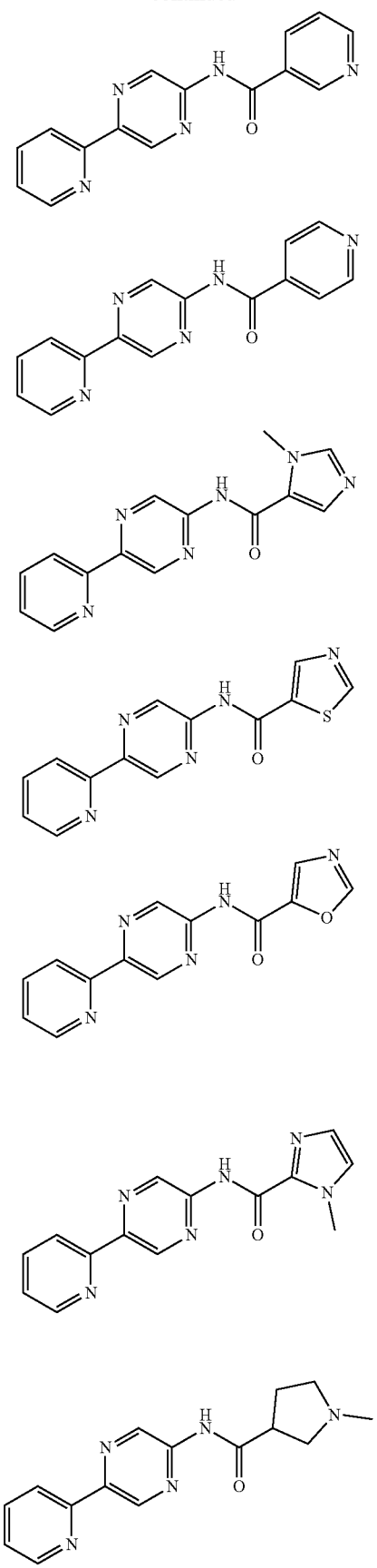

-continued
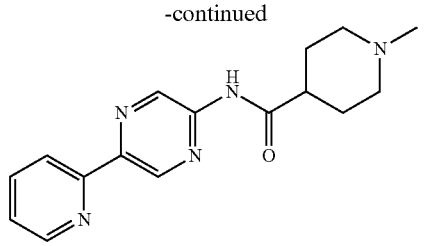
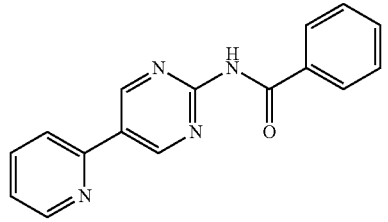 [SMILES: O=C(Nc1ncc(-c2ccccn2)cn1)c1ccccc1]
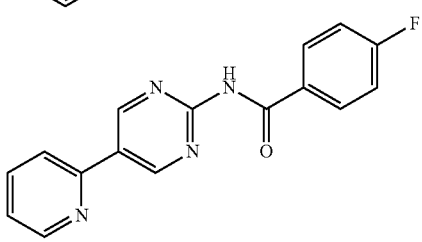
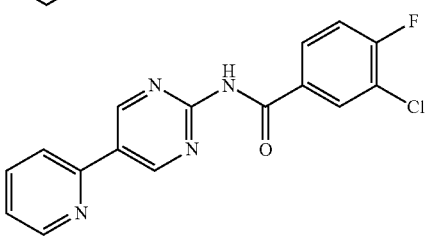
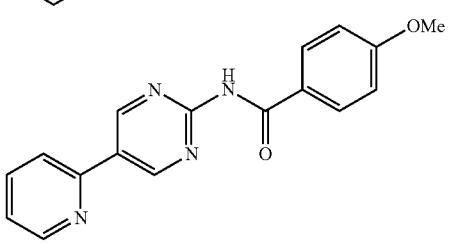
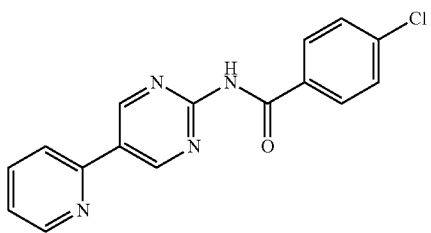
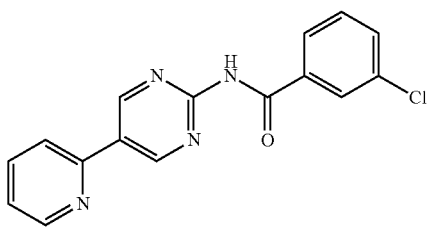
-continued
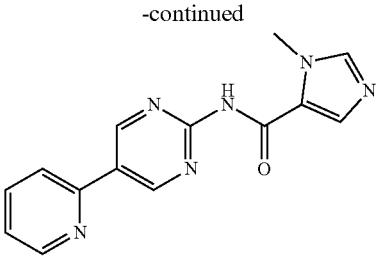
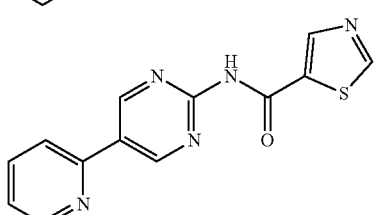
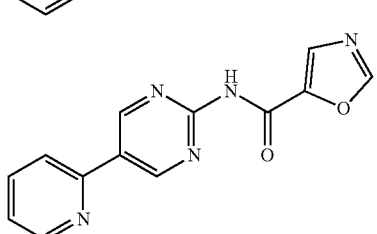
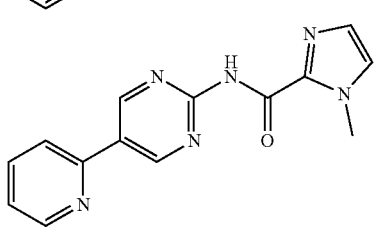
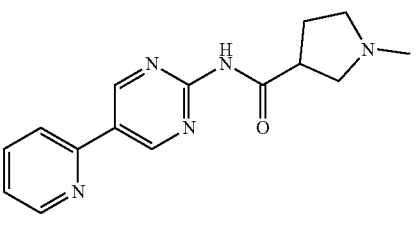
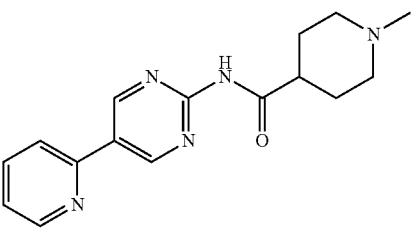
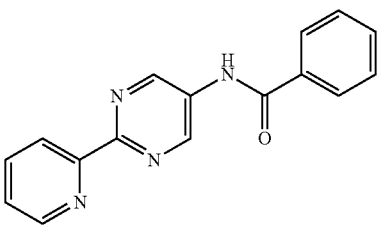 [SMILES: O=C(Nc1cnc(-c2ccccn2)nc1)c1ccccc1]

-continued
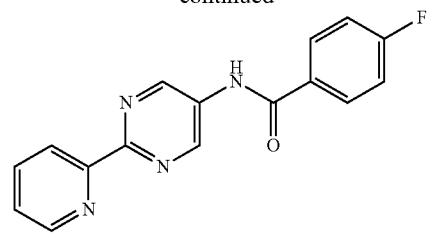
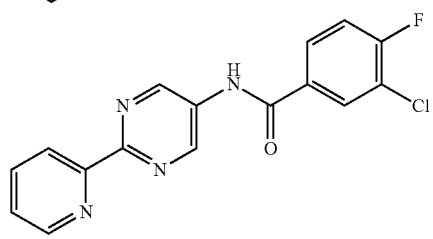
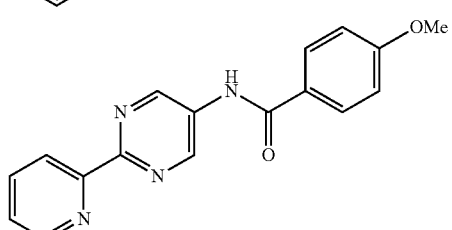
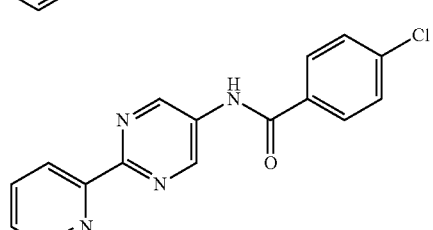
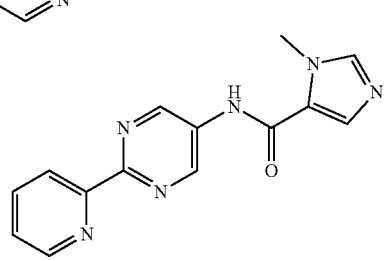
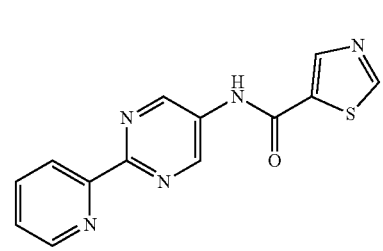
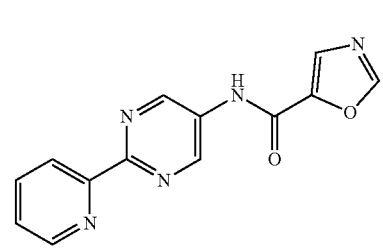
-continued
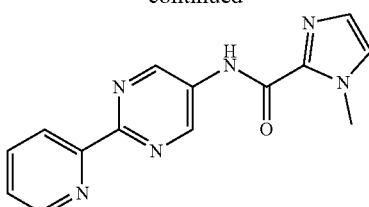
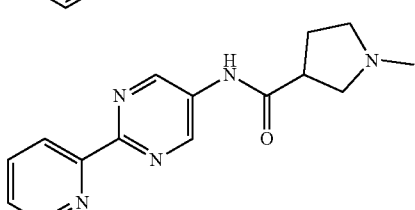
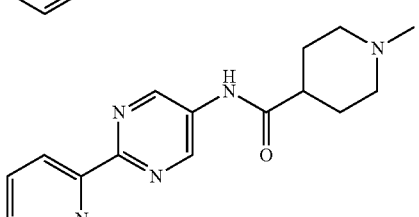
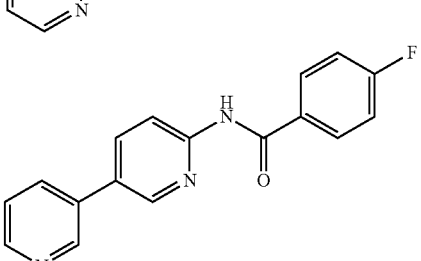
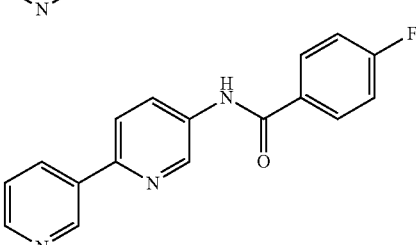
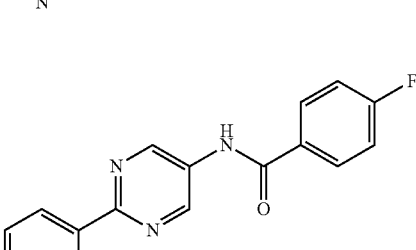
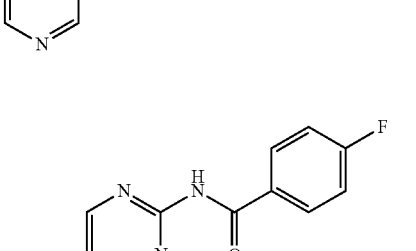
and

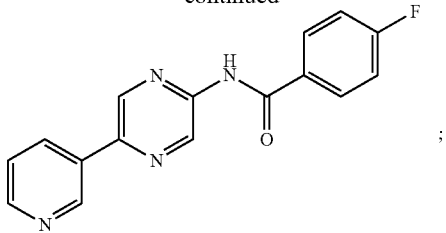

or a pharmaceutically acceptable salt thereof.

13. A compound of Formula II:

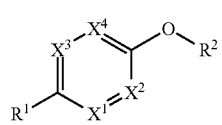

or a pharmaceutically acceptable salt thereof, wherein:
$X^1$ is CH or N;
$X^2$ is CH or N;
$X^3$ is $CR^3$ or N;
$X^4$ is $CR^4$ or N;
wherein the ring comprising $X^1$, $X^2$, $X^3$, and $X^4$ forms a pyridine ring, a pyrazine ring, or a pyrimidine ring;
$R^1$ is unsubstituted pyridyl;
$R^2$ is —$(CHR^E)_nR^5$;
$R^5$ is selected from the group consisting of $OR^C$, $NR^CR^D$, $C(O)NR^CR^D$, $C(O)OR^C$, $C_{3-10}$ cycloalkyl 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;
$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;
$R^3$ and $R^4$ are independently selected from H and $C_{1-6}$ alkyl;
each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;
$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heterocycloalkyl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or
alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;
each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;
each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;
each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and
n is 0, 1, 2, 3, 4, or 5.

14. A compound of Formula III:

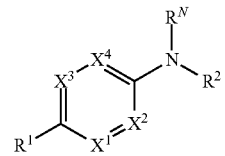

or a pharmaceutically acceptable salt thereof, wherein:
$X^1$ is CH or N;
$X^2$ is CH or N;
$X^3$ is $CR^3$ or N;
$X^4$ is $CR^4$ or N;
wherein the ring comprising $X^1$, $X^2$, $X^3$, and $X^4$ forms a pyridine ring, a pyrazine ring, or a pyrimidine ring;
$R^N$ is selected from the group consisting of H, $C_{1-6}$ alkyl, and $C(O)R^{N1}$;
$R^{N1}$ is a $C_{6-10}$ aryl which is optionally substituted by 1, 2, 3, or 4 independently selected halo groups;
$R^1$ is unsubstituted pyridyl;
$R^2$ is —$(CHR^E)_nR^5$;
$R^5$ is selected from the group consisting of $NR^CR^D$, $C(O)NR^CR^D$, $C(O)OR^C$, $C_{3-10}$ cycloalkyl, $C_{6-10}$ aryl, and 5-10 membered heteroaryl, wherein the $C_{3-10}$ cycloalkyl, $C_{6-10}$ aryl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl) amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

15. A pharmaceutical composition comprising a compound of claim 1, or a pharmaceutically acceptable salt thereof, and a pharmaceutically acceptable excipient.

16. The compound of claim 13, or a pharmaceutically acceptable salt thereof, wherein the compound of Formula I is selected from the group consisting of:

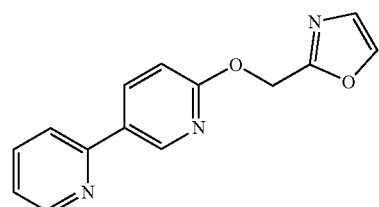

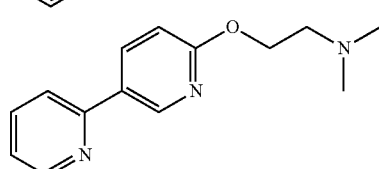

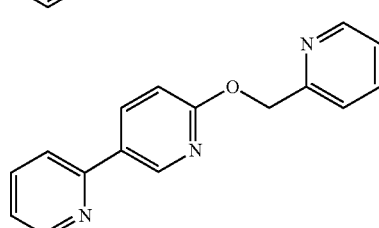

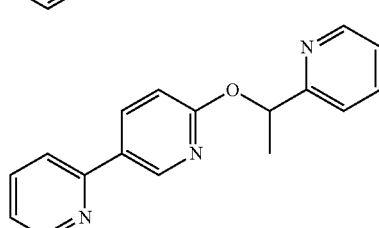

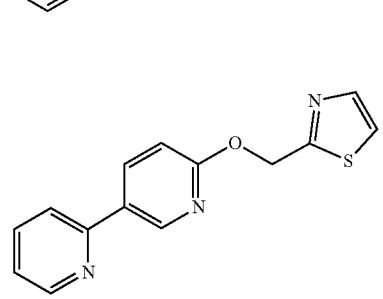

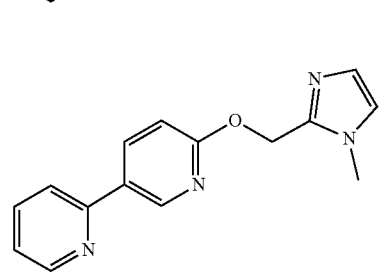

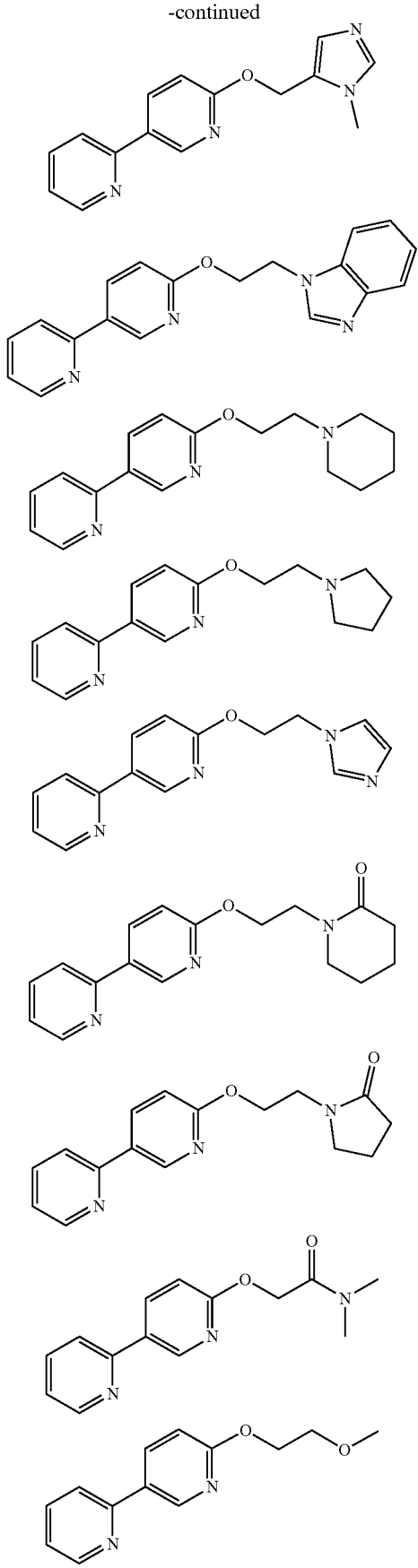
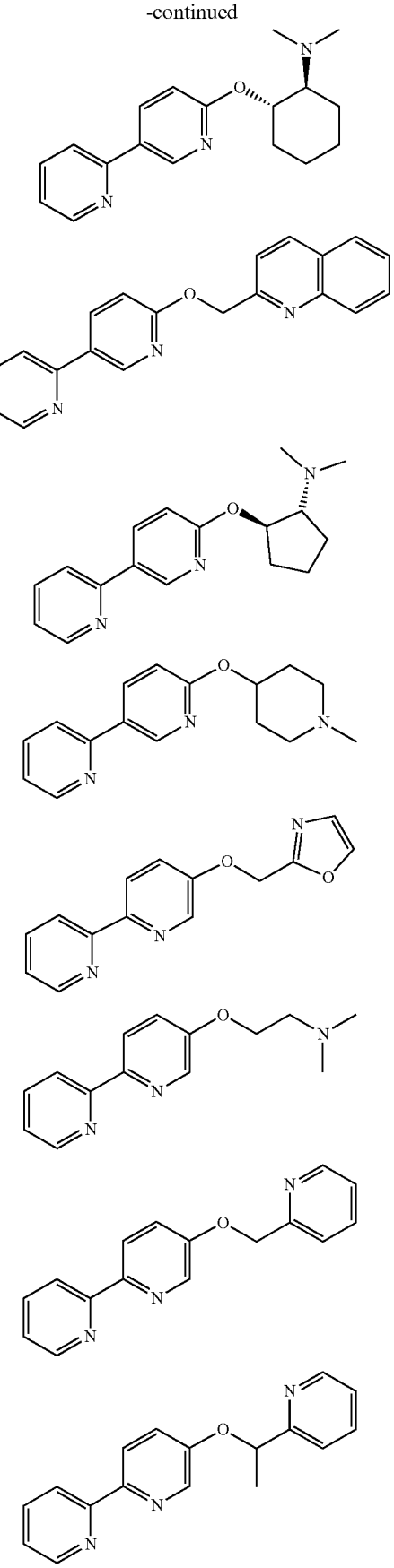

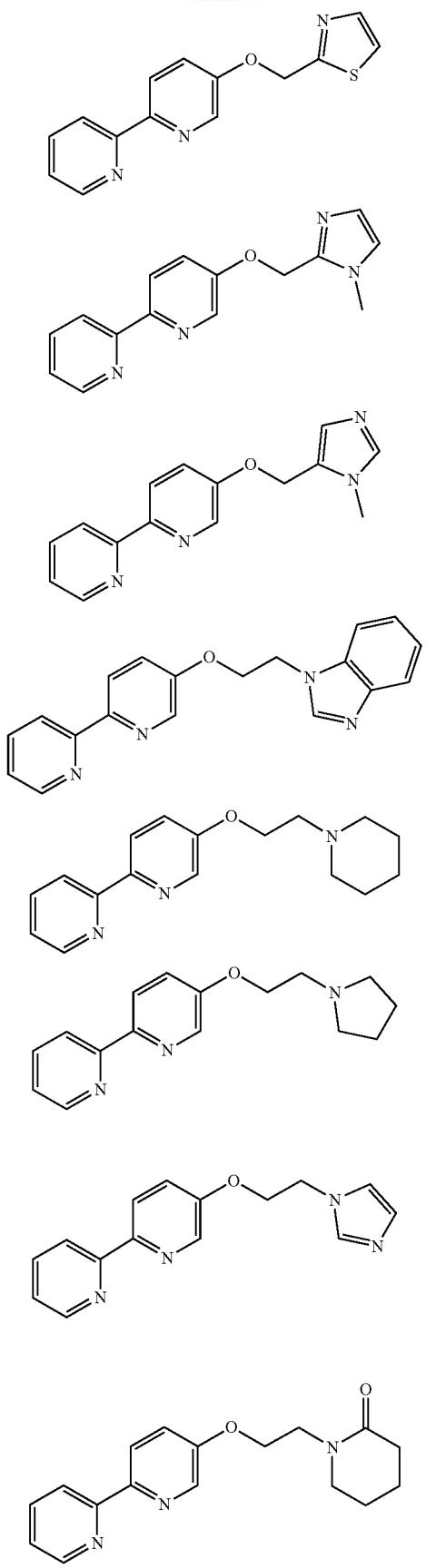
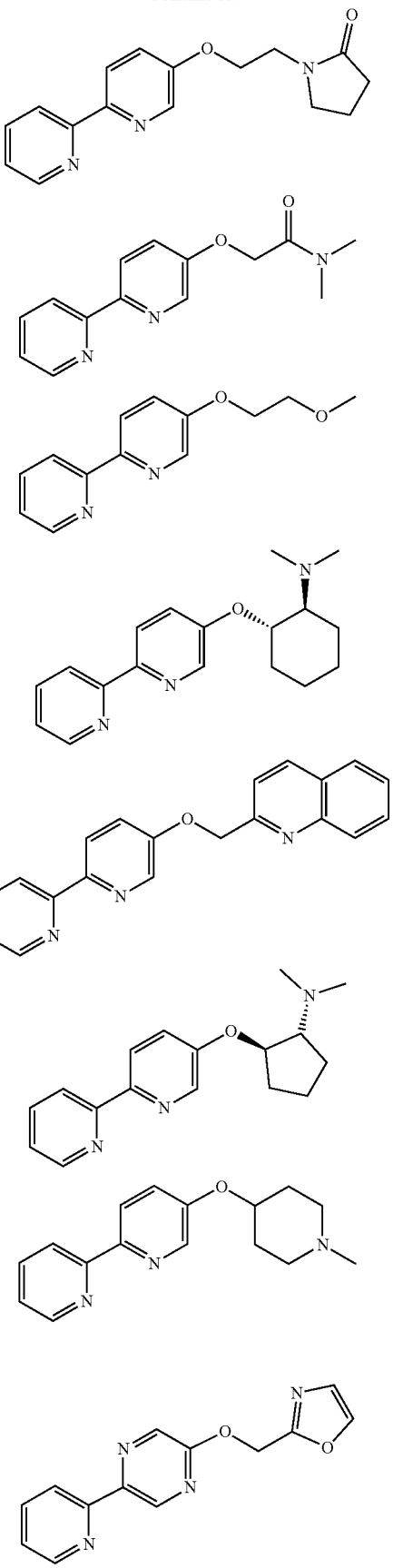

189 190
-continued -continued

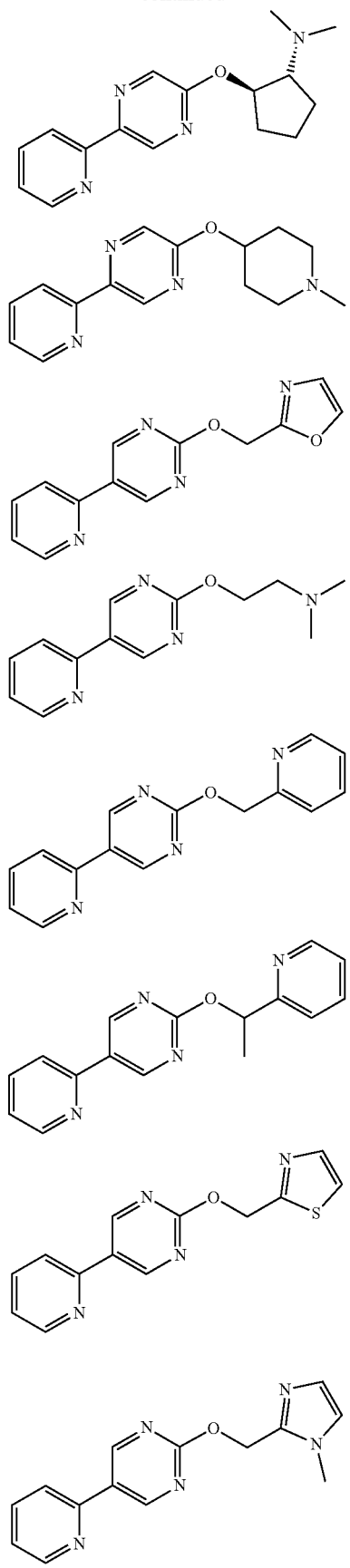
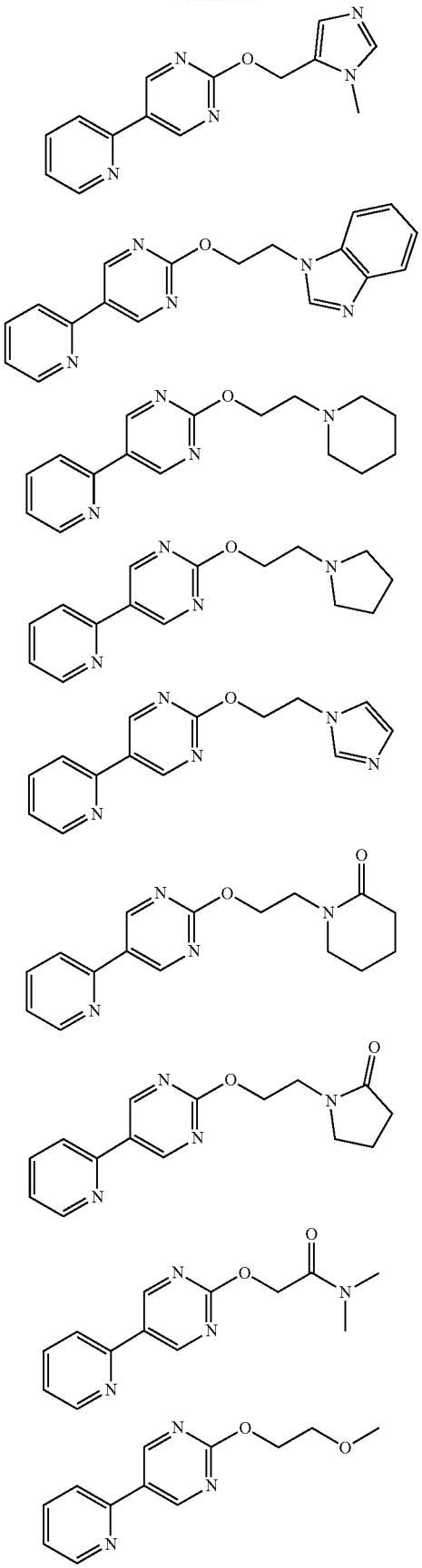

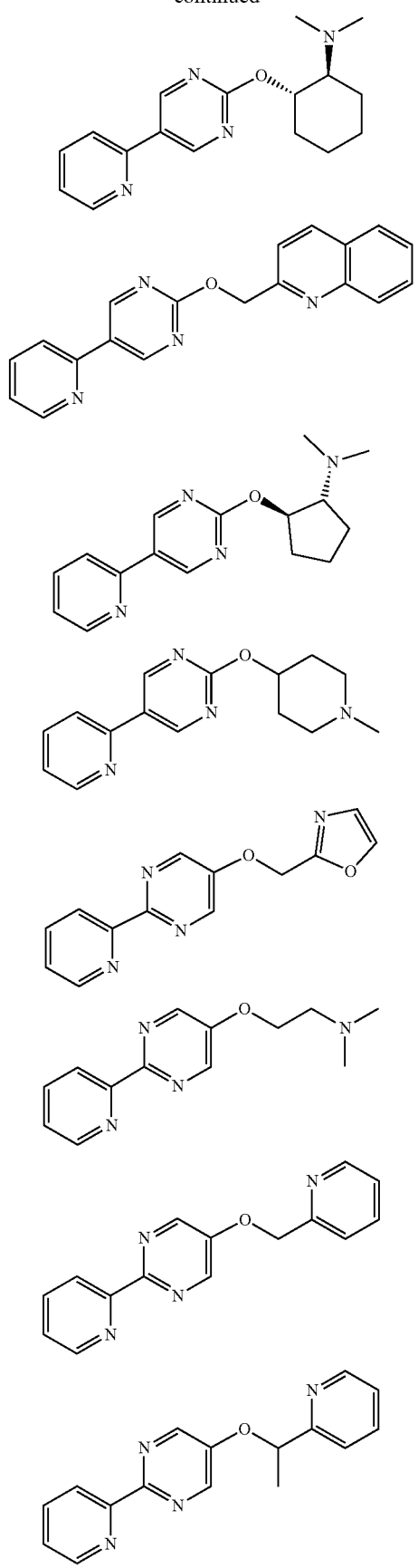
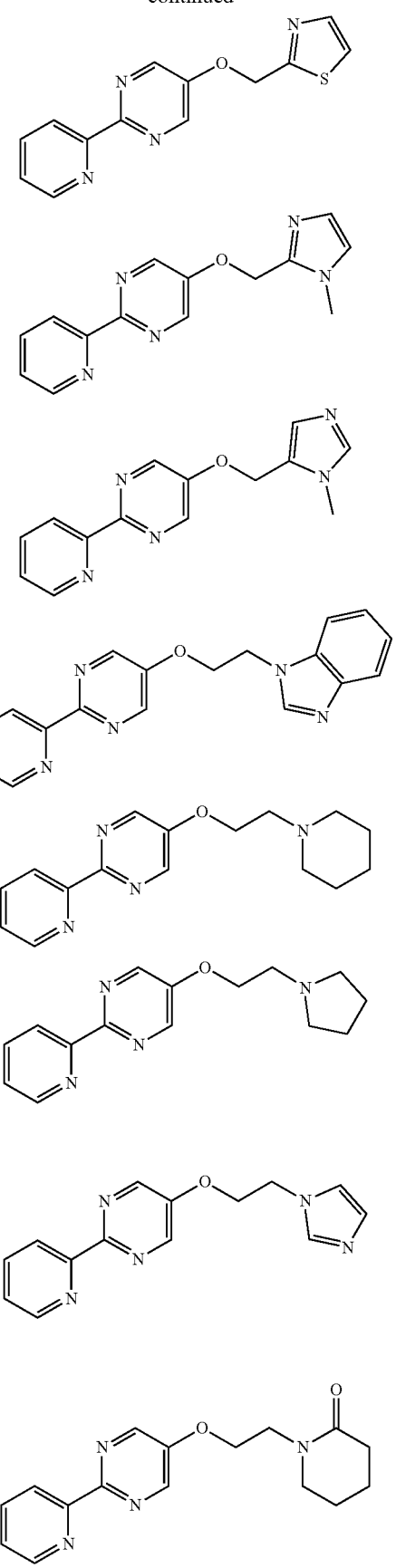

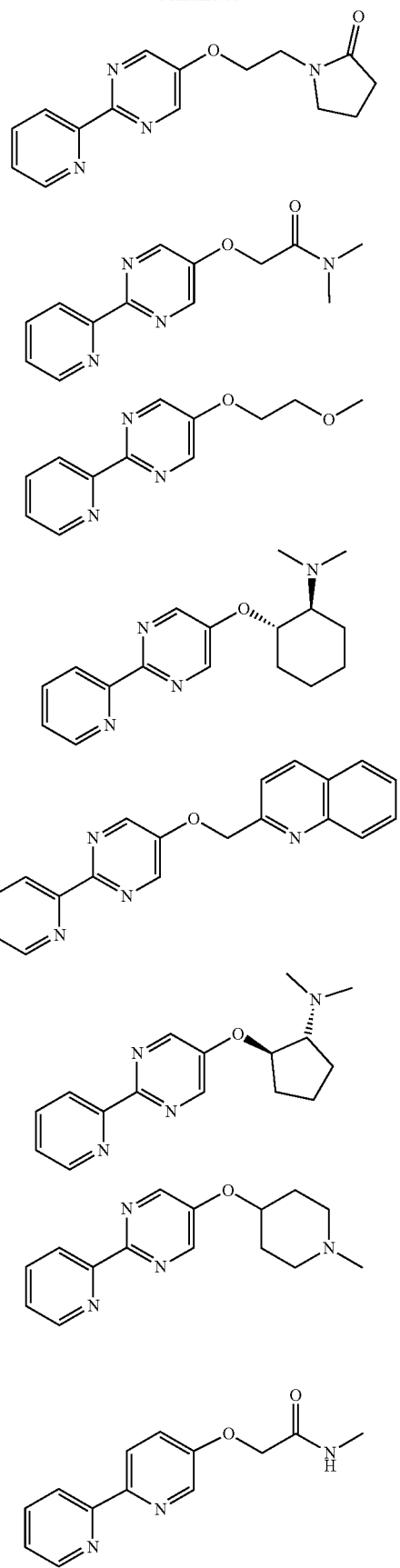
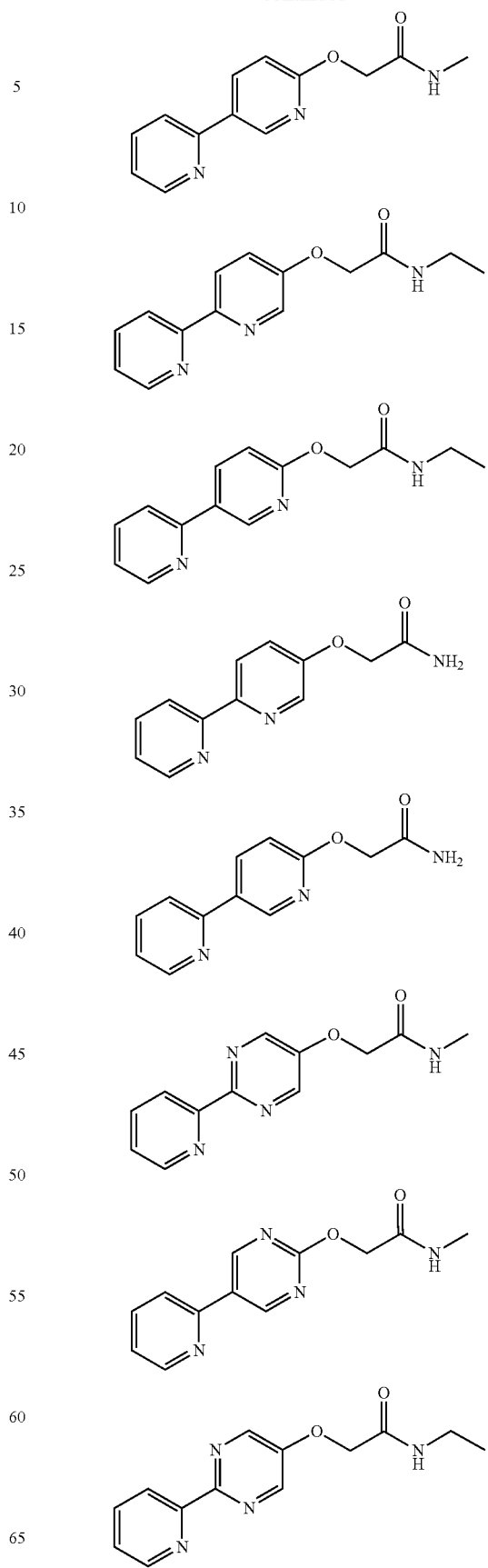

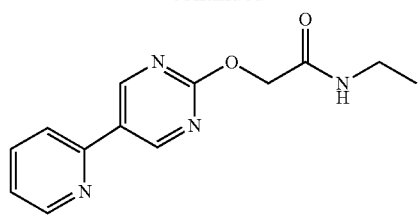
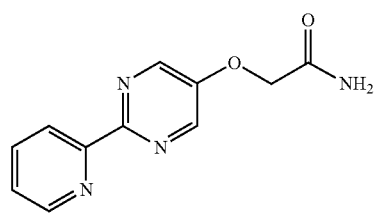
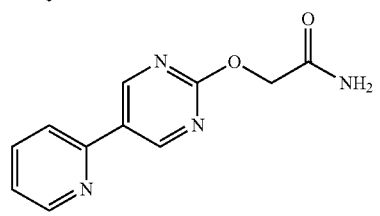
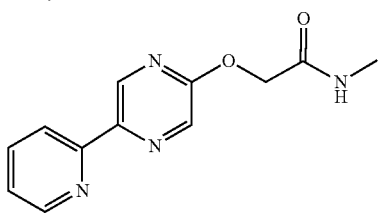
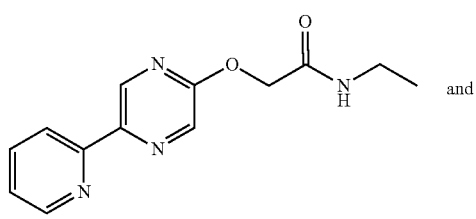 and
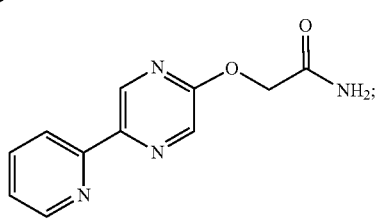
or a pharmaceutically acceptable salt thereof.
17. The compound of claim 14, or a pharmaceutically acceptable salt thereof, wherein the compound of Formula I is selected from the group consisting of:
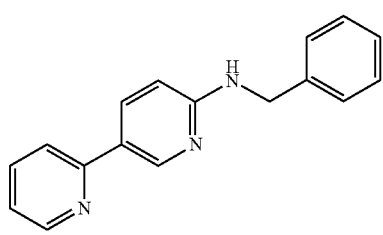
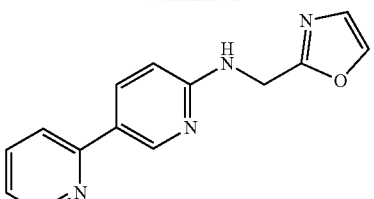
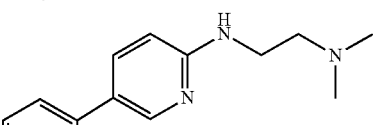
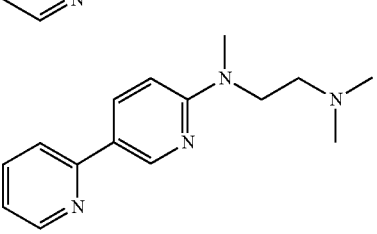
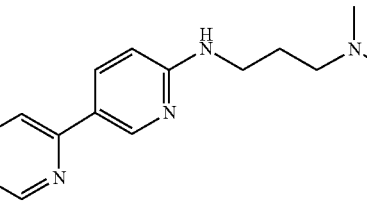
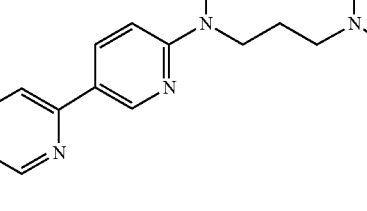
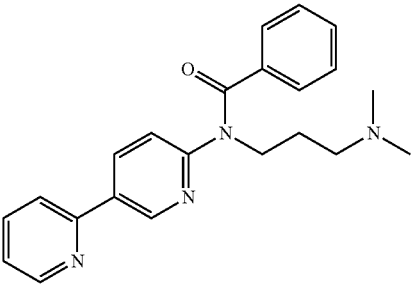
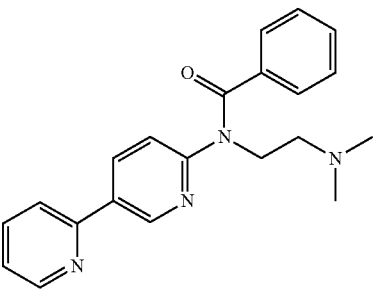

199
-continued
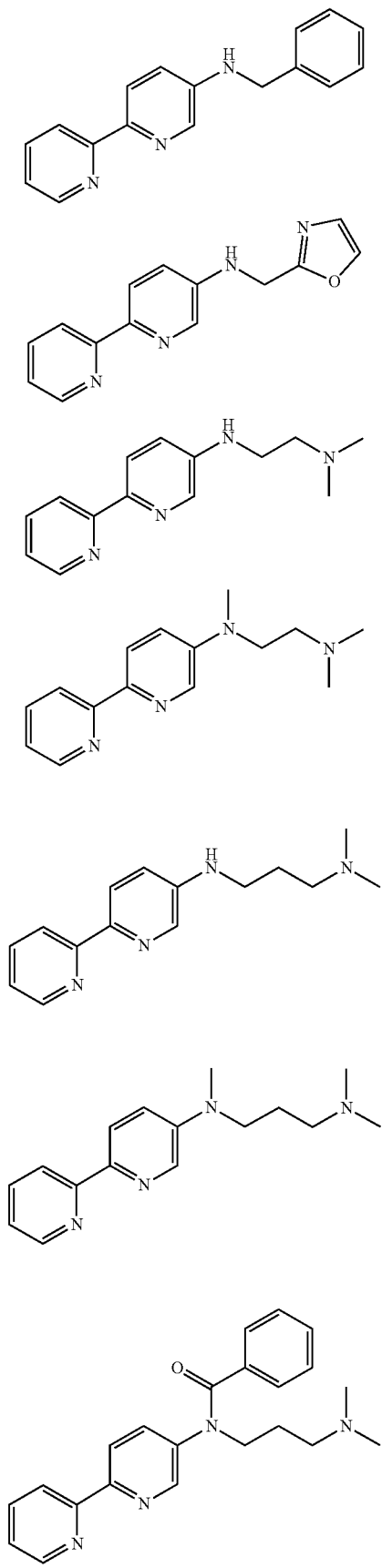
200
-continued
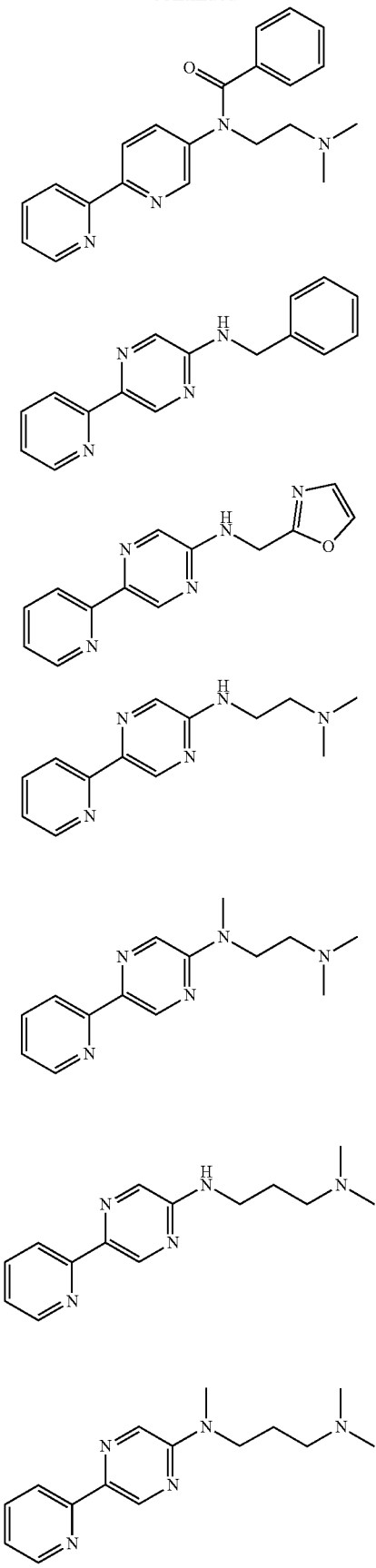

201
-continued
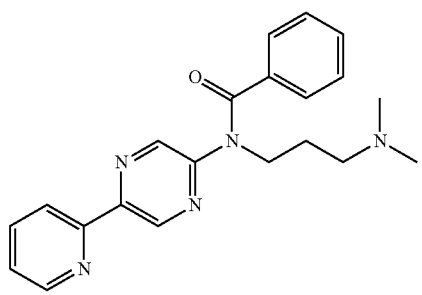
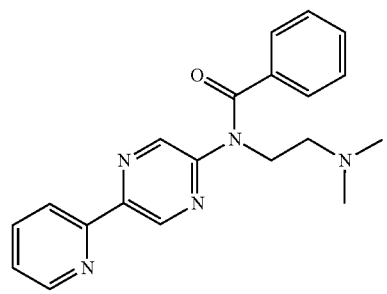
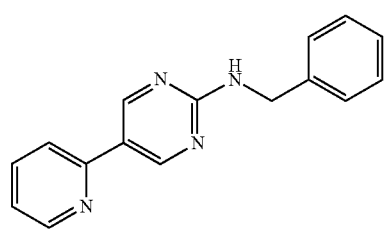
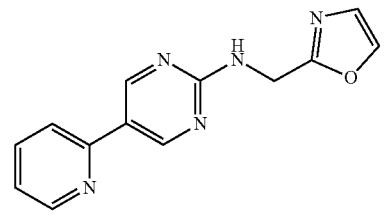
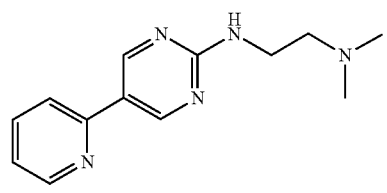
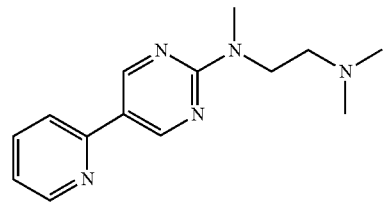
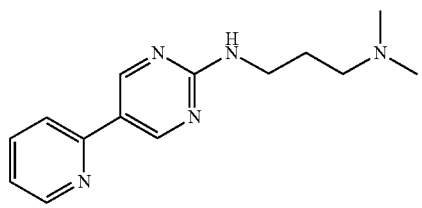
202
-continued
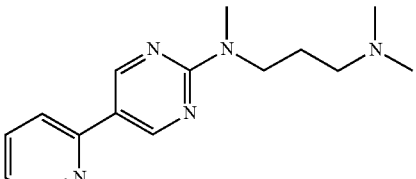
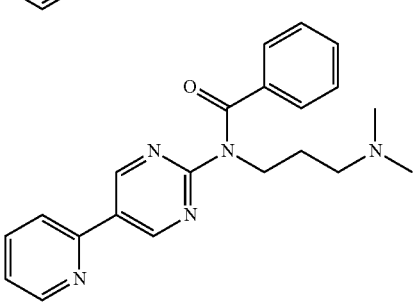
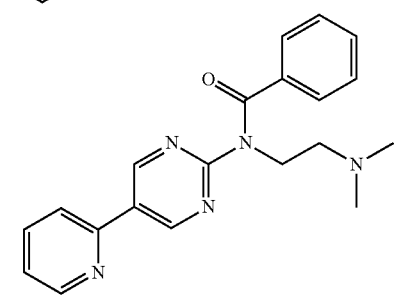
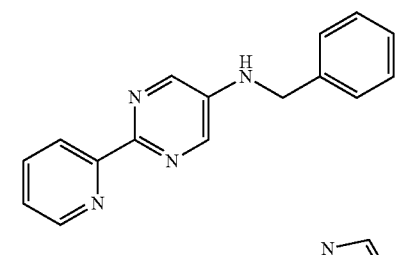
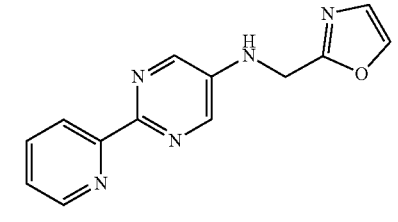
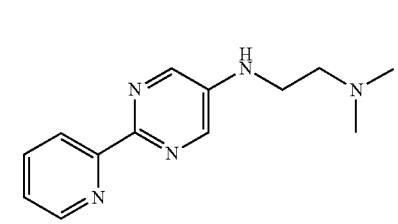
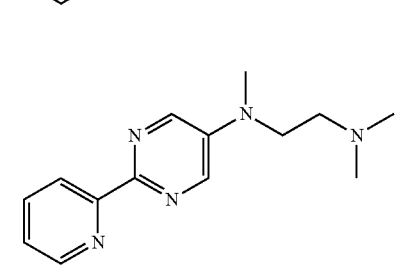

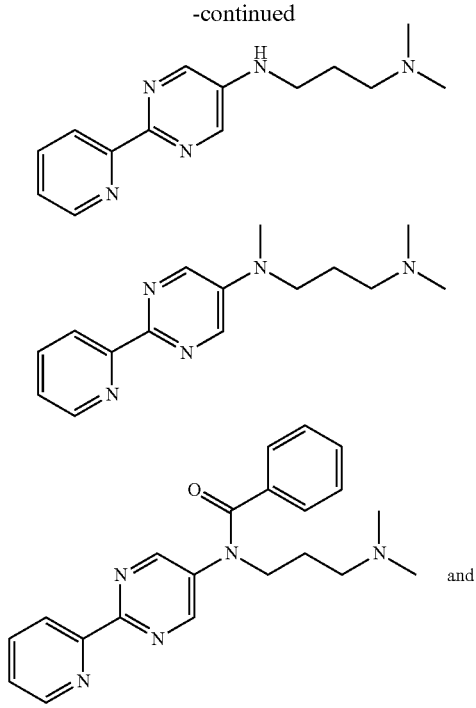

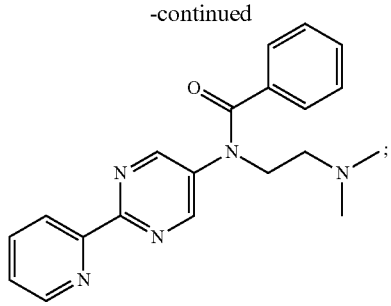

or a pharmaceutically acceptable salt thereof.

18. A pharmaceutical composition comprising a compound of claim 13, or a pharmaceutically acceptable salt thereof, and a pharmaceutically acceptable excipient.

19. A pharmaceutical composition comprising a compound of claim 14, or a pharmaceutically acceptable salt thereof, and a pharmaceutically acceptable excipient.

\* \* \* \* \*